(12) United States Patent
Androsov et al.

(10) Patent No.: US 10,808,080 B2
(45) Date of Patent: Oct. 20, 2020

(54) MONOMER, POLYMER, COMPENSATION FILM, OPTICAL FILM, AND DISPLAY DEVICE

(71) Applicant: SAMSUNG ELECTRONICS CO., LTD., Suwon-si, Gyeonggi-do (KR)

(72) Inventors: Dmitry Androsov, Suwon-si (KR); Changki Kim, Suwon-si (KR); Kalinina Fedosya, Hwaseong-si (KR); Hyunseok Choi, Seoul (KR)

(73) Assignee: SAMSUNG ELECTRONICS CO, LTD., Gyeonggi-Do (KR)

( * ) Notice: Subject to any disclaimer, the term of this patent is extended or adjusted under 35 U.S.C. 154(b) by 184 days.

(21) Appl. No.: 16/048,700

(22) Filed: Jul. 30, 2018

(65) Prior Publication Data

US 2019/0031831 A1 Jan. 31, 2019

(30) Foreign Application Priority Data

Jul. 28, 2017 (KR) ........................ 10-2017-0096550

(51) Int. Cl.

| | |
|---|---|
| C08G 73/16 | (2006.01) |
| C07D 307/89 | (2006.01) |
| C08G 73/10 | (2006.01) |
| G02B 5/30 | (2006.01) |
| G02B 1/04 | (2006.01) |
| C09D 179/08 | (2006.01) |
| H01L 51/52 | (2006.01) |
| G02F 1/13363 | (2006.01) |

(52) U.S. Cl.
CPC ........... *C08G 73/16* (2013.01); *C07D 307/89* (2013.01); *C08G 73/1003* (2013.01); *C08G 73/1039* (2013.01); *C08G 73/1042* (2013.01); *C08G 73/1067* (2013.01); *C09D 179/08* (2013.01); *G02B 1/04* (2013.01); *G02B 5/3083* (2013.01); *G02F 1/13363* (2013.01); *H01L 51/5284* (2013.01)

(58) Field of Classification Search
CPC ..... C07D 307/89; C08G 73/16; C08G 73/101
See application file for complete search history.

(56) References Cited

U.S. PATENT DOCUMENTS

| | | |
|---|---|---|
| 6,350,845 B1 | 2/2002 | Okada et al. |
| 6,642,393 B2 | 11/2003 | Okada et al. |
| 7,019,104 B1 | 3/2006 | Okada et al. |
| 7,396,898 B2 | 7/2008 | Okada |
| 2002/0146726 A1* | 10/2002 | Matray ................ C12Q 1/6823 435/6.13 |
| 2017/0130004 A1 | 5/2017 | Choi et al. |
| 2017/0210854 A1 | 7/2017 | Matsuyama et al. |

FOREIGN PATENT DOCUMENTS

| | | |
|---|---|---|
| JP | 2008-101187 A | 5/2008 |
| KR | 20010049649 A | 6/2001 |
| KR | 20020042733 A | 6/2002 |
| KR | 20030088503 A | 11/2003 |
| WO | 2013-045613 A1 | 4/2013 |

OTHER PUBLICATIONS

USPTO structure search, Jun. 2020.*
Extended European Search Report dated Jan. 8, 2019, issued for the corresponding European Patent Application No. 18185975.2-1102.
English Translation of Notice of Allowance dated Jan. 6, 2020 of the corresponding Korean Patent Application No. 10-2018-0088182.
Notice of Allowance dated Jan. 6, 2020 of the corresponding Korean Patent Application No. 10-2018-0088182.
Masatoshi Hasegawa et al. "Solution-processable transparent polyimides with low coefficients of thermal expansion and self-orientation behavior induced by solution casting", European Polymer Journal 49, (2013) 3657-3672.
Masatoshi Hasegawa et al. "Optically transparent aromatic poly-(ester imide)s with low coefficients of thermal expansion (1). Self-orientation behavior during solution casting process and substituent effect", Polymer 74 (2015) 1-15.
Masatoshi Hasegawa et al. "Poly(ester imide)s Possessing Low Coefficient Thermal Expansion and Low Water Absorption", High Performance Polymers, 18, 697-717, 2006.

* cited by examiner

*Primary Examiner* — Gregory Listvoyb
(74) *Attorney, Agent, or Firm* — Cantor Colburn LLP

(57) ABSTRACT

A monomer is represented by Chemical Formula 1:

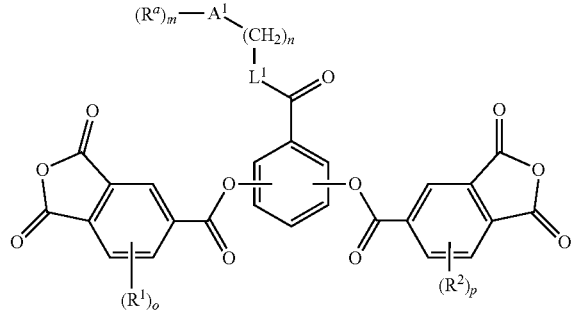

Chemical Formula 1 wherein, in Chemical Formula 1, $R^1$, $R^2$, o, p, $L^1$, $A^1$, $R^a$, m, and n are the same as defined in the detailed description.

6 Claims, 3 Drawing Sheets

MONOMER, POLYMER, COMPENSATION FILM, OPTICAL FILM, AND DISPLAY DEVICE

CROSS-REFERENCE TO RELATED APPLICATION

This application claims priority to Korean Patent Application No. 10-2017-0096550 filed in the Korean Intellectual Property Office on Jul. 28, 2017, and all the benefits accruing therefrom under 35 U.S.C. § 119, the content of which is incorporated herein in its entirety by reference.

BACKGROUND

1. Field

A monomer, a polymer, a compensation film, an optical film, and a display device are disclosed.

2. Description of the Related Art

Research efforts have been undertaken to produce a colorless transparent material that is suitable for diverse purposes such as for an optical lens, a functional optical film, and a disk substrate. However, as information devices are being further miniaturized and display devices are providing higher resolution, more functions and greater performance are required from the material.

Therefore, researcher efforts are currently underway to develop a colorless transparent material having improved transparency, heat resistance, mechanical strength, and flexibility.

SUMMARY

An embodiment provides a novel monomer that is applicable to a compensation film.

Another embodiment provides a polymer obtained by polymerizing the novel monomer.

Yet another embodiment provides a compensation film including the polymer.

Still another embodiment provides an optical film including the compensation film.

Further embodiment provides a display device including the compensation film or the optical film.

An embodiment provides a monomer represented by Chemical Formula 1:

Chemical Formula 1

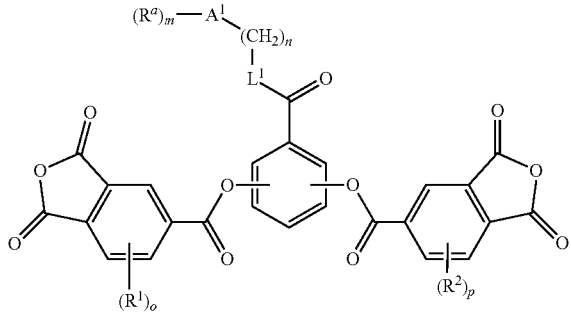

wherein, in Chemical Formula 1,
$R^1$ and $R^2$ are independently a substituted or unsubstituted C1 to C30 alkyl group, a substituted or unsubstituted C1 to C30 cycloalkyl group, a substituted or unsubstituted C3 to C30 alkoxy group, a substituted or unsubstituted C3 to C30 cycloalkoxy group, a substituted or unsubstituted C6 to C30 aryl group, a substituted or unsubstituted C2 to C30 acyl group, a hydroxy group, a halogen, a nitro group, —NR'R" (wherein R' and R" are independently hydrogen, a C1 to C30 alkyl group, or a C6 to C30 aryl group), —SiR'R"R'" (wherein R', R", and R'" are independently hydrogen, a C1 to C30 alkyl group, or a C6 to C30 aryl group), or a combination thereof,
o and p are independently an integer ranging from 0 to 3,
$L^1$ is O or $NR^b$ (wherein $R^b$ is hydrogen or a C1 to C20 alkyl group),
$A^1$ is a C6 to C30 aromatic organic group, and
$R^a$ is hydrogen, a substituted or unsubstituted C1 to C30 alkyl group, a substituted or unsubstituted C1 to C30 alkoxy group, a substituted or unsubstituted C3 to C30 cycloalkyl group, a substituted or unsubstituted C3 to C30 cycloalkoxy group, a substituted or unsubstituted C6 to C30 aryl group, a substituted or unsubstituted C7 to C30 arylalkyl group, a hydroxy group, a halogen, a nitro group, —NR'R" (wherein R' and R" are independently hydrogen, a C1 to C30 alkyl group, a C6 to C30 aryl group, or a C7 to C30 arylalkyl group), —CO—NR'R" (wherein R' and R" are independently hydrogen, a C1 to C30 alkyl group, a C6 to C30 aryl group, or a C7 to C30 arylalkyl group), —SiR'R"R'" (wherein R', R", and R'" are independently hydrogen, a C1 to C30 alkyl group, a C6 to C30 aryl group, or a C7 to C30 arylalkyl group), or a group represented by Chemical Formula 2:

Chemical Formula 2

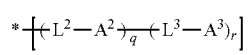

wherein, in Chemical Formula 2,
$L^2$ and $L^3$ are independently O, CO, COO, C≡C, or $CONR^b$ (wherein $R^b$ is hydrogen or a C1 to C30 alkyl group),
$A^2$ and $A^3$ are independently a substituted or unsubstituted C6 to C30 aromatic ring, a substituted or unsubstituted fluorene ring, or a substituted or unsubstituted C7 to C30 arylalkyl group,
q and r are independently an integer ranging from 0 to 3,
m is an integer ranging from 0 to 3, and
n is an integer ranging from 0 to 20.
In Chemical Formula 1,
o and p may independently be 0 or 1,
$L^1$ may be O or $NR^b$ (wherein $R^b$ is hydrogen or a C1 to C20 alkyl group),
$A^1$ may be a C6 to C20 aromatic organic group, and
$R^a$ may be hydrogen, a substituted or unsubstituted C1 to C20 alkyl group, a substituted or unsubstituted C1 to C20 alkoxy group, a substituted or unsubstituted C7 to C20 arylalkyl group, a halogen, —NR'R" (wherein R' and R" are independently hydrogen, a C1 to C30 alkyl group, a C6 to C30 aryl group, or a C7 to C30 arylalkyl group), —CO—NR'R" (wherein R' and R" are independently hydrogen, a C1 to C30 alkyl group, a C6 to C30 aryl group, or a C7 to C30 arylalkyl group), —SiR'R"R'" (wherein R', R", and R'" are independently hydrogen or a C1 to C20 alkyl group), or a group represented by Chemical Formula 2:

Chemical Formula 2

$$*\!\!-\!\!\left[\left(L^2-A^2\right)_{\!q}\!\!-\!\!\left(L^3-A^3\right)_{\!r}\right]$$

wherein, in Chemical Formula 2, $L^2$ and $L^3$ may independently be COO, C≡C, or CONR$^b$ (wherein R$^b$ is hydrogen or a C1 to C20 alkyl group), $A^2$ and $A^3$ may independently be a substituted or unsubstituted C6 to C20 aromatic ring, a substituted or unsubstituted fluorene ring, a substituted or unsubstituted C7 to C20 arylalkyl group, q and r may independently be an integer ranging from 0 to 2, provided that 1≤q+r≤2, m may be an integer ranging from 0 to 2, and n may be an integer of 0 to 10.

In Chemical Formula 1, $L^1$ may be O or NH, $A^1$ may be a benzene ring, and $R^a$ may be hydrogen, a substituted or unsubstituted C1 to C20 alkyl group, a substituted or unsubstituted C1 to C20 alkoxy group, a substituted or unsubstituted C7 to C20 arylalkyl group, a halogen, —CO—NR'R" (wherein R' and R" are independently hydrogen, a C1 to C30 alkyl group, a C6 to C30 aryl group, or a C7 to C30 arylalkyl group), or a group represented by Chemical Formula 2:

Chemical Formula 2

$$*\!\!-\!\!\left[\left(L^2-A^2\right)_{\!q}\!\!-\!\!\left(L^3-A^3\right)_{\!r}\right]$$

wherein, in Chemical Formula 2, $L^2$ and $L^3$ may independently be COO, C≡C, or CONR$^b$ (wherein R$^b$ is hydrogen or a C1 to C20 alkyl group), $A^2$ and $A^3$ may independently be a substituted or unsubstituted benzene ring, a substituted or unsubstituted fluorene ring, or a substituted or unsubstituted C7 to C20 arylalkyl group, q and r may independently be an integer ranging from 0 to 2, provided that 1≤q+r≤2, m may be 0 or 1, and n may be an integer of 0 to 5.

The monomer represented by Chemical Formula 1 may be a monomer represented by Chemical Formula 3 or Chemical Formula 4:

Chemical Formula 3

Chemical Formula 4

In Chemical Formula 3 and Chemical Formula 4, $R^1$ and $R^2$ are independently a substituted or unsubstituted C1 to C30 alkyl group, a substituted or unsubstituted C3 to C30 cycloalkyl group, a substituted or unsubstituted C1 to C30 alkoxy group, a substituted or unsubstituted C3 to C30 cycloalkoxy group, a substituted or unsubstituted C6 to C30 aryl group, a substituted or unsubstituted C2 to C30 acyl group, a hydroxy group, a halogen, a nitro group, —NR'R" (wherein R' and R" are independently hydrogen, a C1 to C30 alkyl group, or a C6 to C30 aryl group), —SiR'R"R'" (wherein R', R", and R'" are independently hydrogen or a C1 to C20 alkyl group), or a combination thereof, o and p are independently an integer ranging from 0 to 3, $L^1$ is O or NR$^b$(wherein R$^b$ is hydrogen or a C1 to C20 alkyl group), $A^1$ is a C6 to C30 aromatic organic group, and $R^a$ is hydrogen, a substituted or unsubstituted C1 to C30 alkyl group, a substituted or unsubstituted C1 to C30 alkoxy group, a substituted or unsubstituted C3 to C30 cycloalkyl group, a substituted or unsubstituted C3 to C30 cycloalkoxy group, a substituted or unsubstituted C6 to C30 aryl group, a substituted or unsubstituted C7 to C30 arylalkyl group, a hydroxy group, a halogen, a nitro group, —NR'R" (wherein R' and R" are independently hydrogen, a C1 to C30 alkyl group, a C6 to C30 aryl group, or a C7 to C30 arylalkyl group), —CO—NR'R" (wherein R' and R" are independently hydrogen, a C1 to C30 alkyl group, a C6 to C30 aryl group, or a C7 to C30 arylalkyl group), —SiR'R"R'" (wherein R', R", and R'" are independently hydrogen, a C1 to C30 alkyl group, a C6 to C30 aryl group, or a C7 to C30 arylalkyl group), or a group represented by Chemical Formula 2:

Chemical Formula 2

$$*\!\!-\!\!\left[\left(L^2-A^2\right)_{\!q}\!\!-\!\!\left(L^3-A^3\right)_{\!r}\right]$$

wherein, in Chemical Formula 2, $L^2$ and $L^3$ are independently O, CO, COO, C≡C, or CONR$^b$ (wherein R$^b$ is hydrogen or a C1 to C30 alkyl group), $A^2$ and $A^3$ are independently a substituted or unsubstituted C6 to C30 aromatic ring, a substituted or unsubstituted fluorene ring, or a substituted or unsubstituted C7 to C30 arylalkyl group, q and r are independently an integer ranging from 0 to 3, m is an integer ranging from 0 to 3, and n is an integer ranging from 0 to 20.

In Chemical Formula 3 and Chemical Formula 4, o and p may independently be 0 or 1, $L^1$ may be O or $NR^b$ (wherein $R^b$ is hydrogen or a C1 to C20 alkyl group), $A^1$ may be a C6 to C20 aromatic organic group, and $R^a$ may be hydrogen, a substituted or unsubstituted C1 to C20 alkyl group, a substituted or unsubstituted C1 to C20 alkoxy group, a substituted or unsubstituted C7 to C20 arylalkyl group, a halogen, —NR'R" (wherein R' and R" are independently hydrogen, a C1 to C30 alkyl group, a C6 to C30 aryl group, or a C7 to C30 arylalkyl group), —CO—NR'R" (wherein R' and R" are independently hydrogen, a C1 to C30 alkyl group, a C6 to C30 aryl group, or a C7 to C30 arylalkyl group), —SiR'R"R'" (wherein R', R", and R'" are independently hydrogen, a C1 to C20 alkyl group, a C6 to C30 aryl group, or a C7 to C30 arylalkyl group), or a group represented by Chemical Formula 2:

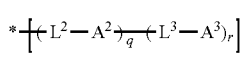

Chemical Formula 2 wherein, in Chemical Formula 2, $L^2$ and $L^3$ may independently be COO, C≡C, or $CONR^b$ (wherein $R^b$ is hydrogen or a C1 to C20 alkyl group), $A^2$ and $A^3$ may independently be a substituted or unsubstituted C6 to C20 aromatic ring, a substituted or unsubstituted fluorene ring, or a substituted or unsubstituted C7 to C20 arylalkyl group, q and r may independently be an integer ranging from 0 to 2, provided that 1≤q+r≤2, and m may be 0 or 1, and n may be an integer of 0 to 10.

In Chemical Formula 3 and Chemical Formula 4, o and p may be 0, $L^1$ may be O or NH, $A^1$ may be a benzene ring, and $R^a$ may be hydrogen, a substituted or unsubstituted C1 to C10 alkyl group, a substituted or unsubstituted C1 to C10 alkoxy group, a halogen, —CO—NR'R" (wherein R' and R" are independently hydrogen, a C1 to C30 alkyl group, a C6 to C30 aryl group, or a C7 to C30 arylalkyl group), or a group represented by Chemical Formula 2:

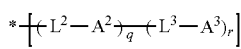

Chemical Formula 2 wherein, in Chemical Formula 2, $L^2$ and $L^3$ may independently be COO, C≡C, or $CONR^b$ (wherein $R^b$ is hydrogen or a C1 to C20 alkyl group), $A^2$ and $A^3$ may independently be a substituted or unsubstituted benzene ring, a substituted or unsubstituted fluorene ring, or a substituted or unsubstituted C7 to C20 arylalkyl group, q and r may independently be an integer ranging from 0 to 2, provided that 1≤q+r≤2, m may be 0 or 1, and n may be an integer of 0 to 5.

In another embodiment, provided is a polymer is a product of reactants including the monomer according to an embodiment and diamine.

The diamine may be represented by Chemical Formula 5:

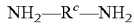

Chemical Formula 5 wherein, in Chemical Formula 5, $R^c$ is a substituted or unsubstituted C6 to C30 aromatic organic group, wherein the substituted or unsubstituted C6 to C30 aromatic organic group is present as a single aromatic ring; a fused ring including two or more aromatic rings; or a ring system including two or more of the single aromatic ring and/or the fused ring that are linked by a single bond, or a functional group selected from a fluorenylene group, a substituted or unsubstituted C1 to C10 cycloalkylene group, a substituted or unsubstituted C6 to C15 arylene group, —O—, —S—, —C(=O)—, —CH(OH)—, —S(=O)$_2$—, —Si(CH$_3$)$_2$—, —(CH$_2$)$_p$— (wherein, 1≤p≤10), —(CF$_2$)$_q$— (wherein, 1≤q≤10), —C(CH$_3$)$_2$—, —C(CF$_3$)$_2$—, —C(=O)NH—, or a combination thereof.

The diamine represented by Chemical Formula 5 may be represented by at least one of Chemical Formula 6 to Chemical Formula 8:

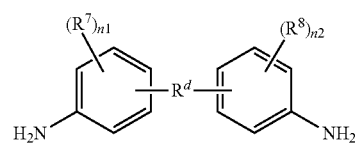

Chemical Formula 6 wherein, in Chemical Formula 6, $R^d$ is selected from chemical formulae:

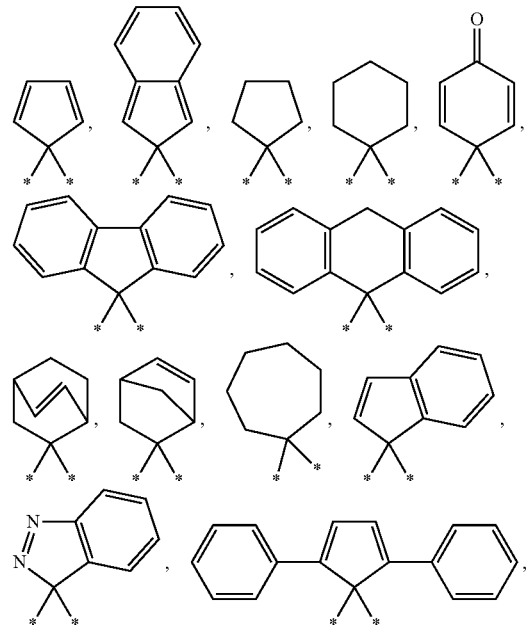

$R^7$ and $R^8$ are the same or different and are independently a halogen, a hydroxy group, an alkoxy group (—OR$^{200}$, wherein R$^{200}$ is a C1 to C10 aliphatic organic group), a silyl group (—SiR$^{201}$R$^{202}$R$^{203}$, wherein R$^{201}$, R$^{202}$, and R$^{203}$ are the same or different and are independently hydrogen or a C1 to C10 aliphatic organic group), a substituted or unsubstituted C1 to C10 aliphatic organic group, or a substituted or unsubstituted C6 to C20 aromatic organic group, and n1 and n2 are independently an integer ranging from 0 to 4;

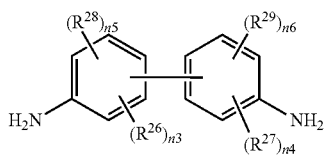

Chemical Formula 7 wherein, in Chemical Formula 7, $R^{26}$ and $R^{27}$ are the same or different and are independently an electron withdrawing group selected from —$CF_3$, —$CCl_3$, —$CBr_3$, —$Cl_3$, —$NO_2$, —CN, —$COCH_3$, or —$CO_2C_2H_5$, $R^{28}$ and $R^{29}$ are the same or different and are independently a halogen, a hydroxy group, an alkoxy group (—$OR^{204}$, wherein $R^{204}$ is a C1 to C10 aliphatic organic group), a silyl group (—$SiR^{205}R^{206}R^{207}$, wherein $R^{205}$, $R^{206}$, and $R^{207}$ are the same or different and are independently hydrogen or a C1 to C10 aliphatic organic group), a substituted or unsubstituted C1 to C10 aliphatic organic group, or a substituted or unsubstituted C6 to C20 aromatic organic group, n3 is an integer ranging from 1 to 4, n5 is an integer ranging from 0 to 3, and n3+n5 is an integer ranging from 1 to 4, and n4 is an integer ranging from 1 to 4, n6 is an integer ranging from 0 to 3, and n4+n6 is an integer ranging from 1 to 4;

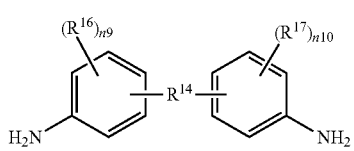

Chemical Formula 8 wherein, in Chemical Formula 8, $R^{14}$ is O, S, C(=O), CH(OH), S(=O)$_2$, Si(CH$_3$)$_2$, (CH$_2$)$_p$ (wherein, 1≤p≤10), (CF$_2$)$_q$ (wherein, 1≤q≤10), C(CH$_3$)$_2$, C(CF$_3$)$_2$, C(=O)NH, or a substituted or unsubstituted C6 to C18 aromatic organic group, wherein the C6 to C18 aromatic organic group is present as a single aromatic ring, a fused ring including two or more aromatic rings, or a ring system including two or more of the single aromatic ring and/or the fused ring that are linked by a single bond, or a functional group selected from a fluorenylene group, O, S, C(=O), CH(OH), S(=O)$_2$, Si(CH$_3$)$_2$, (CH$_2$)$_p$ (wherein, 1≤p≤10), (CF$_2$)$_q$ (wherein, 1≤q≤10), C(CH$_3$)$_2$, C(CF$_3$)$_2$, or C(=O)NH, $R^{16}$ and $R^{17}$ are the same or different and are independently a halogen, a hydroxy group, an alkoxy group (—$OR^{212}$, wherein $R^{212}$ is a C1 to C10 aliphatic organic group), a silyl group (—$SiR^{213}R^{214}R^{215}$, wherein $R^{213}$, $R^{214}$, and $R^{215}$ are the same or different and are independently hydrogen or a C1 to C10 aliphatic organic group), a substituted or unsubstituted C1 to C10 aliphatic organic group, or a substituted or unsubstituted C6 to C20 aromatic organic group, and n9 and n10 are independently an integer ranging from 0 to 4.

The polymer according to an embodiment may be a product of reactants including at least one of the diamine represented by Chemical Formula 7 and the diamine represented by Chemical Formula 8.

The polymer may be a product of reactants wherein the diamine represented by Chemical Formula 7 may include 2,2'-bis(trifluoromethyl)benzidine (TFDB) and the diamine represented by Chemical Formula 8 may include 4,4'-diaminodiphenyl sulfone (DADPS).

The polymer according to an embodiment may be a product of reactants that further include dianhydride represented by Chemical Formula 9:

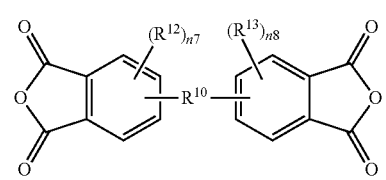

Chemcial Formula 9 wherein, in Chemical Formula 9, $R^{10}$ is a single bond, —O—, —S—, —C(=O)—, —CH(OH)—, —C(=O)NH—, —S(=O)$_2$—, —Si(CH$_3$)$_2$—, —(CH$_2$)$_p$—, —(CF$_2$)$_q$—, —C(C$_n$H$_{2n+1}$)$_2$—, —C(C$_n$F$_{2n+1}$)$_2$—, —(CH$_2$)$_p$—C(C$_n$H$_{2n+1}$)$_2$—(CH$_2$)$_q$—, or —(CH$_2$)$_p$—C(C$_n$F$_{2n+1}$)$_2$—(CH$_2$)$_q$— (wherein 1≤n≤10, 1≤p≤10, and 1≤q≤10), $R^{12}$ and $R^{13}$ are independently a halogen, a hydroxy group, a substituted or unsubstituted C1 to C10 aliphatic organic group, a substituted or unsubstituted C6 to C20 aromatic organic group, a —$OR^{201}$ group (wherein $R^{201}$ is a C1 to C10 aliphatic organic group), or a —$SiR^{210}R^{211}R^{212}$ (wherein $R^{210}$, $R^{211}$, and $R^{212}$ are independently hydrogen or a C1 to C10 aliphatic organic group) group, and n7 and n8 are independently one of integers of 0 to 3.

The dianhydride represented by Chemical Formula 9 may include dianhydride represented by Chemical Formula 10, dianhydride represented by Chemical Formula 11, or a combination thereof:

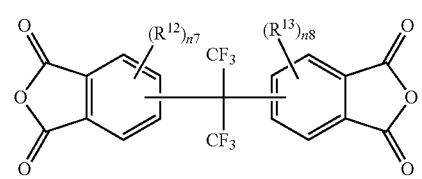

Chemical Formula 10

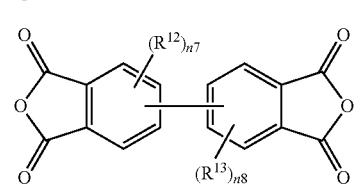

Chemical Formula 11 wherein, in Chemical Formula 10 and Chemical Formula 11, $R^{12}$ and $R^{13}$ are the same or different and are independently a halogen, a hydroxy group, an alkoxy group (—$OR^{208}$, wherein $R^{208}$ is a C1 to C10 aliphatic organic group), a silyl group (—$SiR^{209}R^{210}R^{211}$, wherein $R^{209}$, $R^{210}$, and $R^{211}$ are the same or different and are independently hydrogen or a C1 to C10 aliphatic organic group), a substituted or unsubstituted C1 to C10 aliphatic organic group, or a substituted or unsubstituted C6 to C20 aromatic organic group, and n7 and n8 are independently an integer ranging from 0 to 3.

The polymer may be a product of reactants including the monomer according to an embodiment, and at least one of the dianhydride represented by Chemical Formula 10 and the dianhydride represented by Chemical Formula 11 in a mole ratio of about 90:10 to about 10:90.

The polymer according to an embodiment may be a product of reactants that further includes dicarboxylic acid derivative represented by Chemical Formula 12:

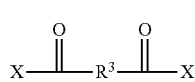

Chemical Formula 12 wherein, in Chemical Formula 12, $R^3$ is at least one of a substituted or unsubstituted phenylene group and a substituted or unsubstituted biphenylene group, and X's are independently the same or different halogen atom.

In Chemical Formula 12, $R^3$ may be at least one of an unsubstituted phenylene group and an unsubstituted biphenylene group, and X's may independently be Cl or Br.

Another embodiment provides a compensation film including the polymer according to the embodiment.

Another embodiment provides an optical film including the compensation film according to the embodiment and a polarizer.

Another embodiment provides a display device including the compensation film according to the embodiment.

Another embodiment provides a display device including the optical film according to the embodiment.

A novel monomer according to an embodiment reacts with diamine, and thus, may be used to form a polyesterimide film having high transmittance, a low yellow index, and low haze and also, a high out-of-plane birefringence and is prepared from inexpensive raw materials and accordingly may be used to manufacture an optical film requiring high optical characteristics and mechanical properties.

BRIEF DESCRIPTION OF THE DRAWINGS

The above and other aspects, advantages and features of this disclosure will become more apparent by describing in further detail exemplary embodiments thereof with reference to the accompanying drawings, in which.

DETAILED DESCRIPTION

Figure 1:
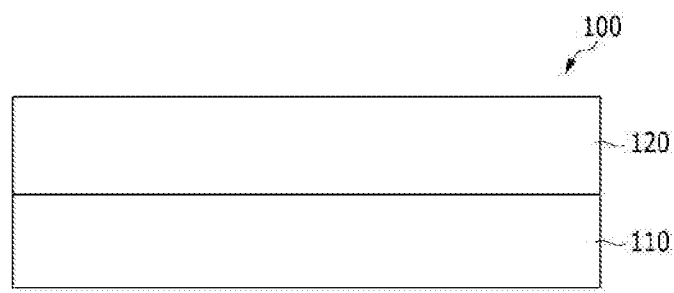
FIG. 1 is a schematic cross-sectional view showing an optical film according to an embodiment.

Hereinafter, exemplary embodiments will be described in detail, and may be readily performed by those who have common knowledge in the related art. However, this disclosure may be embodied in many different forms and should not be construed as limited to the exemplary embodiments set forth herein.

Accordingly, the embodiments are merely described below, by referring to the figures, to explain aspects of the present description. As used herein, the term "and/or" includes any and all combinations of one or more of the associated listed items. The term "or" means "and/or." Expressions such as "at least one of" when preceding a list of elements, modify the entire list of elements and do not modify the individual elements of the list.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an" and "the" are intended to include the plural forms as well, unless the context clearly indicates otherwise. The term "or" means "and/or." As used herein, the term "and/or" includes any and all combinations of one or more of the associated listed items. Expressions such as "at least one of," when preceding a list of elements, modify the entire list of elements and do not modify the individual elements of the list.

It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system).

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or non-linear features. Moreover, sharp angles that are illustrated may be rounded. Thus, the regions illustrated in the figures are schematic in nature and their shapes are not intended to illustrate the precise shape of a region and are not intended to limit the scope of the present claims.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

As used herein, when a definition is not otherwise provided, the term "substituted" refers to replacement of a hydrogen atom of a compound or a functional group by a substituent selected from a halogen atom, a hydroxy group, an alkoxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, phosphoric acid or a salt thereof, a C1 to C20 alkyl group, a C2 to C20 alkenyl group, a C2 to C20 alkynyl group, a C6 to C30 aryl group, a C7 to C30 arylalkyl group, a C1 to C30 alkoxy group, a C1 to C20 heteroalkyl group, a C3 to C20 heteroarylalkyl group, a C3 to C30 cycloalkyl group, a C3 to C15 cycloalkenyl group, a C6 to C15 cycloalkynyl group, a C3 to C30 heterocycloalkyl group, and a combination thereof.

As used herein, when a definition is not otherwise provided, the term "hetero" refers to inclusion of 1 to 3 hetero atoms selected from N, O, S, Se, and P.

As used herein, when a definition is not otherwise provided, the term "alkyl" indicates a group derived from a completely saturated, branched or unbranched (or a straight or linear) hydrocarbon and having a specified number of carbon atoms.

As used herein, the term "cycloalkyl group" refers to a monovalent group having one or more saturated rings in which all ring members are carbon. Non-limiting examples of the cycloalkyl group are cyclopentyl and cyclohexyl.

As used herein, when a definition is not otherwise provided, the term "alkoxy" represents "alkyl-O—", wherein the term "alkyl" has the same meaning as described above.

As used herein, when a definition is not otherwise provided, the term "cycloalkoxy" represents "cycloalkyl-O—", wherein the term "cycloalkyl" has the same meaning as described above.

As used herein, when a definition is not otherwise provided, the term "acyl" represents "alkyl-C(=O)—", wherein the term "alkyl" has the same meaning as described above.

As used herein, when a definition is not otherwise provided, the term "aryl" indicates an aromatic hydrocarbon containing at least one ring and having the specified number of carbon atoms.

As used herein, when a definition is not otherwise provided, the term "arylalkyl" represents "aryl-alkyl-", wherein the terms "aryl" and "alkyl" have the same meaning as described above.

As used herein, the term "alkylene" indicates a straight or branched saturated aliphatic hydrocarbon group having a valence of at least two, optionally substituted with one or more substituents where indicated, provided that the valence of the alkylene group is not exceeded.

As used herein, when a definition is not otherwise provided, the term "arylene" indicates a divalent group formed by the removal of two hydrogen atoms from one or more rings of an arene, wherein the hydrogen atoms may be removed from the same or different rings of the arene.

As used herein, when a definition is not otherwise provided, the term "heteroalkylene" indicates a straight or branched saturated aliphatic hydrocarbon group having a valence of at least two, optionally substituted with one or more substituents where indicated, provided that the valence of the alkylene group is not exceeded, and including one or more heteroatoms selected from nitrogen (N), oxygen (O), sulfur (S), and phosphorus (P).

As used herein, when a definition is not otherwise provided, the term "alkylarylene" indicates an arylene group substituted with an alkylene group, wherein the terms "arylene" and "alkylene" have the same meaning as described above.

As used herein, when a definition is not otherwise provided, the term "arylalkylene" indicates an alkylene group substituted with an arylene group, wherein the terms "alkylene" and "arylene" have the same meaning as described above.

An optically transparent heat resistant polymer described herein may be applied to various optoelectronic devices, for example, an image device, a liquid crystal alignment layer, a color filter, an optical compensation film, an optic fiber, a light guide, optical lens, and the like. In this regard, research efforts have been recently made to realize a remarkably light and flexible display panel by replacing a fragile inorganic glass substrate (e.g., about 300 nanometers (nm_to about 700 millimeters (mm) thick) in an image device with a plastic substrate (<about 50 mm thick).

However, the plastic substrate has not secured reliability yet, because it is difficult to simultaneously achieve optical transmittance, heat resistance, dimensional stability (thermal dimensional stability) at a thermal cycle during the assembly process of a device, film flexibility, and film-forming process compatibility (a solution process) in a high level. The plastic substrate is excellent in terms of flexibility and thin film formality but inferior in terms of heat resistance and thermal dimensional stability compared with the inorganic glass substrate.

Poly(ether sulfone) (PES) is known to have the highest glass transition temperature ($T_g$, 225° C.) among commercially available super engineering plastics. However, PES may be not suitable as the plastic substrate in terms of heat resistance and thermal dimensional stability. A plastic substrate having insufficient thermal dimensional stability may be thermally expanded/contracted during repetitive heating/cooling cycles in a process of forming an ITO (indium tin oxide) electrode and a thin film transistor, and thus, may destroy an ITO layer.

A high temperature polymer material having the highest reliability may be polyimide (PI). A part of aromatic PI systems simultaneously has much higher $T_g$ than a device operating temperature and a low linear coefficient of thermal expansion (CTE) along a film plane (X-Y) direction in a glassy region, and thus, excellent thermal dimensional stability. However, common aromatic PI is strongly colored due to a charge transfer (CT) interaction and often disturbs an optical device. Accordingly, academic and industrial research on a coloring/discoloring mechanism of an aromatic PI film has been widely conducted. One of effective approaches for discoloring the film is to block the CT interaction by selecting a non-aromatic (alicyclic) monomer from diamine, tetracarboxylic dianhydride, or both of them.

However, the alicyclic monomer may cause a serious problem in some uses. In other words, a partly or wholly alicyclic PI film often has insufficient thermal dimensional stability due to a high linear coefficient of thermal expansion CTE (>60 parts per million per Kelvin, ppm $K^{-1}$) in the glassy region despite a high glass transition temperature $T_g$ (>300° C.). This high linear coefficient of thermal expansion is actually generated from a randomly three dimensionally disposed chain alignment. The alicyclic monomer mostly has a non-linear/non-planar cubic structure. As a result, linearity of a PI main chain is completely destroyed. In this twisted backbone structure, chains may not be highly aligned along an X-Y direction (hereinafter, "planar alignment") during a thermal imidization process. Among the alicyclic monomers, 1,2,3,4-cyclobutane tetracarboxylic dianhydride (CBDA) and trans-1,4-cyclohexane diamine (t-CHDA) uncommonly has a rigid and linear structure. However, a solution process may not be applied to final PI using this monomer. A wholly aromatic PI system induced from 4,4'-(hexafluoroisopropylidene) diphthalic anhydride (6FDA) and 2,2'-bis(trifluoromethyl)benzidine (TFMB) has no low coefficient of thermal expansion due to a non-linear/non-coplanar cubic structure of a 6-FDA-based diimide unit but high transparency and excellent solubility.

Accordingly, a plastic material simultaneously satisfying desired various characteristics, and thus, having high reliability is difficult to develop.

The present inventors synthesize a novel monomer capable of forming polyimide simultaneously satisfying thermal stability and optical transparency, and thus, has completed the present invention by confirming that a polymer formed from the monomer has particular optical properties, for example, high transparency, as well as high out-of-plane birefringence, and in addition, high thermal stability due to a high glass transition temperature.

The monomer may be represented by Chemical Formula 1:

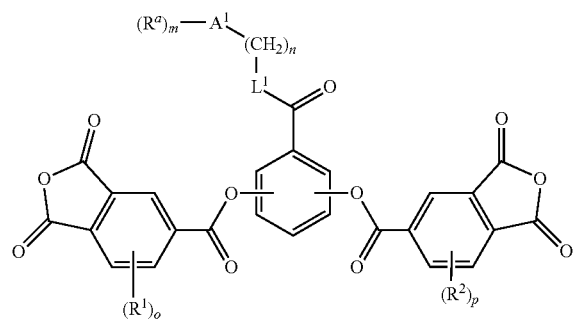

Chemical Formula 1 wherein, in Chemical Formula 1, $R^1$ and $R^2$ are independently a substituted or unsubstituted C1 to C30 alkyl group, a substituted or unsubstituted C1 to C30 cycloalkyl group, a substituted or unsubstituted C3 to C30 alkoxy group, a substituted or unsubstituted C3 to C30 cycloalkoxy group, a substituted or unsubstituted C6 to C30 aryl group, a substituted or unsubstituted C2 to C30 acyl group, a hydroxy group, a halogen, a nitro group, —NR'R" (wherein R' and R" are independently hydrogen, a C1 to C30 alkyl group, or a C6 to C30 aryl group), —SiR'R"R'" (wherein R', R", and R'" are independently hydrogen, a C1 to C30 alkyl group, or a C6 to C30 aryl group), or a combination thereof, o and p are independently an integer ranging from 0 to 3, $L^1$ is O or $NR^b$ (wherein $R^b$ is hydrogen or a C1 to C20 alkyl group), $A^1$ is a C6 to C30 aromatic organic group, and $R^a$ is hydrogen, a substituted or unsubstituted C1 to C30 alkyl group, a substituted or unsubstituted C1 to C30 alkoxy group, a substituted or unsubstituted C3 to C30 cycloalkyl group, a substituted or unsubstituted C3 to C30 cycloalkoxy group, a substituted or unsubstituted C6 to C30 aryl group, a substituted or unsubstituted C7 to C30 arylalkyl group, a hydroxy group, a halogen, a nitro group, —NR'R" (wherein R' and R" are independently hydrogen, a C1 to C30 alkyl group, a C6 to C30 aryl group, or a C7 to C30 arylalkyl group), —CO—NR'R" (wherein R' and R" are independently hydrogen, a C1 to C30 alkyl group, a C6 to C30 aryl group, or a C7 to C30 arylalkyl group), —SiR'R"R'" (wherein R', R", and R'" are independently hydrogen, a C1 to C30 alkyl group, a C6 to C30 aryl group, or a C7 to C30 arylalkyl group), or a group represented by Chemical Formula 2:

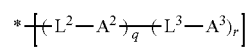

Chemical Formula 2 wherein, in Chemical Formula 2, $L^2$ and $L^3$ are independently O, CO, COO, C≡C, or $CONR^b$ (wherein $R^b$ is hydrogen or C1 to C30 alkyl group), $A^2$ and $A^3$ are independently a substituted or unsubstituted C6 to C30 aromatic ring, a substituted or unsubstituted fluorene ring, or a substituted or unsubstituted C7 to C20 arylalkyl group, q and r are independently an integer ranging from 0 to 3, m is an integer ranging from 0 to 3, and n is an integer ranging from 0 to 20.

The compound represented by Chemical Formula 1 according to an embodiment has an overall rigid planar structure, wherein each anhydride group at both sides of a core in the center is linked through a carbonyl group (C=O) to the core. It also includes a bulky substituent at a side chain of the core, and thus, may improve solubility due to a much higher molecular volume and an asymmetric structure, and in addition, may improve optical characteristics by decreasing a stacking structure and charge transfer among molecules.

The rigid planar structure has a much lower linear coefficient of thermal expansion, a high glass transition temperature, a high out-of-plane birefringence, high mechanical properties, and the like but may easily form an intermolecular stacking structure, and thus, form an intermolecular charge transfer complex, and accordingly, a polymer formed therefrom appears yellow and deteriorates optical properties.

The compound represented by Chemical Formula 1 according to the embodiment has a rigid planar structure overall but includes a bulky substituent at a side chain of a core, and thus, may reduce formation of an intermolecular complex and a charge transfer complex, and thus, reduce a deterioration of optical properties and simultaneously maintain high thermal stability, a low linear coefficient of thermal expansion, a high out-of-plane birefringence, and excellent mechanical properties due to the overall planar structure.

Accordingly, novel dianhydride including an ester structure in which a core including a bulky side chain is bonded with dianhydride groups at both sides of the core through a carbonyl group may be reacted with an aromatic diamine and the like to prepare a polyester-imide polymer, which may secure high thermal stability and excellent optical properties.

Furthermore, the compound according to the embodiment may be prepared from easily acquirable inexpensive starting materials, as shown through Examples that will be described later, and thus, may lower a preparation cost compared with conventional particularly expensive aromatic diamine or aromatic dianhydride showing excellent optical properties, mechanical properties, and the like.

In an exemplary embodiment, o and p of Chemical Formula 1 may independently be 0 or 1, $L^1$ may be O or $NR^b$ (wherein $R^b$ is hydrogen or a C1 to C20 alkyl group), for example, O or NH, $A^1$ may be a C6 to C30 aromatic organic group, for example, a C6 to C20 aromatic organic group, for example, a C6 to C12 aromatic organic group, for example, a C6 to C10 aromatic organic group, for example, a benzene ring, and $R^a$ may be hydrogen, a substituted or unsubstituted C1 to C20 alkyl group, a substituted or unsubstituted C1 to C20 alkoxy group, a substituted or unsubstituted C7 to C20 arylalkyl group, a halogen, —NR'R" (wherein R' and R" are independently hydrogen, a C1 to C30 alkyl group, a C6 to C30 aryl group, or a C7 to C30 arylalkyl group), —CO—NR'R" (wherein R' and R" are independently hydrogen, a C1 to C30 alkyl group, a C6 to C30 aryl group, or a C7 to C30 arylalkyl group), —SiR'R"R'" (wherein R', R", and R'" are independently hydrogen or a C1 to C20 alkyl group), or a group represented by Chemical Formula 2:

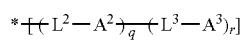

Chemical Formula 2 wherein, in Chemical Formula 2, $L^2$ and $L^3$ may independently be O, CO, COO, C≡C, or $CONR^b$ (wherein $R^b$ is hydrogen or a C1 to C20 alkyl group), for example, COO, C≡C, or $CONR^b$ (wherein $R^b$ is hydrogen or a C1 to C20 alkyl group), for example, COO, C≡C, or CONH, $A^2$ and $A^3$ may independently be a substituted or unsubstituted C6 to C20 aromatic ring group, for example, a substituted or unsubstituted C6 to C16 aromatic ring, for example, a substituted or unsubstituted C6 to C12 aromatic ring, for example, a benzene ring, a substituted or unsubstituted fluorene ring, or a substituted or unsubstituted C7 to C20 arylalkyl group, for example, a substituted or unsubstituted phenylalkyl group, for example, a phenylmethyl group, a phenylethyl group, a phenylpropyl group, a phenylbutyl group, or a phenylpentyl group, q and r may independently be an integer ranging from 0 to 2, provided that 1≤q+r≤2, m may be an integer ranging from 0 to 2, for example, 0 or 1, and n may be an integer of 0 to 10, for example, an integer of 0 to 5, for example, an integer of 0 to 3, for example, an integer of 0 to 2.

The monomer represented by Chemical Formula 1 may be a monomer represented by Chemical Formula 3 or Chemical Formula 4:

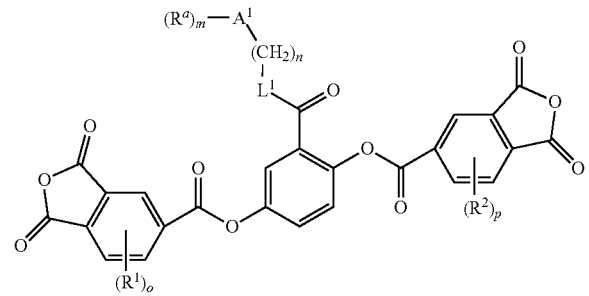

Chemical Formula 3

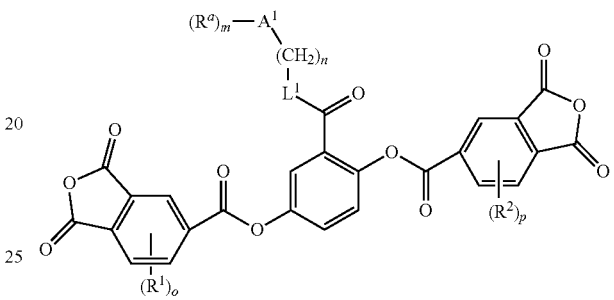

Chemical Formula 4 wherein, in Chemical Formula 3 and Chemical Formula 4, $R^1$ and $R^2$ may independently be a substituted or unsubstituted C1 C30 alkyl group, a substituted or unsubstituted C3 to C30 cycloalkyl group, a substituted or unsubstituted C1 to C30 alkoxy group, a substituted or unsubstituted C3 to C30 cycloalkoxy group, a substituted or unsubstituted C6 to C30 aryl group, a substituted or unsubstituted C2 to C30 acyl group, a hydroxy group, a halogen, a nitro group, —NR'R" (wherein R' and R" are independently hydrogen, a C1 to C30 alkyl group, or a C6 to C30 aryl group), —SiR'R"R'" (wherein R', R", and R'" are independently hydrogen or a C1 to C20 alkyl group), or combination thereof, o and p may independently be an integer ranging from 0 to 3, for example, may independently be 0 or 1, or for example, o and p may be all 0, $L^1$ may be O or $NR^b$ (wherein $R^b$ is hydrogen or a C1 to C20 alkyl group), for example, or O or NH, $A^1$ may be a C6 to C20 aromatic organic group, for example, a C6 to C16 aromatic organic group, for example, a C6 to C12 aromatic organic group, for example, a C6 to C10 aromatic organic group, for example, a benzene ring, $R^a$ may be hydrogen, a substituted or unsubstituted C1 to C30 alkyl group, a substituted or unsubstituted C1 to C30 alkoxy group, a substituted or unsubstituted C3 to C30 cycloalkyl group, a substituted or unsubstituted C3 to C30 cycloalkoxy group, a substituted or unsubstituted C6 to C30 aryl group, a substituted or unsubstituted C7 to C30 arylalkyl group, a hydroxy group, a halogen, a nitro group, —NR'R" (wherein R' and R" are independently hydrogen, a C1 to C30 alkyl group, a C6 to C30 aryl group, or a C7 to C30 arylalkyl group), —CO—NR'R" (wherein R' and R" are independently hydrogen, a C1 to C30 alkyl group, a C6 to C30 aryl group, or a C7 to C30 arylalkyl group), —SiR'R"R'" (wherein R', R", and R'" are independently hydrogen, a C1 to C30 alkyl group, a C6 to C30 aryl group, or a C7 to C30 arylalkyl group), or a group represented by Chemical Formula 2:

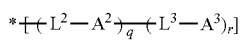

Chemical Formula 2 wherein, in Chemical Formula 2,

L² and L³ may independently be O, CO, COO, C≡C, or CONR^b (wherein R^b is hydrogen or a C1 to C20 alkyl group), for example, COO, C≡C, or CONR^b (wherein R^b is hydrogen or a C1 to C20 alkyl group), for example, COO, C≡C, or CONH, A² and A³ may independently be a substituted or unsubstituted C6 to C30 aromatic ring, for example, a substituted or unsubstituted C6 to C16 aromatic ring, for example, a substituted or unsubstituted C6 to C12 aromatic ring, for example, a substituted or unsubstituted C6 to C10 aromatic ring, for example, a benzene ring, a substituted or unsubstituted fluorene ring, for example, an unsubstituted fluorene ring, or a substituted or unsubstituted C7 to C30 arylalkyl group, for example, a substituted or unsubstituted phenylmethyl group, a substituted or unsubstituted phenylethyl group, a substituted or unsubstituted phenylpropyl group, a substituted or unsubstituted phenylbutyl group, or a substituted or unsubstituted phenylpentyl group, q and r may independently be an integer ranging from 0 to 3, for example, may independently be an integer ranging from 0 to 2, provided that 1≤q+r≤2, m may be an integer ranging from 0 to 3, for example, an integer ranging from 0 to 2, for example, 0 or 1, and n may be an integer ranging from 0 to 10, for example, an integer ranging from 0 to 5, for example, an integer ranging from 0 to 3, or for example, an integer ranging from 0 to 2.

In Chemical Formula 3 and Chemical Formula 4, o and p may independently be 0 or 1, for example, o and p may be all 0, and L¹ may be O or NR^b (wherein R^b is hydrogen or a C1 to C20 alkyl group), A¹ may be a C6 to C20 aromatic organic group, for example, a benzene ring, and R^a may be hydrogen, a substituted or unsubstituted C1 to C10 alkyl group, a substituted or unsubstituted C1 to C10 alkoxy group, a halogen, —CO—NR'R" (wherein R' and R" are independently hydrogen, a C1 to C30 alkyl group, a C6 to C30 aryl group, or a C7 to C30 arylalkyl group), or a group represented by Chemical Formula 2:

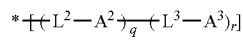

Chemical Formula 2 wherein, in Chemical Formula 2,

L² and L³ are independently COO, C≡C, or CONR^b (wherein R^b is hydrogen or a C1 to C20 alkyl group), A² and A³ are independently a substituted or unsubstituted benzene ring, a substituted or unsubstituted fluorene ring, or a substituted or unsubstituted C7 to C20 arylalkyl group, q and r are independently an integer ranging from 0 to 2, provided that 1≤q+r≤2, m is an integer of 0 or 1, and n is an integer of 0 to 5.

o and p of Chemical Formula 3 and Chemical Formula 4 may be all 0, L¹ may be O or NH, A¹ is a benzene ring, and R^a may be hydrogen, a fluorine group, —CO—NR'R" (wherein R' and R" are independently hydrogen, a C1 to C30 alkyl group, a C6 to C30 aryl group, or a C7 to C30 arylalkyl group), or a group represented by Chemical Formula 2:

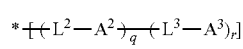

Chemical Formula 2 wherein, in Chemical Formula 2,

L² and L³ may independently be COO, C≡C, or CONH,

A² and A³ may independently be a benzene ring, a fluorene ring, or a C7 to C20 arylalkyl group, q and r may independently be an integer of 0 or 1, provided that 0≤q+r≤1, m may be an integer of 1.

Examples of the monomer according to an embodiment may be compounds represented by Compounds M-1 to M-20, but are not limited thereto:

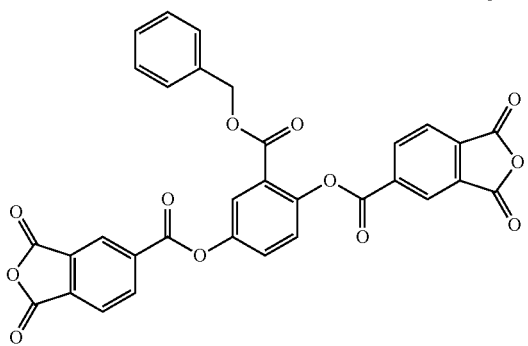

Compound M-1

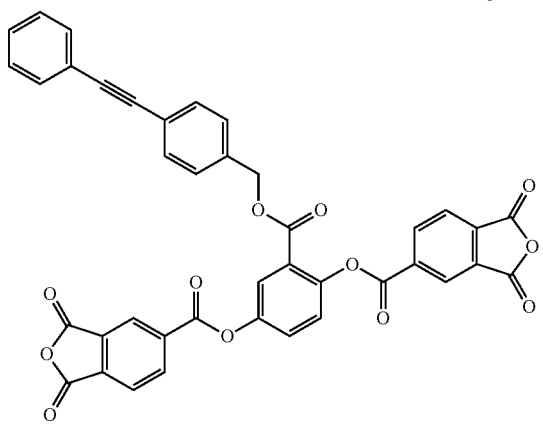

Compound M-2

-continued
Compound M-3
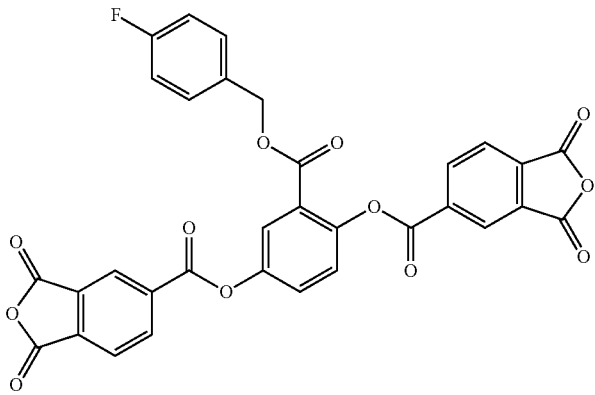
Compound M-4
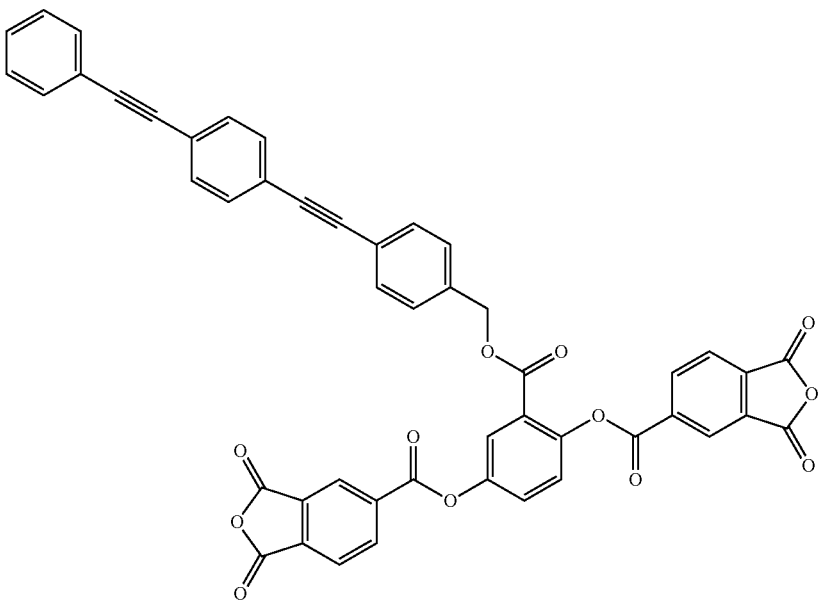
Compound M-5
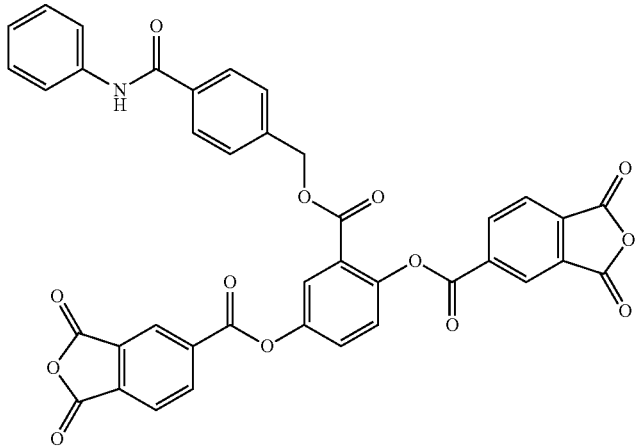

Compound M-6
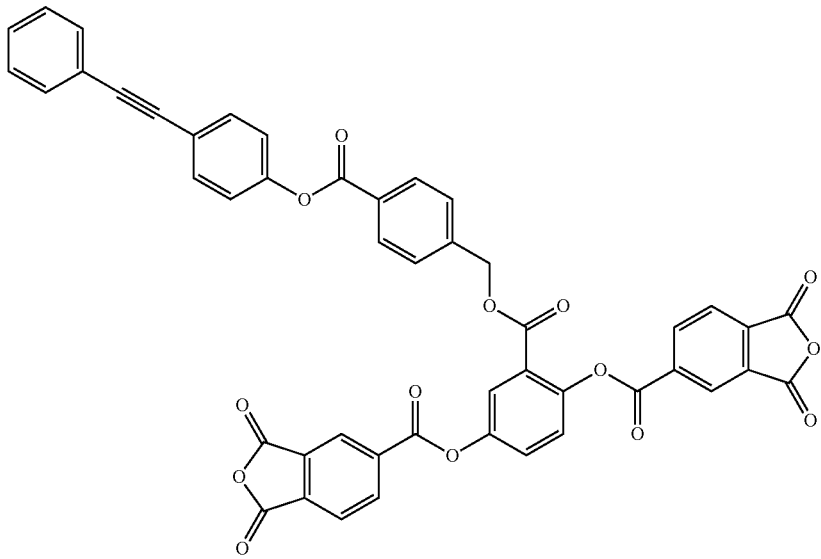
Compound M-7
Compound M-8
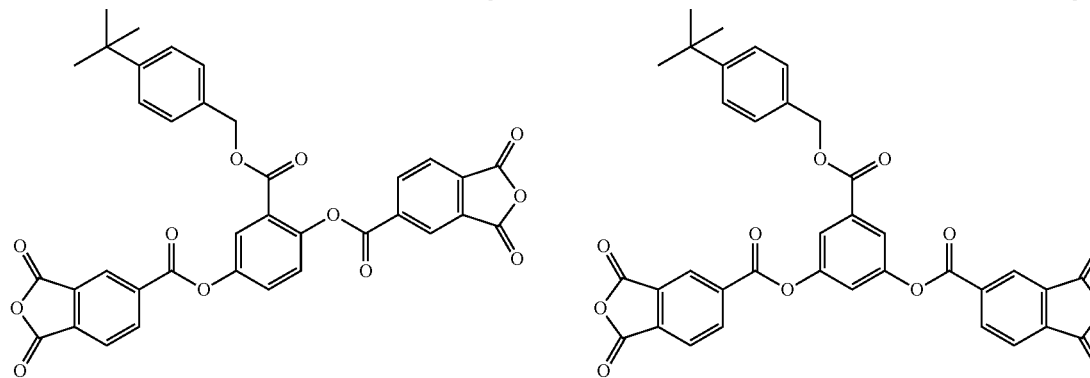
Compound M-9
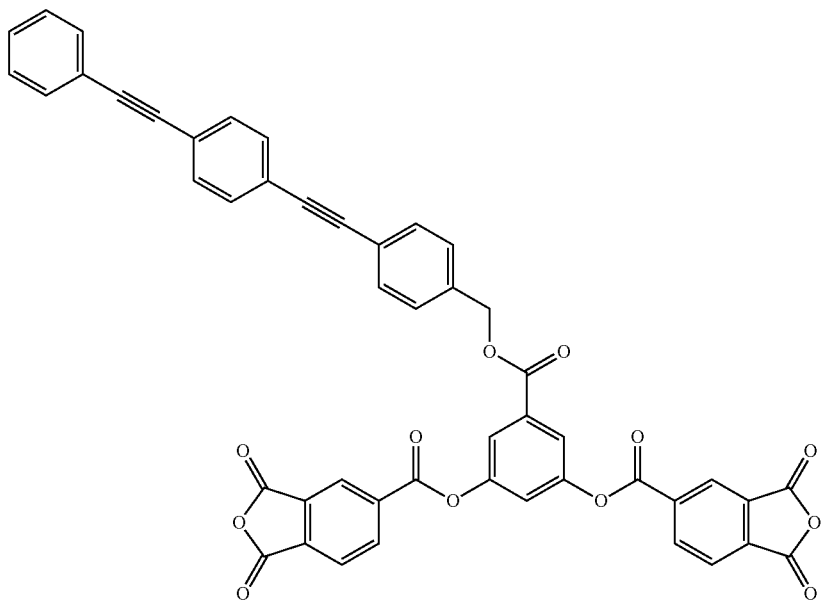

Compound M-10
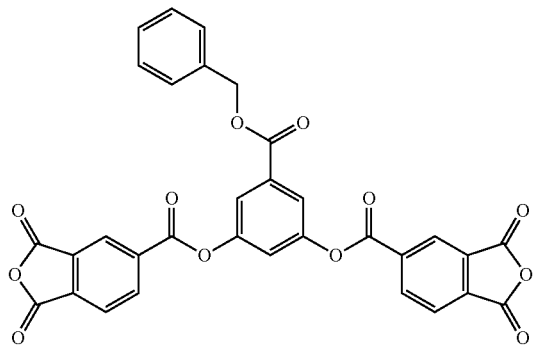
Compound M-11
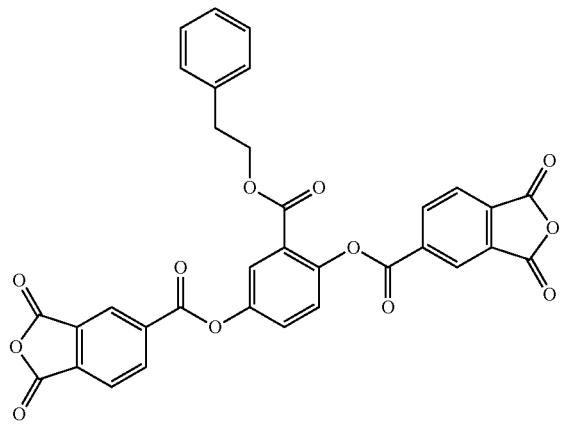
Compound M-12
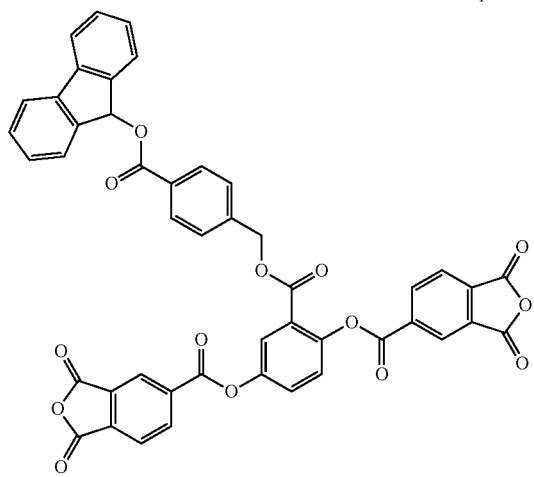
Compound M-13
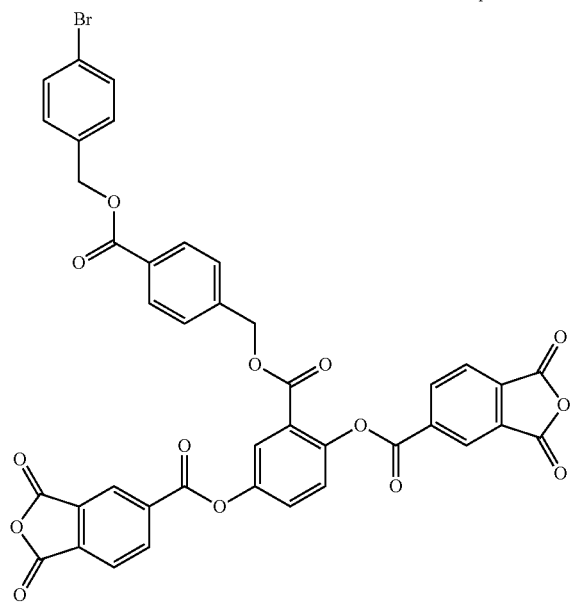
Compound M-14
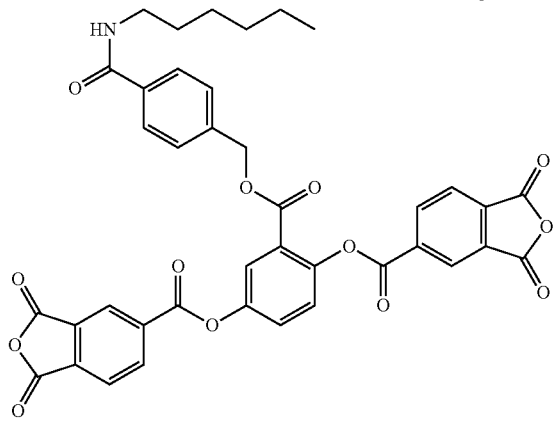
Compound M-15
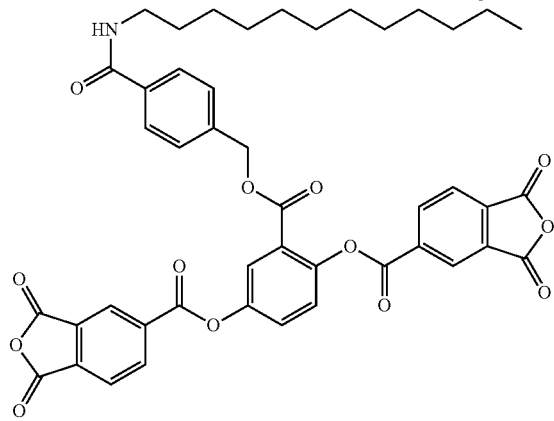

-continued
Compound M-16
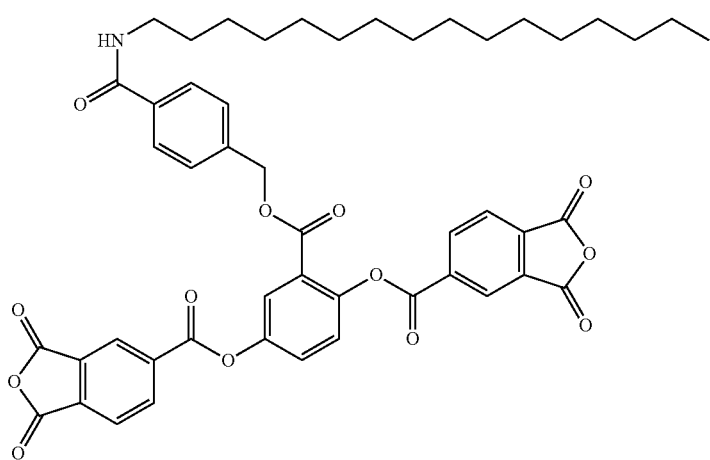
Compound M-17
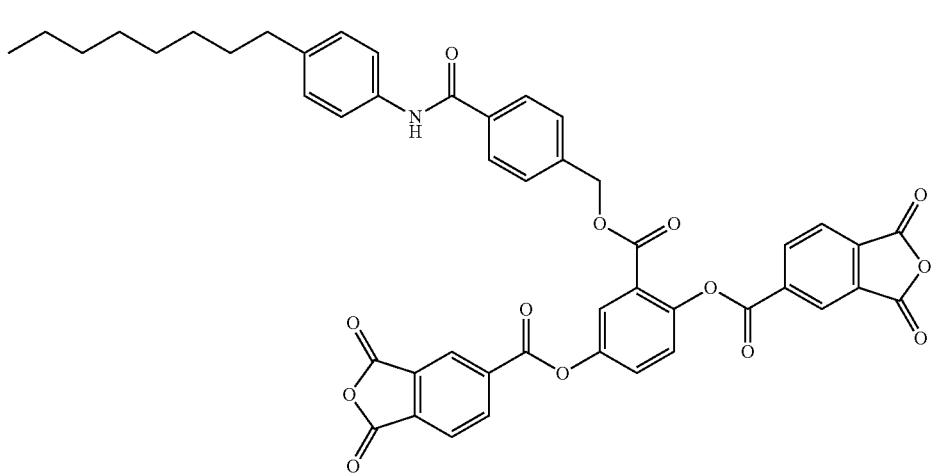
Compound M-18
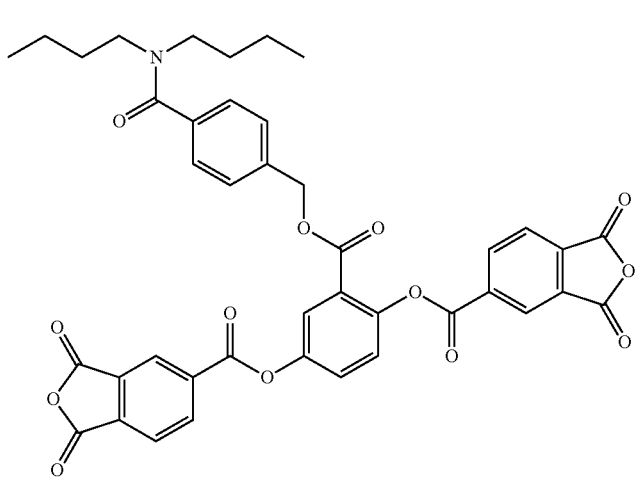

Compound M-19
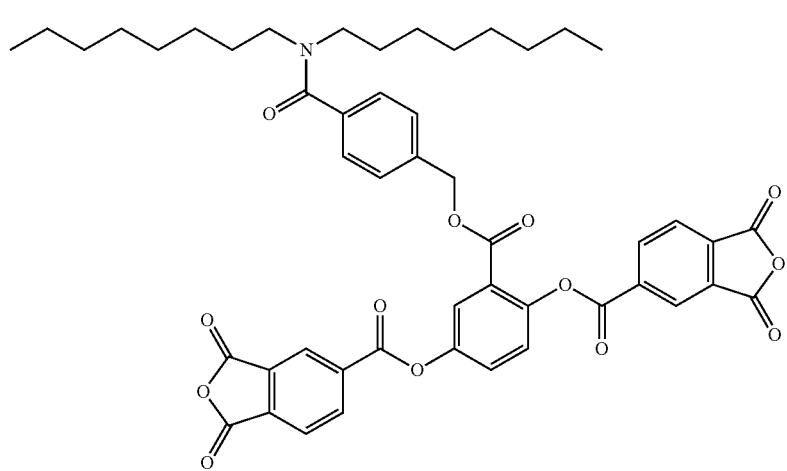
Compound M-20
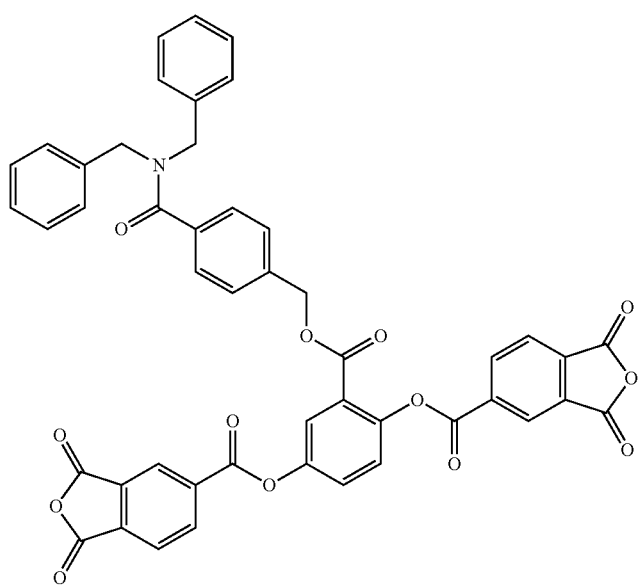
In an exemplary embodiment, among the monomers represented by Chemical Formula 3, the compound wherein $L^1$ is O, n is 1, and both o and p are 0 may be prepared according to Reaction Scheme 1:
-continued
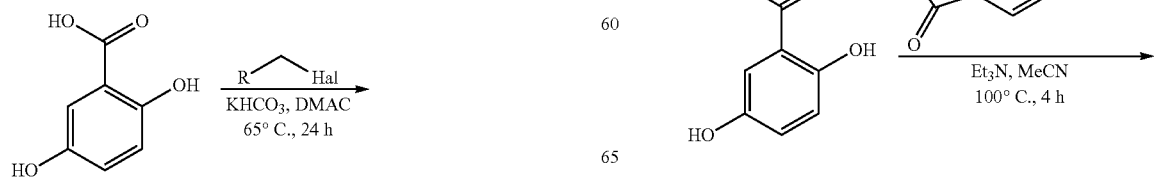

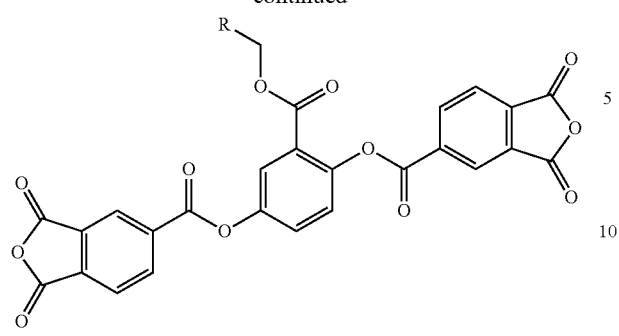

In an exemplary embodiment, among the monomer represented by Chemical Formula 4, the compound wherein $L^1$ is O, n is 1, and both o and p are 0 may be prepared according to Reaction Scheme 2:

Reaction Scheme 2

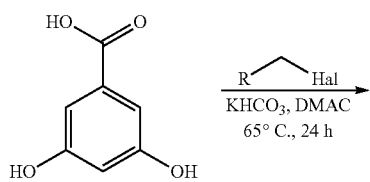

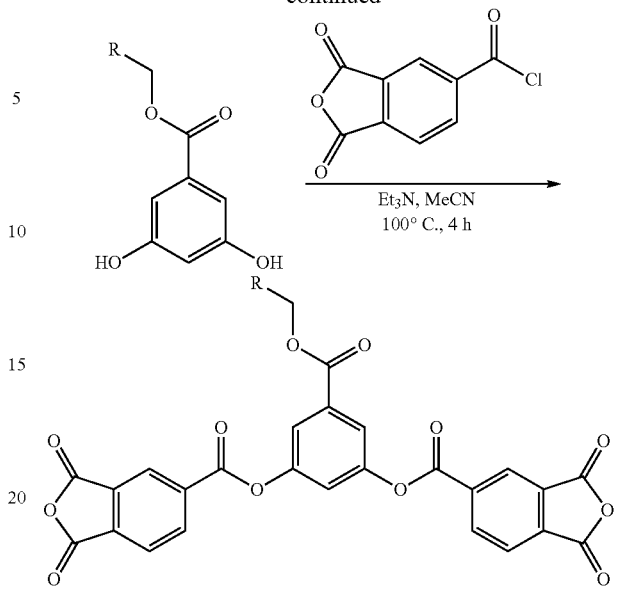

In Reaction Scheme 1 and Reaction Scheme 2, in "R—CH$_2$—Hal", "R—" corresponds to a moiety represented by "(R$^a$)m-A$^1$-" in Chemical Formulae 3 and 4, "Hal" refers to an halogen atom, for example, F, Cl, Br, or I, "DMAC" refers to a solvent "dimethyl acetamide", and "MeCN" refers to "methyl cyanide".

In an exemplary embodiment, among the monomers represented by Chemical Formula 3, a compound wherein $L^1$ is O or NH, n is 0 or 1, and p is equal to 0 may be prepared according to Reaction Scheme 3:

Reaction Scheme 3

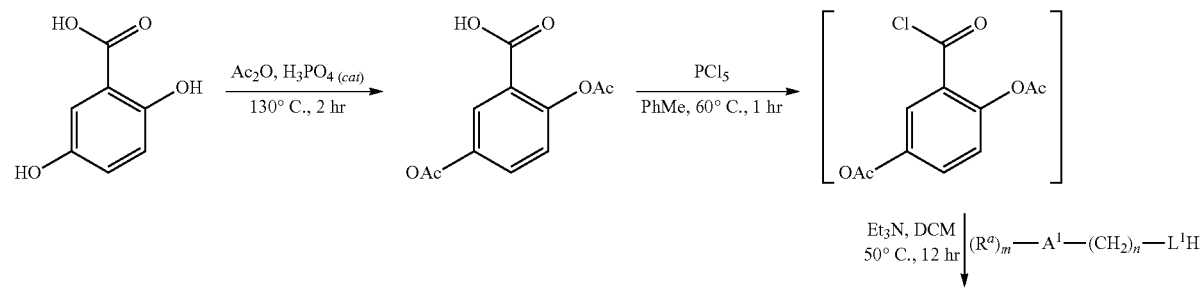

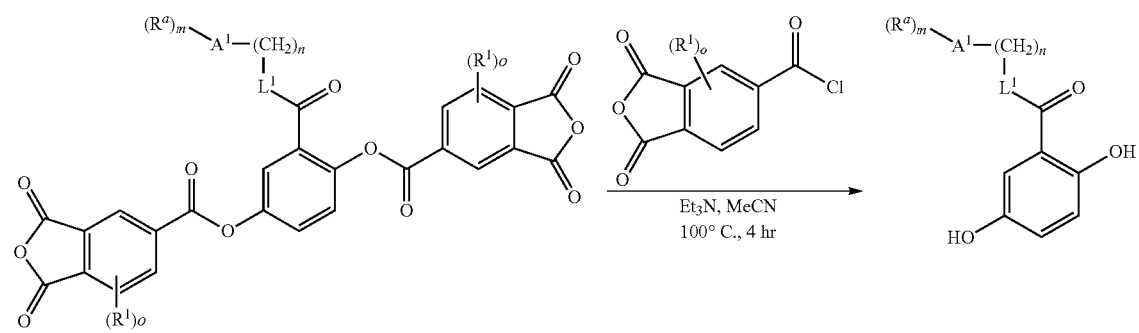

In an exemplary embodiment, among the monomers represented by Chemical Formula 4, a compound wherein $L^1$ is O or NH, n is 0 or 1, and p is equal to 0 may be prepared according to Reaction Scheme 4:

—CH(OH)—, —S(=O)$_2$—, —Si(CH$_3$)$_2$—, —(CH$_2$)$_p$— (wherein, 1≤p≤10), —(CF$_2$)$_q$— (wherein, 1≤q≤10), —C(CH$_3$)$_2$—, —C(CF$_3$)$_2$—, —C(=O)NH—, or a combination thereof.

Reaction Scheme 4

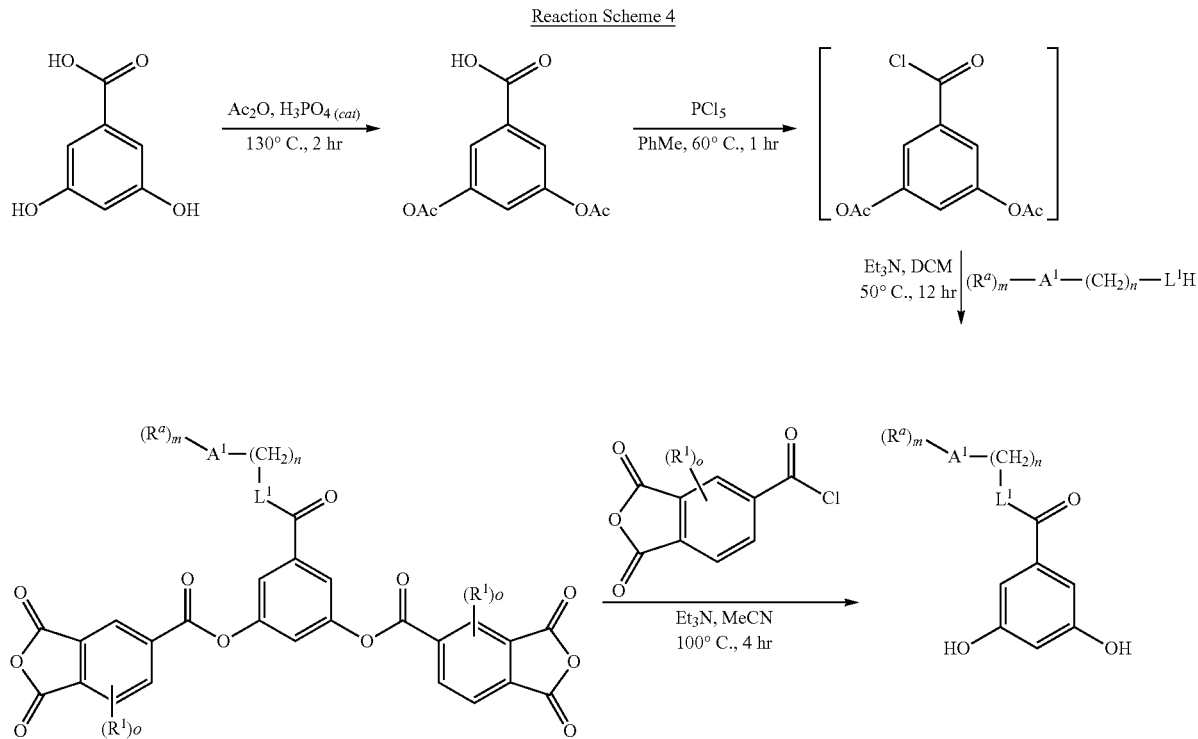

In Reaction Scheme 3 and Reaction Scheme 4, Ac$_2$O refers to acetic anhydride, OAc refers to an acetate group, PhMe refers to toluene, DCM refers to dichloromethane, and $R^a$, $A^1$, $L^1$, m, n, $R^1$, and o are the same as defined in Chemical Formula 3 and Chemical Formula 4.

In other words, the monomer according to an embodiment may be easily prepared according to Reaction Scheme by using commercially available inexpensive starting materials by a person having an ordinary skill in this art.

The monomer is a dianhydride compound having two anhydride groups at both ends and accordingly, reacts with a diamine compound in the same mole amount and forms polyimide.

Accordingly, in another embodiment, a polymer may be a product of reactants including the monomer according to an embodiment and diamine.

The diamine may be represented by Chemical Formula 5:

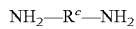 Chemical Formula 5

In Chemical Formula 5, $R^c$ is a substituted or unsubstituted C6 to C30 aromatic organic group, wherein the substituted or unsubstituted C6 to C30 aromatic organic group is present as a substituted or unsubstituted single aromatic ring; a fused ring including two or more the substituted or unsubstituted aromatic rings; or a ring system including two or more of the substituted or unsubstituted single aromatic ring and/or the fused ring that are linked by a single bond, or a functional group selected from a fluorenylene group, a substituted or unsubstituted C1 to C10 cycloalkylene group, a substituted or unsubstituted C6 to C15 arylene group, —O—, —S—, —C(=O)—, The polymer prepared by reacting the monomer according to an embodiment and the diamine represented by Chemical Formula 5 may include a first imide structural unit represented by Chemical Formula 13:

Chemical Formula 13

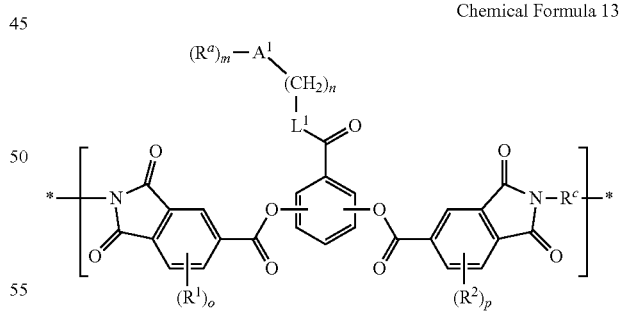

wherein, in Chemical Formula 13, $R^a$, $A^1$, $L^1$, m, n, $R^1$, $R^2$, O, and p are the same as defined in Chemical Formula 1 and $R^c$ is the same as defined in Chemical Formula 5.

When the monomer according to an embodiment is a monomer represented by Chemical Formula 3, the first imide structural unit may be represented by Chemical Formula 14:

Chemical Formula 14

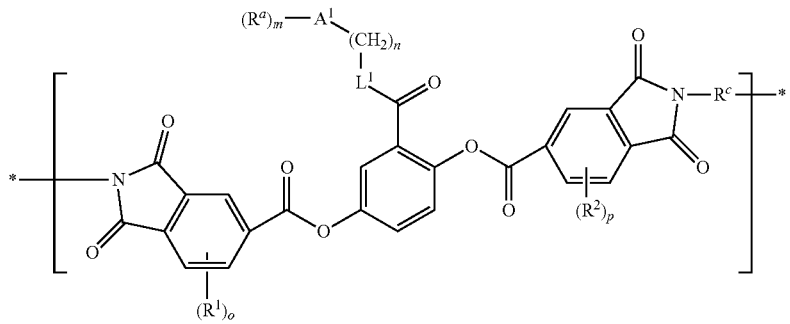

When the monomer according to an embodiment is a monomer represented by Chemical Formula 4, the first imide structural unit may be represented by Chemical Formula 15:

Chemical Formula 15

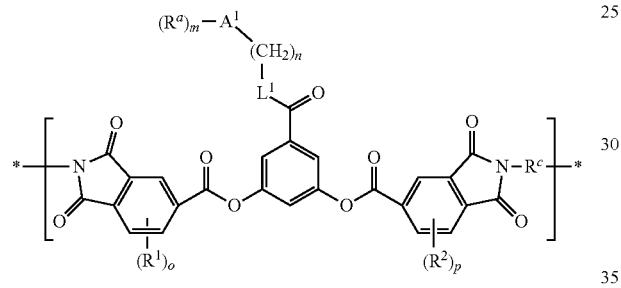

In Chemical Formula 14 and Chemical Formula 15, $R^a$, $A^1$, $L^1$, m, n, $R^1$, $R^2$, o, and p are the same as defined in Chemical Formula 1 and $R^c$ is the same as defined in Chemical Formula 5.

The diamine represented by Chemical Formula 5 may be represented by at least one of Chemical Formula 6 to Chemical Formula 8:

Chemical Formula 6

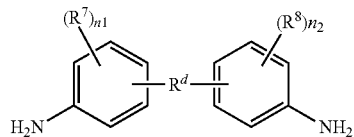

In Chemical Formula 6,
$R^d$ is selected from the following chemical formulae:

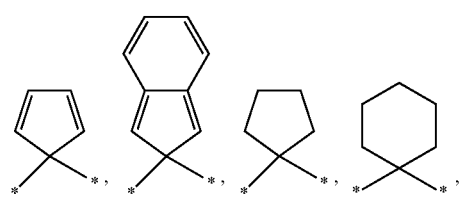

-continued

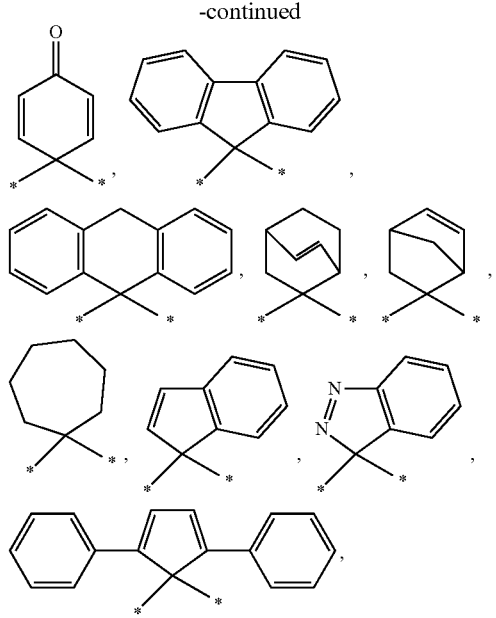

$R^7$ and $R^8$ are the same or different and are independently a halogen, a hydroxy group, an alkoxy group (—$OR^{200}$, wherein $R^{200}$ is a C1 to C10 aliphatic organic group), a silyl group (—$SiR^{201}R^{202}R^{203}$, wherein $R^{201}$, $R^{202}$, and $R^{203}$ are the same or different and are independently hydrogen, or a C1 to C10 aliphatic organic group), a substituted or unsubstituted C1 to C10 aliphatic organic group, or a substituted or unsubstituted C6 to C20 aromatic organic group, and n1 and n2 are independently an integer ranging from 0 to 4;

Chemical Formula 7

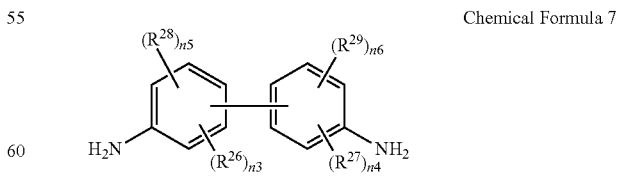

wherein, in Chemical Formula 7,
$R^{26}$ and $R^{27}$ are the same or different and are independently an electron withdrawing group selected from —$CF_3$, —$CCl_3$, —$CBr_3$, —$Cl_3$, —$NO_2$, —$CN$, —$COCH_3$, or —$CO_2C_2H_5$, $R^{28}$ and $R^{29}$ are the same or different and are independently a halogen, a hydroxy group, an alkoxy group (—$OR^{204}$, wherein $R^{204}$ is a C1 to C10 aliphatic organic group), a silyl group (—$SiR^{205}R^{206}R^{207}$, wherein $R^{205}$, $R^{206}$, and $R^{207}$ are the same or different and are independently hydrogen, or a C1 to C10 aliphatic organic group), a substituted or unsubstituted C1 to C10 aliphatic organic group, or a substituted or unsubstituted C6 to C20 aromatic organic group, n3 is an integer ranging from 1 to 4, n5 is an integer ranging from 0 to 3, and n3+n5 is an integer ranging from 1 to 4, n4 is an integer ranging from 1 to 4, n6 is an integer ranging from 0 to 3, and n4+n6 is an integer ranging from 1 to 4;

Chemical Formula 8

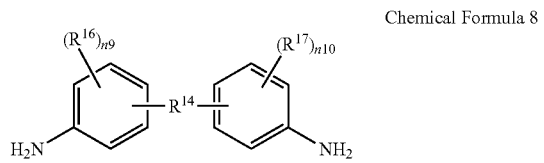

wherein, in Chemical Formula 8, $R^{14}$ is O, S, C(=O), CH(OH), S(=O)$_2$, Si(CH$_3$)$_2$, (CH$_2$)$_p$ (wherein, 1≤p≤10), (CF$_2$)$_q$ (wherein, 1≤q≤10), C(CH$_3$)$_2$, C(CF$_3$)$_2$, C(=O)NH, or a substituted or unsubstituted C6 to C18 aromatic organic group, wherein the C6 to C18 aromatic organic group is present as a single aromatic ring, a fused ring including two or more aromatic rings, or a ring system including two or more of the single aromatic ring and/or the fused ring that are linked by a single bond, or a functional group selected from a fluorenylene group, O, S, C(=O), CH(OH), S(=O)$_2$, Si(CH$_3$)$_2$, (CH$_2$)$_p$ (wherein, 1≤p≤10), (CF$_2$)$_q$ (wherein, 1≤q≤10), C(CH$_3$)$_2$, C(CF$_3$)$_2$, or C(=O)NH, $R^{16}$ and $R^{17}$ are the same or different and are independently a halogen, a hydroxy group, an alkoxy group (—$OR^{212}$, wherein $R^{212}$ is a C1 to C10 aliphatic organic group), a silyl group (—$SiR^{213}R^{214}R^{215}$, wherein $R^{213}$, $R^{214}$, and $R^{215}$ are the same or different and are independently hydrogen or a C1 to C10 aliphatic organic group), a substituted or unsubstituted C1 to C10 aliphatic organic group, or a substituted or unsubstituted C6 to C20 aromatic organic group, and n9 and n10 are independently an integer ranging from 0 to 4.

The polymer according to an embodiment may be a product of reactants including at least one of the diamine represented by Chemical Formula 7 and the diamine represented by Chemical Formula 8, wherein the diamine represented by Chemical Formula 7 includes 2,2'-bis(trifluoromethyl)benzidine (TFDB) and the diamine represented by Chemical Formula 8 includes 4,4'-diaminodiphenyl sulfone (DADPS).

When the polymer according to an embodiment is prepared by reacting the monomer represented by Chemical Formula 1 with TFDB as diamine, the first imide structural unit may include a structural unit represented by Chemical Formula 16:

Chemical Formula 16

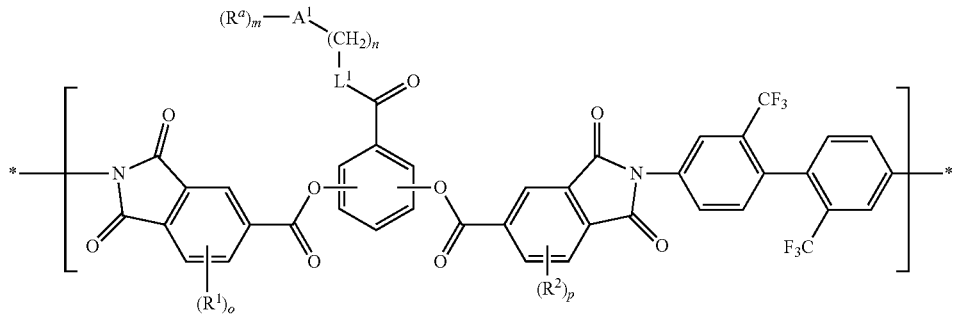

When the polymer according to an embodiment is prepared by reacting the monomer represented by Chemical Formula 1 with DADPS as diamine, the first imide structural unit may include a structural unit represented by Chemical Formula 17:

Chemical Formula 17

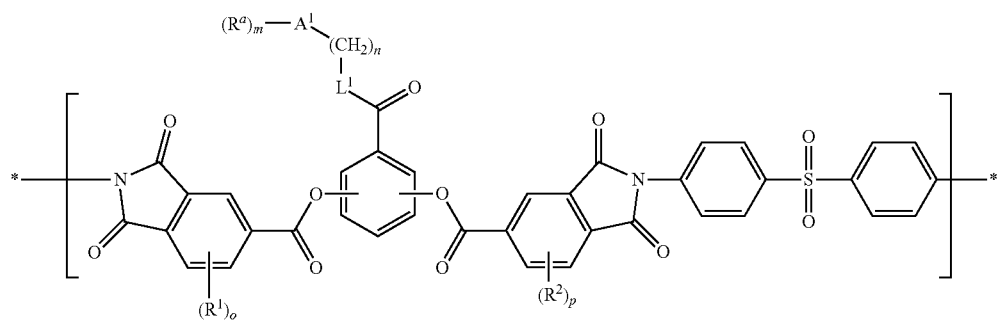

In Chemical Formula 16 and Chemical Formula 17, $R^a$, $A^1$, $L^1$, m, n, $R^1$, $R^2$, o and p are the same as defined in Chemical Formula 1.

The polymer according to an embodiment may be a product of reactants including a compound represented by Chemical Formula 9 as a dianhydride compound in addition to the monomer represented by Chemical Formula 1 according to an embodiment:

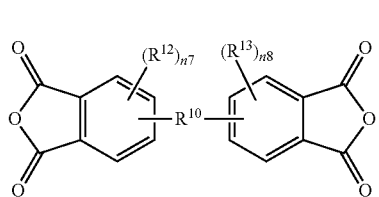

Chemical Formula 9 wherein, in Chemical Formula 9, $R^{10}$ is a single bond, —O—, —S—, —C(=O)—, —CH(OH)—, —C(=O)NH—, —S(=O)$_2$—, —Si(CH$_3$)$_2$—, —(CH$_2$)$_p$—, —(CF$_2$)$_q$—, —C(C$_n$H$_{2n+1}$)$_2$—, —C(C$_n$F$_{2n+1}$)$_2$—, —(CH$_2$)$_p$—C(C$_n$H$_{2n+1}$)$_2$—(CH$_2$)$_q$—, or —(CH$_2$)$_p$—C(C$_n$F$_{2n+1}$)$_2$—(CH$_2$)$_q$— (wherein 1≤n≤10, 1≤p≤10, and 1≤q≤10), $R^{12}$ and $R^{13}$ are independently a halogen, a hydroxy group, a substituted or unsubstituted C1 to C10 aliphatic organic group, a substituted or unsubstituted C6 to C20 aromatic organic group, a —OR$^{201}$ group (wherein R$^{201}$ is a C1 to C10 aliphatic organic group), or a —SiR$^{210}$R$^{211}$R$^{212}$ (wherein R$^{210}$, R$^{211}$, and R$^{212}$ are independently hydrogen or a C1 to C10 aliphatic organic group) group, and n7 and n8 are independently one of integers of 0 to 3.

The dianhydride represented by Chemical Formula 9 may include dianhydride represented by Chemical Formula 10, dianhydride represented by Chemical Formula 11, or a combination thereof:

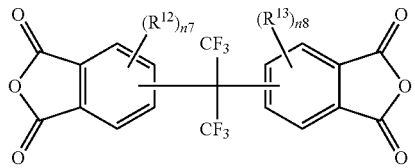

Chemical Formula 10

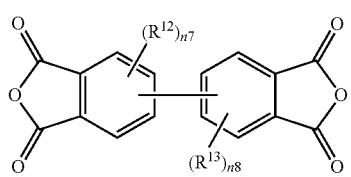

Chemical Formula 11 wherein, in Chemical Formula 10 and Chemical Formula 11, $R^{12}$ and $R^{13}$ are the same or different and are independently a halogen, a hydroxy group, an alkoxy group (—OR$^{208}$, wherein R$^{208}$ is a C1 to C10 aliphatic organic group), a silyl group (—SiR$^{209}$R$^{210}$R$^{211}$, wherein R$^{209}$, R$^{210}$, and R$^{211}$ are the same or different and are independently hydrogen or a C1 to C10 aliphatic organic group), a substituted or unsubstituted C1 to C10 aliphatic organic group, or a substituted or unsubstituted C6 to C20 aromatic organic group, and n7 and n8 are independently an integer ranging from 0 to 3.

When the polymer according to an embodiment is a product of reactants that further includes the dianhydride represented by Chemical Formula 9, the polymer may further include a second imide structural unit represented by Chemical Formula 18:

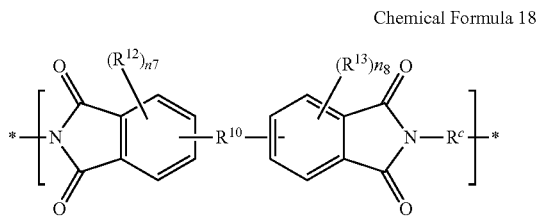

Chemical Formula 18 wherein, in Chemical Formula 18, $R^{10}$, $R^{12}$, $R^{13}$, n7, and n8 are the same as defined in Chemical Formula 9 and $R^c$ is the same as defined in Chemical Formula 5.

The second imide structural unit represented by Chemical Formula 18 may include a structural unit represented by Chemical Formula 19, a structural unit represented by Chemical Formula 20, or a combination thereof:

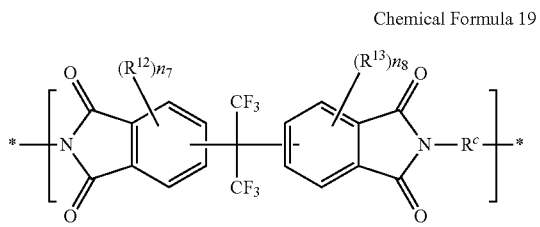

Chemical Formula 19

Chemical Formula 20 wherein, in Chemical Formula 19 and Chemical Formula 20, $R^{12}$, $R^{13}$, n7, and n8 are the same as defined in Chemical Formula 9 and $R^c$ is the same as defined in Chemical Formula 5.

The polymer according to an embodiment may be a product of reactants that further include a dicarboxylic acid derivative represented by Chemical Formula 12:

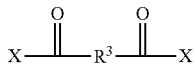

Chemical Formula 12 wherein, in Chemical Formula 12, $R^3$ is at least one of a substituted or unsubstituted phenylene group and a substituted or unsubstituted biphenylene group, and X's are independently the same or different halogen atom.

In Chemical Formula 12, $R^3$ may be at least one of an unsubstituted phenylene group and an unsubstituted biphenylene group, and X's may independently be Cl or Br.

When the polymer according to an embodiment is a product of reactants that further includes the dicarboxylic acid derivative represented by Chemical Formula 12, the dicarboxylic acid derivative may react with the diamine represented by Chemical Formula 5 to form an amide structural unit represented by Chemical Formula 21:

Chemical Formula 21

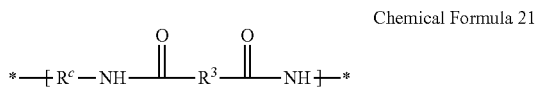

In Chemical Formula 21, $R^c$ is the same as defined in Chemical Formula 5 and $R^3$ is the same as defined in Chemical Formula 12.

In an exemplary embodiment, the polymer according to the embodiment is a product of reactants including TFDB as diamine and terephthaloyl chloride (TPCl) wherein $R^3$ is a phenylene group and X is Cl as the dicarboxylic acid derivative represented by Chemical Formula 3, and the structural unit represented by Chemical Formula 21 may include a structural unit represented by Chemical Formula 22:

Chemical Formula 22

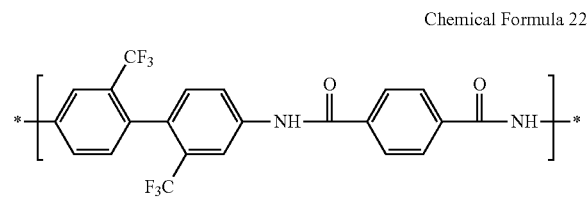

In an exemplary embodiment, the polymer according to the embodiment is a product of reactants including DADPS as diamine and terephthaloyl chloride (TPCl) wherein $R^3$ is a phenylene group and X is Cl as the dicarboxylic acid derivative represented by Chemical Formula 3, and the structural unit represented by Chemical Formula 21 may include a structural unit represented by Chemical Formula 23:

Chemical Formula 23

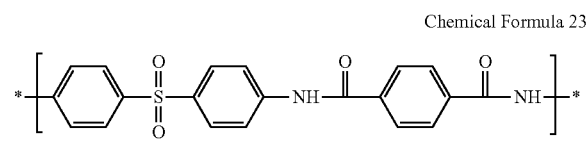

The polymer may be a product of reactants including the monomer according to an embodiment, for example, the monomer represented by Chemical Formula 3, the monomer represented by Chemical Formula 4, or a combination thereof and the dianhydride represented by Chemical Formula 9, for example, the dianhydride represented by Chemical Formula 10, the dianhydride represented by Chemical Formula 11, or a combination thereof in a mole ratio of about 90:10 to about 10:90, for example, a mole ratio of about 85:15 to about 15:85, for example, a mole ratio of about 20:80 to about 80:20, for example, a mole ratio of about 25:75 to about 75:25, for example, a mole ratio of about 30:70 to about 70:30, for example, a mole ratio of about 35:65 to about 65:35, for example, a mole ratio of about 40:60 to about 60:40, for example, a mole ratio of about 45:55 to about 55:45, for example a mole ratio of about 50:50.

A polyimide-based polymer having desired optical properties and high heat resistance may be prepared by appropriately adjusting a ratio of the monomer according to an embodiment and dianhydride represented by Chemical Formula 9.

The polymer may be for example formed as a film, and thus, used as a polymer film. The polymer film may be for example transparent, and thus, used for any use requiring transparency. The polymer film may be for example used for various uses such as a substrate, a protective film, a compensation film, an optical film, a dielectric layer, an insulation layer, an adhesive layer, and the like.

Hereinafter, a compensation film according to an embodiment is described.

A compensation film according to an embodiment includes the polymer.

That is, the compensation film according to an embodiment may include a polyimide-based polymer including a first imide structural unit represented by Chemical Formula 13, such as, at least one of Chemical Formulae 14 to 17 prepared by reacting the monomer according to an embodiment, that is, the monomer represented by Chemical Formula 1 with a diamine.

Or, the compensation film may further include a polyimide-based polymer that is a product of reactants including an additional dianhydride, the dianhydride represented by Chemical Formula 9 in addition to the monomer represented by Chemical Formula 1 and the polymer may further include a second imide structural unit represented by at least one of Chemical Formula 18, such as, at least one of Chemical Formulae 19, and 20 in addition to the first imide structural unit.

Furthermore, the compensation film may include a poly (amide-imide) polymer that is a product of reactants further including the dicarboxylic acid derivative represented by Chemical Formula 12 and the polymer may further include an amide structural unit represented by Chemical Formula 21, such as, at least one of Chemical Formulae 22 and 23 in addition to the first imide structural unit.

In an exemplary embodiment, the compensation film may include a poly(amide-imide) copolymer including all of a first imide structural unit represented by Chemical Formula 13, such as, at least one of Chemical Formulae 14 to 17, a second imide structural unit represented by Chemical Formula 18, such as, at least one of Chemical Formulae 19 and 20, and an amide structural unit represented by Chemical Formula 21, such as, at least one of Chemical Formulae 22 and 23.

A polymer according to an embodiment may include, if necessary, a structural unit that is a reaction product of additional non-limiting monomers, dianhydride, diamine, and/or, dicarboxylic acid derivatives, along with the first imide structural unit in addition to the structural unit. The additional monomers, dianhydride, diamine and/or dicarboxylic acid derivatives, have no particular limit, but may be used along with any other kinds which may reinforce a function of an article manufactured from a polymer or a copolymer formed thereof, for example, an optical film, for example, a compensation film.

A film formed of the polymer according to an embodiment may have high thermal stability, for example, a high glass transition temperature of greater than or equal to about 150° C., for example, greater than or equal to about 160° C., for example, greater than or equal to about 170° C., for example, greater than or equal to about 180° C., for example, greater than or equal to about 190° C., for example, greater than or equal to about 200° C., for example, greater than or equal to about 210° C., for example, greater than or equal to about 220° C., for example, greater than or equal to about 230° C., for example, greater than or equal to about 240° C., and for example, greater than or equal to about 250° C.

In addition, the film formed of the polymer according to an embodiment may have excellent optical characteristic, for example, high light transmittance at about 450 nanometers (nm), for example, transmittance of greater than or equal to about 85 percent (%), for example, greater than or equal to about 86%, for example, greater than or equal to about 87%, for example, greater than or equal to about 88%, for example, greater than or equal to about 89%, and for example, greater than or equal to about 90%.

In addition, the film formed of the polymer according to an embodiment may have a high out-of-plane birefringence, for example, greater than or equal to about 0.03, for example, greater than or equal to about 0.04, for example, greater than or equal to about 0.05, for example, greater than or equal to about 0.06, for example, greater than or equal to about 0.07, for example, greater than or equal to about 0.08, for example, greater than or equal to about 0.09 at a thin film thickness of less than or equal to about 100 micrometers (μm), for example, less than or equal to about 90 μm, for example, less than or equal to about 80 μm, for example, less than or equal to about 70 μm, for example, less than or equal to about 60 μm, for example, less than or equal to about 50 μm, for example, less than or equal to about 40 μm, for example, less than or equal to about 30 μm, for example, less than or equal to about 20 μm.

In other words, the film formed of the polymer according to an embodiment shows high thermal stability, for example, a high glass transition temperature and excellent optical characteristics, for example, high light transmittance and high out-of-plane birefringence at 450 nm, particularly, a high out-of-plane birefringence at a thin film thickness of less than or equal to about 100 μm, and thus, may be used as an optical film such as a compensation film and the like.

When the film is used as a compensation film, the compensation film may have a predetermined retardation by changing light absorption characteristics depending on a refractive index and a wavelength.

A retardation (R) of the compensation film may be represented by an in-plane retardation ($R_o$) and a thickness direction retardation ($R_{th}$). The in-plane retardation ($R_o$) of compensation film is a retardation generated in in-plane of the compensation film and may be represented by $R_o=(n_x-n_y)d$. The thickness direction retardation ($R_{th}$) of the compensation film is a retardation generated in a thickness direction of the compensation film and may be represented by $R_{th}=\{[(n_x+n_y)/2]-n_z\}d$. Herein, $n_x$ is a refractive index in a direction having a highest in-plane refractive index in a plane of the compensation film (hereinafter, referred to as a 'slow axis'), $n_y$ is a refractive index in a direction having a lowest in-plane refractive index in a plane of the compensation film (hereinafter, referred to as a 'fast axis'), $n_z$ is a refractive index in a direction perpendicular to the slow axis and the fast axis of the compensation film, and d is a thickness of the compensation film.

The compensation film may have predetermined in-plane retardation and thickness direction retardation by changing the $n_x$, $n_y$, $n_z$, and/or thickness (d).

The retardation of the compensation film may be the same or different depending on a wavelength.

For example, the compensation film may have a forward wavelength dispersion retardation wherein a retardation about light at a short wavelength is larger than a retardation about light at a long wavelength. When a 550 nm wavelength is a reference wavelength, for example retardations (R) at 450 nm, 550 nm, and 650 nm wavelengths of the compensation film may satisfy Relationship Equation 1 or 2.

$$R(450\ nm) \geq R(550\ nm) \geq R(650\ nm) \quad \text{Relationship Equation 1}$$

$$R(450\ nm) \geq_R (550\ nm) \geq_R (650\ nm) \quad \text{Relationship Equation 2}$$

For example, the compensation film may have a flat wavelength dispersion retardation wherein a retardation about light at a long wavelength is substantially equivalent to a retardation about light at a short wavelength and retardations (R) at 450 nm, 550 nm, and 650 nm wavelengths of the compensation film may satisfy Relationship Equation 3.

$$R(450\ nm) = R(550\ nm) = R(650\ nm) \quad \text{Relationship Equation 3}$$

For example, the compensation film may have a reverse wavelength dispersion retardation wherein a retardation about light at a long wavelength is larger than a retardation about light at a short wavelength and for example retardations (R) at 450 nm, 550 nm, and 650 nm wavelengths of the compensation film may satisfy Relationship Equation 4 or 5.

$$R(450\ nm) \leq R(550\ nm) \leq R(650\ nm) \quad \text{Relationship Equation 4}$$

$$R(450\ nm) < R(550\ nm) \leq R(650\ nm) \quad \text{Relationship Equation 5}$$

In Relationship Equations 1 to 5,

R(450 nm) is an in-plane retardation or a thickness direction retardation of the compensation film at a 450 nm wavelength, R(550 nm) is an in-plane retardation or a thickness direction retardation of the compensation film at a 550 nm wavelength, and R(650 nm) is an in-plane retardation or a thickness direction retardation of the compensation film at a 650 nm wavelength.

The compensation film may be adjusted to have a desired retardation depending on a wavelength.

The compensation film may have high birefringence, and thus, a relatively thin thickness. The compensation film may have, for example, a thickness of about 3 μm to about 200 μm, within the range, a thickness of about 5 μm to about 150 μm, and within the range, a thickness of about 5 μm to about 100 μm.

The compensation film includes a substantially transparent polymer, and thus, may be used as a substrate, and accordingly, a separate substrate beneath the compensation film may be omitted. Accordingly, a thickness of the compensation film may be further reduced. Accordingly, the compensation film may be effectively applied to a flexible display device such as a foldable display device or a bendable display device, and thus, improve optical properties and display characteristics.

The compensation film may be formed, for example, through preparation of the monomer according to an embodiment, polymerization of the monomer into a polymer, formation of the polymer into a polymer film, and elongation of the polymer film.

The polymer film may be elongated, for example, at an elongation rate of about 110% to about 1,000% at about 50° C. to about 500° C. Herein, the elongation rate indicates a length ratio after and before the elongation, that is, a degree of length increase of the polymer film after elongation in a uniaxial direction. For example, the polymer film may be elongated in a uniaxial direction.

The compensation film may be used alone or along with other compensation films.

The compensation film may be used with a polarizer and may be used as an optical film to prevent reflection of external light of a display device. The optical film may be for example an anti-reflective film, but is not limited thereto.

Figure 2:
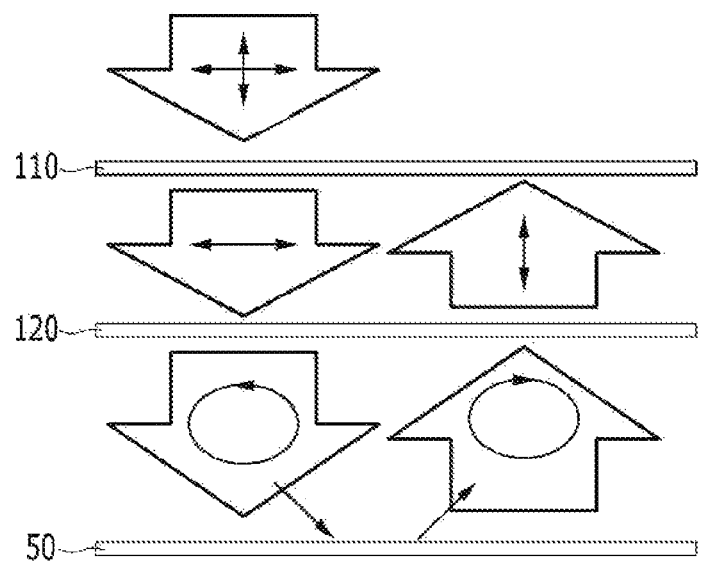
FIG. 2 is a schematic view showing the external light anti-reflection principle of an optical film.
Figure 3:
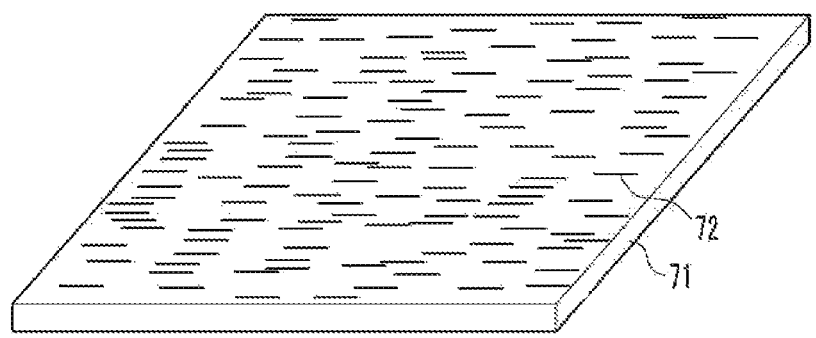
FIG. 3 is a schematic view showing an embodiment of a polarizing film.

FIG. 1 is a schematic cross-sectional view of an optical film according to an embodiment, FIG. 2 is a schematic view showing the external light anti-reflection principle of an optical film, and FIG. 3 is a schematic view showing an embodiment of a polarizing film.

Referring to FIG. 1, an optical film 100 according to an embodiment includes a polarizer 110 and a compensation film 120. The compensation film 120 may circularly polarize light passing the polarizer 110 to generate retardation and may have an effect on reflection and/or absorption of light.

For example, the optical film 100 may be formed on one surface or both surfaces of a display device and particularly on the screen side of the display device, and thus, may prevent reflection of light inflowing from the outside (hereinafter referred to as "external light"). Accordingly, visibility deterioration due to reflection of external light may be prevented.

FIG. 2 is a schematic view showing the external light anti-reflection principle of an optical film.

Referring to FIG. 2, while the incident unpolarized light having entered from the outside is passed through the polarizer 110, only a first polarized perpendicular component, which is one polarized perpendicular component of two polarized perpendicular components, is transmitted, and the polarized light is shifted into circularly polarized light by passing through the compensation film 120. While the circularly polarized light is reflected in a display panel 50 including a substrate, an electrode, and so on, and changes to the circular polarization direction, and the circularly polarized light is passed through the compensation film 120 again, only a second polarized perpendicular component, which is the other polarized perpendicular component of the two polarized perpendicular components, may be transmitted. As the second polarized perpendicular component is not passed through the polarizer 110, and light does not exit to the outside, effects of preventing the external light reflection may be provided.

The polarizer 110 may be for example a polarizing plate or a polarizing film.

Referring to FIG. 3, the polarizer 110 may be a polarizing film having an integral structure that is made of for example a melt blend of a polymer resin 71 and a dichroic dye 72.

The polymer resin 71 may be for example a hydrophobic polymer resin, for example polyolefin such as polyethylene (PE), polypropylene (PP) and a copolymer thereof; polyamide such as nylon and aromatic polyamide; polyester such as polyethylene terephthalate (PET), polyethyleneterephthalate glycole (PETG), and polyethylenenaphthalate (PEN); polyacryl, such as polymethyl(meth)acrylate, polystyrenes (PS) such as an acrylonitrile-styrene copolymer; polycarbonate; a vinyl chloride-based resin; polyimide; a sulfone resin; polyethersulfone; polyether-etherketone; polyphenylene sulfide; a polyvinyl alcohol resin; a vinylidene chloride resin; a polyvinyl butyral resin; an allylate resin; polyoxymethylene; epoxy resin, a copolymer thereof, or a combination thereof.

Among them, the polymer resin 71 may be for example a polyolefin resin, a polyamide resin, a polyester resin, a polyacrylic resin, a polystyrene resin, a copolymer thereof, or a combination thereof, for example polyethylene (PE), polypropylene (PP), polyethylene terephthalate (PET), polyethylene terephthalate glycole (PETG), polyethylene naphthalate (PEN), nylon, a copolymer thereof, or a combination thereof.

Among them, the polymer resin 71 may be polyolefin. The polyolefin may be for example a mixture of at least two selected from polyethylene (PE), polypropylene (PP), a copolymer of polyethylene and polypropylene (PE-PP), and may be for example a mixture of polypropylene (PP) and a polyethylene-polypropylene copolymer (PE-PP).

The polymer resin 71 may have transmittance of greater than or equal to about 85% in a wavelength region of about 400 nm to 780 nm. The polymer resin 71 may be elongated in a uniaxial direction. The uniaxial direction may be the same as a length direction of the dichroic dye 72 that will be described later.

The dichroic dye 72 is dispersed in the polymer resin 71 and aligned in one direction along the elongation direction of the polymer resin 71. The dichroic dye 72 transmits one perpendicular polarization component out of two perpendicular polarization components in a predetermined wavelength region.

The dichroic dye 72 may be included in an amount of about 0.01 to about 5 parts by weight based on 100 parts by weight of the polymer resin 71. Within the range, sufficient polarization characteristics may be obtained without deteriorating transmittance of a polarization film. Within the above range, the dichroic dye 72 may be included in an amount of about 0.05 to about 1 part by weight based on 100 parts by weight of the polymer resin 71.

The polarizer 110 may have a relatively thin thickness of less than or equal to about 100 μm, for example, about 30 μm to about 95 μm. When the polarizing film 70 has a thickness with the range, the polarizer 110 is relatively thinner than a polyvinyl alcohol polarizing plate requiring a protective layer such as triacetyl cellulose (TAC), and thus, may realize a thin display device.

The compensation film 120 is the same as described above.

The optical film 100 may further include a correction layer (not shown) disposed on one surface of the compensation film 120. The correction layer may be for example a color shift resistant layer, but is not limited thereto.

The optical film 100 may further include a light blocking layer (not shown) extended along the edge. The light blocking layer may be extended along the circumference of the optical film 100 and may be for example disposed between the polarizer 110 and the compensation film 120. The light blocking layer may include an opaque material, for example, a black material. For example, the light blocking layer may be made of a black ink.

The optical film 100 may be applied to various display devices.

A display device according to an embodiment includes a display panel and an optical film disposed on one surface of the display panel. The display panel may be a liquid crystal panel or an organic light emitting panel, but is not limited thereto.

Hereinafter, for one example of the display device, an organic light emitting diode (OLED) display is described.

Figure 4:
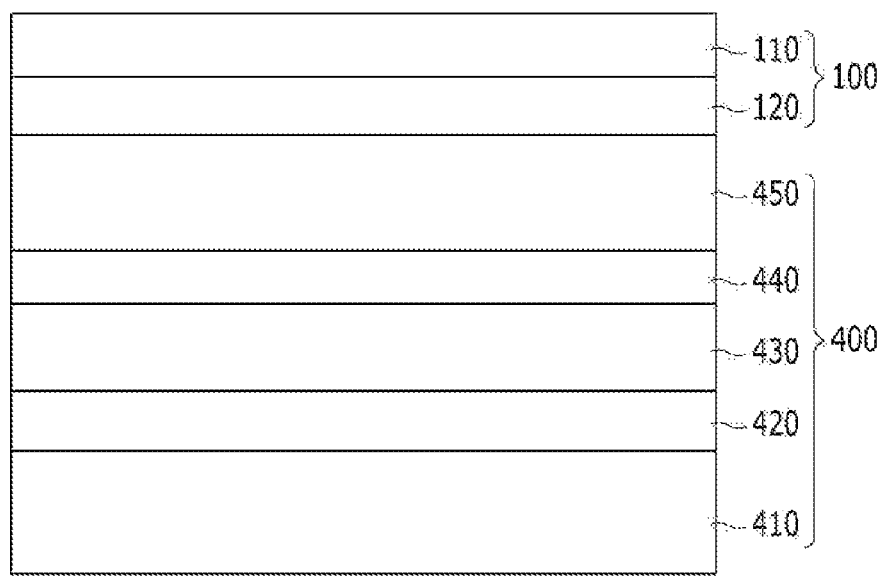
FIG. 4 is a schematic cross-sectional view of an organic light emitting diode (OLED) display according to an embodiment.

FIG. 4 is a schematic cross-sectional view of an organic light emitting diode (OLED) display according to an embodiment.

Referring to FIG. 4, an organic light emitting diode (OLED) display according to an embodiment includes an organic light emitting panel 400 and an optical film 100 disposed on one surface of the organic light emitting panel 400.

The organic light emitting panel 400 may include a base substrate 410, a lower electrode 420, an organic emission layer 430, an upper electrode 440, and an encapsulation substrate 450.

The base substrate 410 may be made of glass or a plastic.

One of the lower electrode 420 and the upper electrode 440 may be an anode and the other may be a cathode. The anode may be an electrode into which holes are injected and may be made of a transparent conductive material having a high work function and passing the emitted light externally, for example ITO or IZO.

The cathode is an electrode into which electrons are injected and may be made of a conducting material having a low work function and having no effect on an organic material, for example aluminum (Al), calcium (Ca), and barium (Ba).

The organic emission layer 430 includes an organic material which may emit light when applying a voltage to the lower electrode 420 and the upper electrode 440.

An auxiliary layer (not shown) may be further provided between the lower electrode 420 and the organic emission layer 430 and between the upper electrode 440 and the organic emission layer 430. The auxiliary layer may include a hole transporting layer, a hole injecting layer, an electron injecting layer, and an electron transporting layer in order to balance electrons and holes.

The encapsulation substrate 450 may be made of glass, a metal, or a polymer, and may seal the lower electrode 420, the organic emission layer 430, and the upper electrode 440 to prevent moisture and/or oxygen inflow from the outside.

The optical film 100 may be disposed at a light emitting side. For example, in the case of a bottom emission structure emitting light at the side of the base substrate 410, the optical film 100 may be disposed on the exterior side of the base substrate 710, while on the other hand, in the case of a top emission structure emitting light at the side of the encapsulation substrate 450, the optical film 100 may be disposed on the exterior side of the encapsulation substrate 450.

The optical film 100 may include the integral structured polarizer 110 and the integrally structured compensation film 120. The polarizer 110 and the compensation film 120 are the same as described above and may prevent light passing the polarizer 110 from being reflected by a metal such as an electrode of the organic light emitting panel 400 and emitting outside of the organic light emitting device, and thus, prevents visibility from being deteriorated by externally inflow light. Therefore, display characteristics of the organic light emitting diode (OLED) display may be improved.

Hereinafter, for one example of the display device, a liquid crystal display (LCD) is described.

Figure 5:
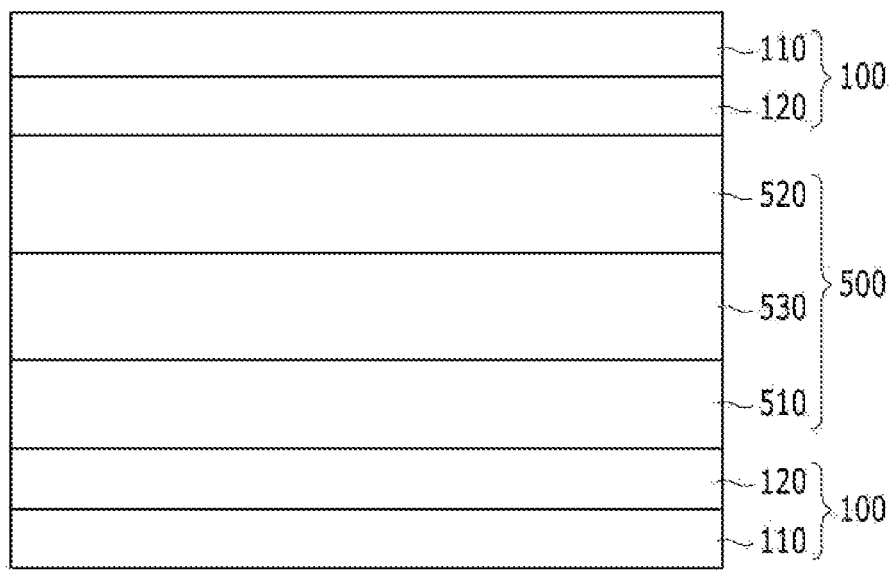
FIG. 5 is a schematic cross-sectional view of a liquid crystal display (LCD) according to an embodiment.

FIG. 5 is a schematic cross-sectional view of a liquid crystal display (LCD) according to an embodiment.

Referring to FIG. 5, a liquid crystal display (LCD) according to an embodiment includes a liquid crystal panel 500 and an optical film 100 positioned on one surface or both surfaces of the liquid crystal panel 500.

The liquid crystal panel 500 may be a twist nematic (TN) mode panel, a vertical alignment (PVA) mode panel, an in-plane switching (IPS) mode panel, an optically compensated bend (OCB) mode panel, or the like.

The liquid crystal panel 500 may include a first display panel 510, a second display panel 520, and a liquid crystal layer 530 interposed between the first display panel 510 and the second display panel 520.

The first display panel 510 may include, for example, a thin film transistor (not shown) formed on a substrate (not shown) and a first electric field generating electrode (not shown) connected to the same, and the second display panel 520 may include, for example, a color filter (not shown) formed on a substrate (not shown) and a second electric field generating electrode (not shown). However, it is not limited thereto, and the color filter may be included in the first display panel 510, while the first electric field generating electrode and the second electric field generating electrode may be disposed on the first display panel 510 together.

The liquid crystal layer 530 may include a plurality of liquid crystal molecules. The liquid crystal molecules may have positive or negative dielectric anisotropy. In the case of the liquid crystal molecules having positive dielectric anisotropy, the major axes thereof may be aligned substantially parallel to the surface of the first display panel 510 and the second display panel 520 when not applying an electric field, and the major axes may be aligned substantially perpendicular to the surface of the first display panel 510 and second display panel 520 when applying an electric field. On the contrary, in the case of the liquid crystal molecules having negative dielectric anisotropy, the major axes may be aligned substantially perpendicular to the surface of the first display panel 510 and the second display panel 520 when not applying an electric field, and the major axes may be aligned substantially parallel to the surface of the first display panel 510 and the second display panel 520 when applying an electric field.

The optical film 100 may be disposed on the outside of the liquid crystal panel 500. Although the optical film 100 is shown to be provided on both the lower part and the upper part of the liquid crystal panel 500 in the drawing, it is not limited thereto, and it may be formed on only one of the lower part and the upper part of the liquid crystal panel 500.

Hereinafter, the present disclosure is illustrated in more detail with reference to examples. However, these examples are exemplary, and the present disclosure is not limited thereto.

EXAMPLES

Examples 1 to 20: Synthesis of Monomer

Example 1: Synthesis of Compound M-1

Compound M-1 is prepared according to Reaction Scheme M-1, and a method of preparing Intermediate I-1 and Compound M-1 as a final product is classified into Steps 1 and 2 and illustrated in detail:

Reaction Scheme M-1

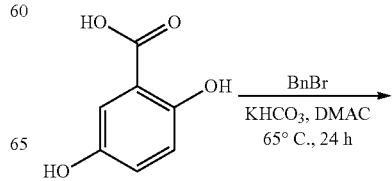

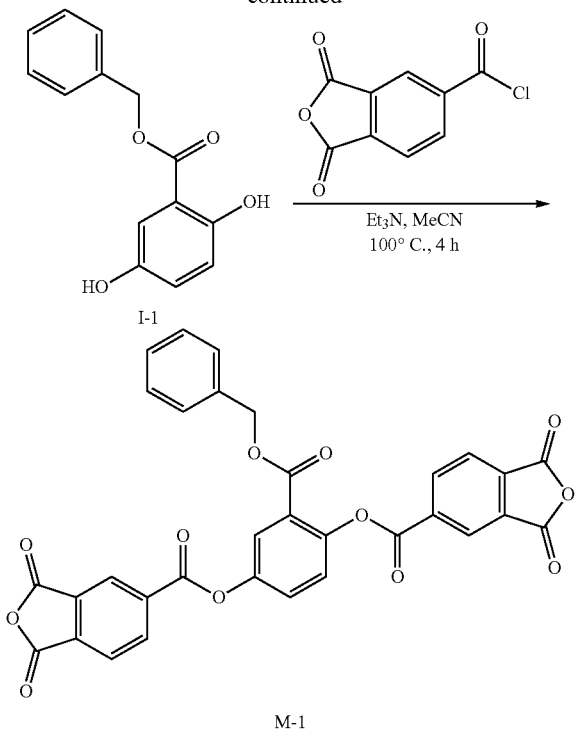

Step 1: Synthesis of Intermediate I-1 (2,5-dihydroxybenzoic acid benzyl ester)

2,5-dihydroxybenzoic acid (m=77.06 grams (gr), 0.5 moles (mol), mw=154.13 grams per mole (g/mol)), benzyl-bromide (m=85.52 gr, 0.5 mol, mw=171.04 g/mol), and potassium hydrogen carbonate (m=100.12 gr, 1 mol, mw=100.12 g/mol) are added to 0.5 liters (L) of dimethyl acetamide (DMAC), and the mixture is stirred under a nitrogen atmosphere at 65° C. for 24 hours. When a reaction is to complete, the mixture is poured into 3 L of water, and the obtained mixture is stirred. The reactant is oily during the initial reaction but gradually becomes solid. Subsequently, the solid is filtered and washed and then, dried at 80° C. to obtain Intermediate I-1 (m=119.7 gr, 0.49 mol, mw=244.25 g/mol) in an off-white powder state (yield: 98.0%).

$R_f$=0.60 (Eluent:ethylacetate:hexane=1:2, TLC silica gel 60 $F_{254}$);

$^1$H NMR (DMSO-$d_6$) 300 MHz, δ, ppm: 5.37 (s, 2H), 6.83 (d, 1H, $J^{12}$=9 Hz), 6.99 (dd, 1H, $J^{12}$=9 Hz, $J^{13}$=3.0 Hz), 7.19 (d, 1H, $J^{13}$=3.0 Hz), 7.35-7.50 (m, 5H), 9.25 (br s, 1H, OH), 9.89 (br s, 1H, OH).

Step 2: Synthesis of Monomer M-1 (bis-trimellitic Acid Anhydride Ester of benzyl-2,5-dihydroxy-benzoate)

Trimellitic anhydride chloride (m=115.8 gr, 0.55 mol, mw=210.57 g/mol) is added to 1.5 L of acetonitrile and dissolved therein at 100° C., and Intermediate I-1 (m=61.06 gr, 0.25 mol, mw=244.2 g/mol) is added to the solution. Then, another solution obtained by dissolving triethylamine in 200 milliliters (mL) of acetonitrile (m=55.65 gr, 0.55 mol, mw=101.19 g/mol) is added to the reaction mixture in a dropwise fashion at 100° C., and the obtained mixture is vigorously stirred for 30 minutes. Subsequently, the resulting material is refluxed for 4 hours and filtered in a hot state to remove an insoluble material, and the filtered solution is cooled down to room temperature to obtain a white crystalline precipitate. The precipitate is filtered and washed with a small amount of acetonitrile, and a white solid obtained therefrom is twice recrystallized with 1.5 L of acetonitrile, while acetic anhydride (m=102.09 gr, 1 mol, mw=102.09 g/mol) is added thereto. The crystallized solid is washed with a small amount of acetonitrile, dried at 90° C. under vacuum for 24 hours to obtain Monomer M-1 (m=118.5 gr, 0.2 mmol, mw=592.48 g/mol) as a white crystalline solid (yield: 80%). $^1$H NMR (DMSO-$d_6$) 300 MHz, δ, ppm: 5.21 (s, 2H), 7.20-7.30 (m, 5H), 7.67 (d, 1H, $J^{12}$=8.7 Hz), 7.85 (dd, 1H, $J^{12}$=8.7 Hz, $J^{13}$=2.7 Hz), 8.14 (d, 1H, $J^{13}$=2.7 Hz), 8.24 (dd, 1H, $J^{12}$=8.1 Hz, $J^{14}$=0.6 Hz), 8.30 (d, 1H, $J^{12}$=8.1 Hz), 8.46-8.47 (m, 1H), 8.55 (dd, 1H, $J^{12}$=8.1 Hz, $J^{13}$=1.5 Hz), 8.65-8.68 (m, 2H);

HRMS APCI (m/z) for $C_{32}H_{16}O_{12}$: 592.0607 (measured mass), 592.0643 (calculated mass) for [M+H]$^+$;

Thermal analysis: TGA (heating: 10 degrees Centigrade per minute (° C./min), $N_2$ atmosphere): 1 percent by weight (wt %) loss (268° C.); and DSC (heating: 10° C./min, $N_2$ atmosphere): mp=105.1° C. (CrN), 195.5° C. (NI).

Example 2: Synthesis of Monomer M-2

Compound M-2 is prepared according to Reaction Scheme M-2, and a method of preparing Intermediates I-2a and I-2b and Compound M-2 as a final product is respectively classified into Steps 1 to 3 and illustrated in detail:

Reaction Scheme M-2

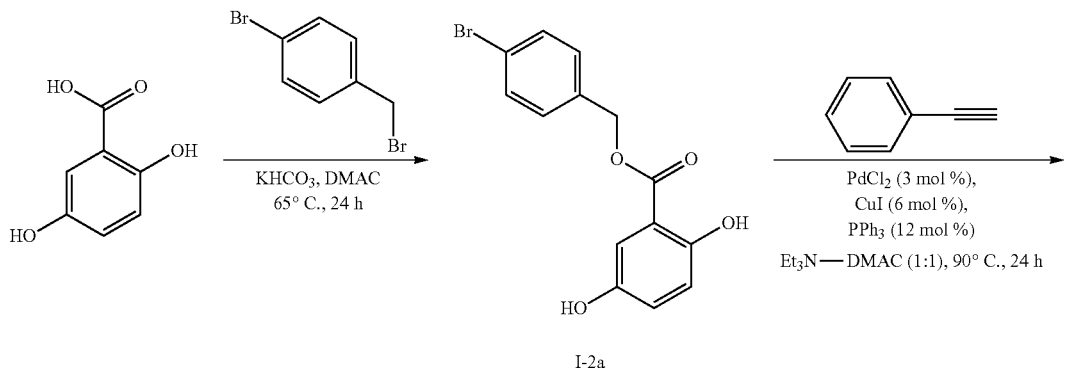

I-2a

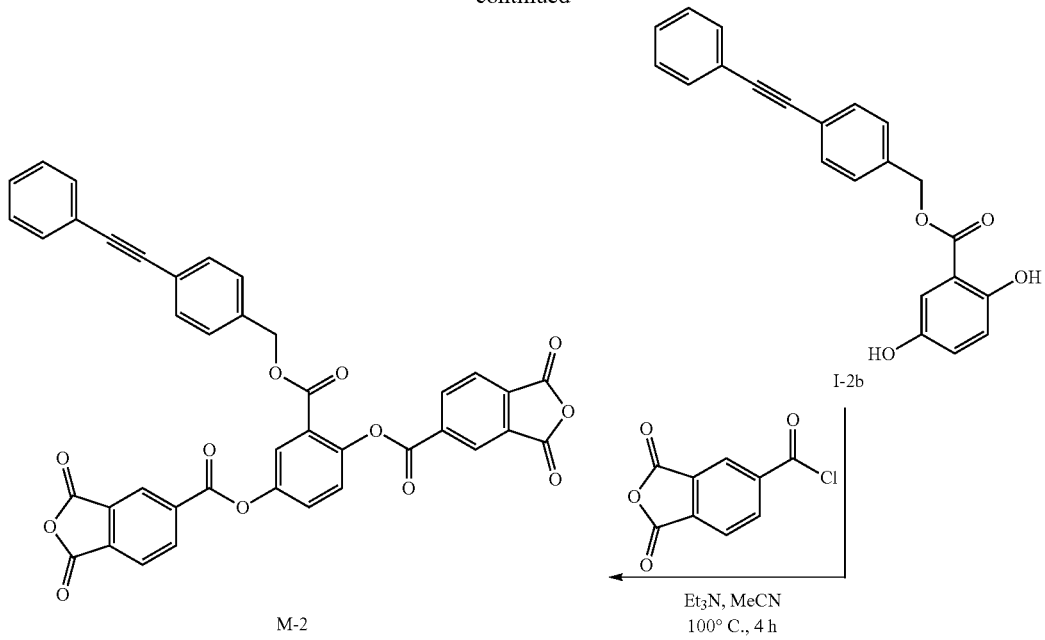

M-2

I-2b

Et₃N, MeCN
100° C., 4 h

Step 1: Synthesis of Intermediate I-2a (2,5-dihydroxybenzoic acid 4-bromobenzyl ester)

2,5-dihydroxybenzoic acid (mw=154.13 g/mol, v=101 mmol, m=15.57 gr), 1-bromo-4-bromomethylbenzene (mw=249.93 g/mol, v=101 mmol, m=25.25 gr), and potassium hydrogen carbonate (mw=100.12 g/mol, v=303 mmol, m=30.35 gr) are added to 150 mL of dimethyl acetamide (DMAC), and the mixture is stirred under a nitrogen atmosphere at 65° C. for 24 hours. When a reaction is complete, the resultant is poured into 2 L of water, and the obtained mixture is vigorously stirred. A precipitate therein is filtered and thoroughly washed with water. Subsequently, the precipitate is dried at 80° C. for 24 hours under a reduced pressure to obtain Intermediate I-2a (mw=323.15 g/mol, v=99.4 mmol, m=32.13 gr) in a white powder state (a yield: 98.4%). $R_f$=0.4 (Eluent:ethylacetate:hexane=1:4, TLC silica gel 60 F254);

¹H NMR (DMSO-d6) 300 MHz, δ, ppm: 5.33 (s, 2H), 6.83 (d, 1H, $J^{12}$=9 Hz), 6.98 (dd, 1H, $J^{12}$=9 Hz, $J^{13}$=3.0 Hz), 7.17 (d, 1H, $J^{13}$=3.0 Hz), 7.45 (d, 2H, $J^{12}$=8.4 Hz), 7.62 (d, 2H, $J^{12}$=8.4 Hz), 9.20 (s, 1H, OH), 9.89 (s, 1H, OH).

Step 2: Synthesis of Intermediate I-2b (2,5-dihydroxybenzoic acid 4-(phenylethynyl)benzyl ester)

2,5-dihydroxybenzoic acid 4-bromobenzyl ester (m=45.24 gr, 140 mmol, mw=323.15 g/mol) and phenylacetylene (m=21.45 gr, 210 mmol, mw=102.13 g/mol) are added to a mixed solvent of 0.3 L of triethylamine and 0.3 L of dimethyl acetamide and then, dissolved therein in a 1 L 3-necked round-bottomed flask equipped with a nitrogen inlet and a condenser. The solution is stirred and purged with dried nitrogen gas for 1 hour. Subsequently, the solution is stirred while palladium(II) chloride (m=0.75 gr, 4.2 mmol, mw=177.33 g/mol), copper(I) iodide (m=1.6 gr, 8.4 mol, mw=190.45 g/mol) and triphenylphosphine (m=4.77 gr, 18.3 mol, mw=262.45 g/mol) are added thereto. Then, nitrogen gas is additionally injected thereinto for 10 minutes, a nitrogen outlet is closed, and the mixture is maintained under nitrogen at 90° C. for 24 hours while stirred. When a reaction is complete, the triethylamine is evaporated under a reduced pressure to obtain a crude product as a brown solid. The crude product is washed with water and dissolved in 1.5 L of hot methanol and then, treated with charcoal and filtered. The methanol is evaporated under a reduced pressure, and a solid obtained therefrom is three times crystallized with iso-propanol. Subsequently, the solid is dried under vacuum at 75° C. for 24 hours to obtain Intermediate I-2b (m=25 gr, 72.6 mmol, mw=344.37 g/mol) in a light brown powder (a yield: 51.9%).

$R_f$=0.59 (Eluent:ethylacetate:hexane=1:2, TLC silica gel 60 F254); and

¹H NMR (DMSO-d₆) 300 MHz, δ, ppm: 5.41 (s, 2H), 6.83 (d, 1H, $J^{12}$=9 Hz), 6.99 (dd, 1H, $J^{12}$=9 Hz, $J^{13}$=3.0 Hz), 7.20 (d, 1H, $J^{13}$=3.0 Hz), 7.42-7.45 (m, 3H), 7.51-7.63 (m, 6H), 9.22 (s, 1H, OH), 9.91 (s, 1H, OH).

Step 3: Synthesis of Monomer M-2 (bis-trimellitic acid anhydride ester of 2,5-dihydroxybenzoic acid 4-(phenylethynyl)benzyl ester)

Monomer M-2 is synthesized in a similar method to that of Monomer M-1 by adding trimellitic anhydride chloride (m=30.2 gr, 143.4 mmol, mw=210.57 g/mol), Intermediate I-2b (m=22.45 gr, 65.2 mmol, mw=344.32 g/mol), and triethylamine (m=14.5 gr, 143.4 mol, mw=101.19 g/mol) to 800 mL of acetonitrile and then, reacting them. Then, a solid crystallized therein is twice recrystallized with acetonitrile while acetic anhydride is added to the reactant, washed with a small amount of acetonitrile, and dried under vacuum at 90° C. for 24 hours to obtain Monomer M-2 (m=36.4 gr, 52.6 mmol, mw=692.60 g/mol) in a white solid state (a yield: 80.6%). $^1$H NMR (DMSO-d$_6$) 300 MHz, δ, ppm: 5.23 (s, 2H), 7.29 (s, 4H), 7.44-7.47 (m, 3H), 7.53-7.58 (m, 2H), 7.65 (d, 1H, J$^{12}$=8.7 Hz), 7.86 (dd, 1H, J$^{12}$=8.7 Hz, J$^{13}$=2.7 Hz), 8.16 (d, 1H, J$^{13}$=2.7 Hz), 8.22 (d, 1H, J$^{12}$=8.4 Hz), 8.30 (d, 1H, J$^{12}$=8.4 Hz), 8.38 (s, 1H), 8.50 (dd, 1H, J$^{12}$=7.8 Hz, J$^{13}$=1.5 Hz), 8.65-8.69 (m, 2H);

HRMS APCI (m/z) for C$_{40}$H$_{20}$O$_{12}$: 692.0899 (measured mass), 692.0955 (calculated mass) for [M+H]$^+$; thermal analysis: TGA (heating 10° C./min, N$_2$ atmosphere): 1 wt % loss (301° C.); and DSC (heating 10° C./min, N$_2$ atmosphere): mp=249.8° C.

Example 3: Synthesis of Monomer M-3

Compound M-3 is prepared according to Reaction Scheme M-3, and a method of preparing Intermediate I-3 and Compound M-3 as a final product is classified into Steps 1 and 2 and illustrated in detail as follows:

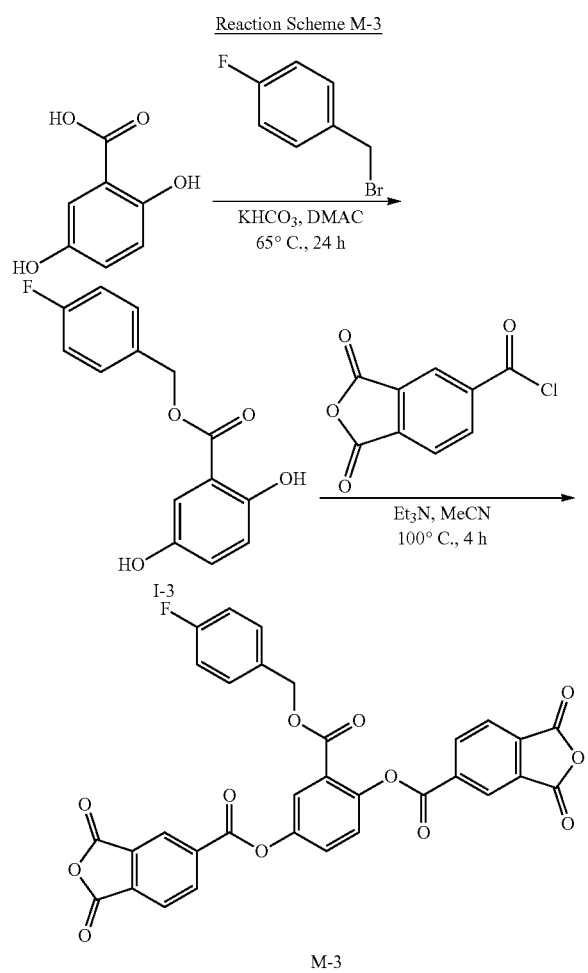

Reaction Scheme M-3

Step 1: Synthesis of Intermediate I-3 (2,5-dihydroxybenzoic acid 4-fluorobenzyl ester)

2,5-dihydroxybenzoic acid (m=17.94 gr, 116.4 mmol, mw=154.13 g/mol), 4-fluorobenzylbromide (m=22 gr, 116.4 mmol, mw=189.02 g/mol), and potassium hydrogen carbonate (m=24 gr, 240 mol, mw=100.12 g/mol) are added to 0.1 L of dimethyl acetamide, and the mixture is reacted under a nitrogen atmosphere at 65° C. for 24 hours to obtain Intermediate I-3 (m=29.63 gr, 113 mmol, mw=262.24 g/mol) as a white solid (a yield: 97.1%) according to a similar method to that of Intermediate I-1.

R$_f$=0.58 (Eluent: ethylacetate:hexane=1:2, TLC silica gel 60 F$_{254}$); $^1$H NMR (DMSO-d$_6$) 300 MHz, δ, ppm: 5.35 (s, 2H), 6.83 (d, 1H, J$^{12}$=9 Hz), 6.98 (dd, 1H, J$^{12}$=9 Hz, J$^{13}$=3.0 Hz), 7.16 (d, 1H, J$^{13}$=3.0 Hz), 7.22-7.28 (m, 2H), 7.52-7.57 (m, 2H), 9.19 (s, 1H, OH), 9.92 (s, 1H, OH).

Step 2: Synthesis of Monomer M-3 (bis-trimellitic acid anhydride ester of 2,5-dihydroxybenzoic acid 4-fluorobenzyl ester)

Intermediate I-3 (m=28.97 gr, 110.47 mmol, mw=262.24 g/mol), trimellitic anhydride chloride (m=51.2 gr, 243 mmol, mw=210.57 g/mol), and triethylamine (m=24.55 gr, 243 mol, mw=101.19 g/mol) are added to 800 mL of acetonitrile to synthesize a product in a similar method to that of Monomer M-1, the product is twice recrystallized with acetonitrile while acetic anhydride is added thereto, and a solid crystallized therein is washed with a small amount of acetonitrile and dried under vacuum 90° C. for 24 hours to obtain Monomer M-3 (m=35 gr, 57.3 mmol, mw=610.47 g/mol) in a white solid state (a yield: 51.9%). $^1$H NMR (DMSO-d$_6$) 300 MHz, δ, ppm: 5.19 (s, 2H), 6.99-7.04 (m, 2H), 7.29-7.33 (m, 2H), 7.66 (d, 1H, J$^{12}$=9 Hz), 7.85 (dd, 1H, J$^{12}$=8.7 Hz, J$^{13}$=3 Hz), 8.13 (d, 1H, J$^{13}$=2.7 Hz), 8.24 (d, 1H, J$^{12}$=8.1 Hz), 8.30 (d, 1H, J$^{12}$=8.1 Hz), 8.43-8.44 (m, 1H), 8.52 (dd, 1H, J$^{12}$=8.1 Hz, J$^{13}$=1.5 Hz), 8.65-8.67 (m, 2H);

HRMS APCI (m/z) for C$_{32}$H$_{15}$FO$_{12}$: 610.0507 (measured mass), 610.0548 (calculated mass) for [M+H]$^+$;

Thermal analysis: TGA (heating 10° C./min, N$_2$ atmosphere): 1 wt % loss (281° C.); DSC (heating 10° C./min, N$_2$ atmosphere): mp=219.9° C.

Example 4: Synthesis of Monomer M-4

Compound M-4 is prepared according to Reaction Scheme M-4, and a method of manufacturing Intermediates I-2a and I-4 and Compound M-4 as a final product are respectively classified into Steps 1 to 3 and illustrated in detail as follows:

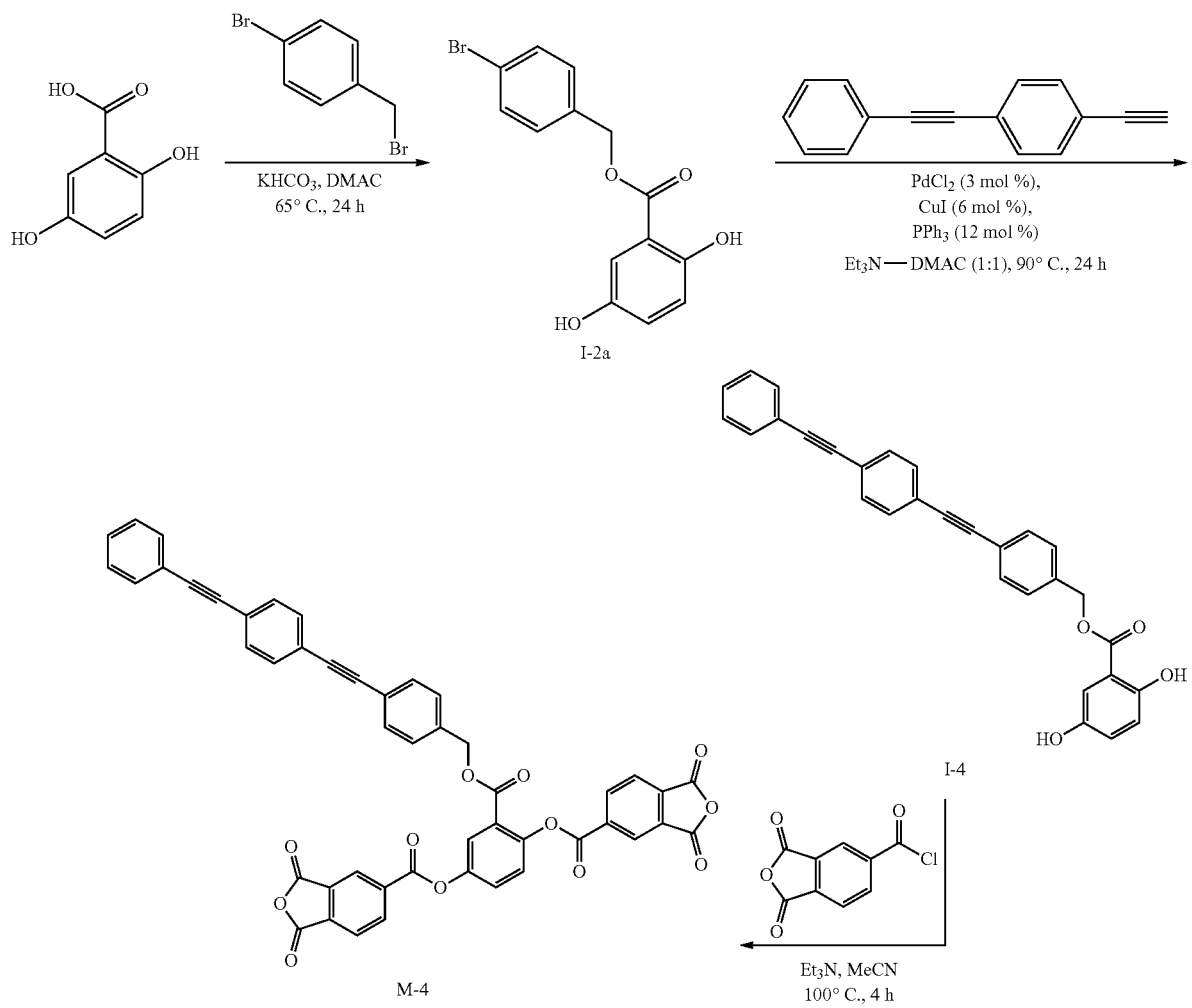

Reaction Scheme M-4

Step 1: Synthesis of Intermediate I-2a
(2,5-dihydroxybenzoic acid 4-bromobenzyl ester)

Intermediate I-2a is synthesized according to the same method as Step 1 of Synthesis Example 2.

Step 2: Synthesis of Intermediate I-4
(2,5-dihydroxybenzoic acid 4-(4-phenylethynyl-phenylethynyl)benzyl ester)

Intermediate I-2a (m=32 gr, 99 mmol, mw=323.15 g/mol) and 1-ethynyl-4-phenylethynylbenzene (m=20.63 gr, 102 mmol, mw=202.26 g/mol) are added to 0.5 L of triethylamine and dissolved therein in 1 L 3-necked round-bottomed flask equipped with a nitrogen inlet and a condenser.

The solution is stirred and then, purged with dry nitrogen gas for 1 hour. Subsequently, palladium chloride (II) (m=0.35 gr, 2 mmol, mw=177.33 g/mol), copper (I) iodide (m=0.76 gr, 4 mmol, mw=190.45 g/mol), and triphenylphosphine (m=2.1 gr, 8 mmol, mw=262.45 g/mol) are added thereto. Subsequently, after additionally injecting nitrogen gas for 10 minutes and closing a nitrogen outlet, the mixture is maintained under nitrogen at 80° C. for 24 hours while stirred. When the reaction is complete, triethylamine is evaporated under a reduced pressure to obtain a crude product as a brown solid. The crude product is purified by being suspended in 400 mL of methanol, boiled for 30 minutes, cooled down to room temperature, and filtered. This process is repeated three times. Herein, the first mother solution appears saturated brown and includes some precipitate, the second mother solution appears light brown and includes tiny amount of precipitate, and the last mother solution appears light yellow. The finally purified product in a light brown powder state is dried under vacuum at 75° C. for 24 hours to obtain Intermediate I-4 (m=32.1 gr, 72.2 mmol, mw=444.49 g/mol) in a light brown state (a yield: 73.0%).

$R_f$=0.59 (Eluent: ethylacetate:hexane=1:2, TLC silica gel 60 $F_{254}$);

$^1$H NMR (DMSO-$d_6$) 300 MHz, δ, ppm: 5.41 (s, 2H), 6.82 (d, 1H, $J^{12}$=9 Hz), 6.97 (dd, 1H, $J^{12}$=9 Hz, $J^{13}$=3.0 Hz), 7.20 (d, 1H, $J^{13}$=3.0 Hz), 7.44-7.46 (m, 3H), 7.53-7.65 (m, 10H), 9.23 (s, 1H, OH), 9.91 (s, 1H, OH).

Step 3: Synthesis of Monomer M-4 (bis-trimellitic Acid Anhydride Ester of 2,5-dihydroxybenzoic acid 4-(4-phenylethynyl-phenylethynyl)benzyl ester)

Intermediate I-4 (m=12 gr, 27 mmol, mw=444.49 g/mol), trimellitic anhydride chloride (m=12.5 gr, 59.4 mmol, mw=210.57 g/mol), and triethylamine (m=6 gr, 59.4 mol, mw=101.19 g/mol) are added to 800 mL of acetonitrile for a reaction to synthesize Monomer M-4 in a similar method to that of Monomer M-1.

When a reaction is complete, a product therefrom is twice recrystallized with acetonitrile while acetic anhydride is added thereto, and a solid crystallized therein is washed with a small amount of acetonitrile and dried under vacuum at 90° C. for 24 hours to obtain Monomer M-4 (m=15.1 gr, 19 mmol, mw=792.72 g/mol) as a brownish solid (a yield: 70.4%).

$^1$H NMR (DMSO-d$_6$) 300 MHz, δ, ppm: 5.23 (s, 2H), 7.30 (s, 4H), 7.44-7.47 (m, 3H), 7.58-7.67 (m, 7H), 7.86 (dd, 1H, J$^{12}$=8.7 Hz, J$^{13}$=2.7 Hz), 8.18 (d, 1H, J$^{13}$=2.7 Hz), 8.23 (d, 1H, J$^{12}$=7.8 Hz), 8.30 (d, 1H, J$^{12}$=8.1 Hz), 8.37 (s, 1H), 8.50 (dd, 1H, J$^{12}$=7.8 Hz, J=0.9 Hz), 8.66-8.69 (m, 2H);

Thermal analysis: TGA (heating 10° C./min, N$_2$ atmosphere): 1 wt % loss (261° C.);

DSC (heating 10° C./min, N$_2$ atmosphere): mp=254.7° C.

Example 5: Synthesis of Monomer M-5

Compound M-5 is prepared according to Reaction Scheme M-5, and a method of preparing Intermediate I-5 and Compound M-5 as a final product is respectively classified into Steps 1 and 2 and illustrated in detail as follows:

Reaction Scheme M-5

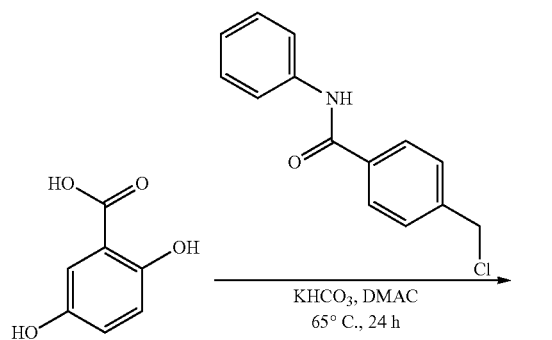

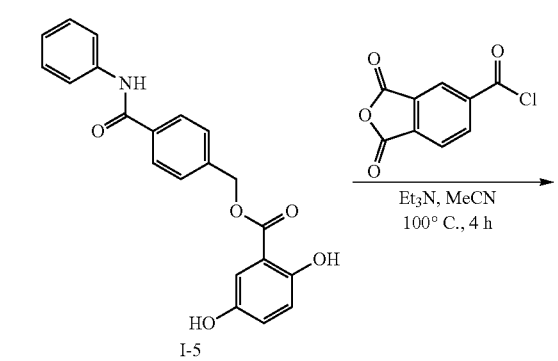

I-5

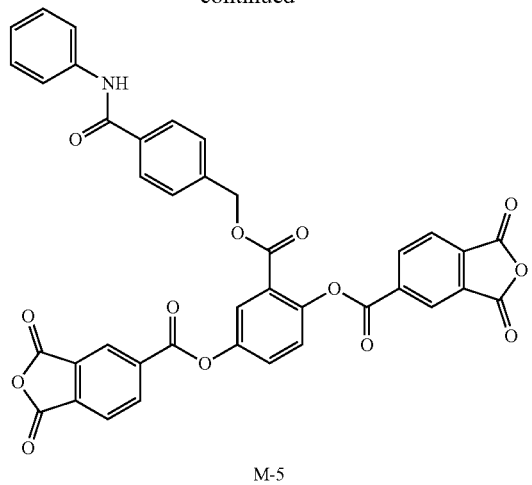

M-5

Step 1: Synthesis of Intermediate I-5 (2,5-dihydroxy-benzoic acid 4-phenylcarbamoylbenzyl ester)

2,5-dihydroxybenzoic acid (m=15.41 gr, 100 mmol, mw=154.12 g/mol), 4-chloromethyl-N-phenyl-benzamide (m=24.57 gram, 100 mmol, mw=245.71 g/mol), and potassium hydrogen carbonate (m=30 gr, 300 mmol, mw=100.12 g/mol) are added to 0.2 L of dimethyl acetamide (DMAC), and the mixture is reacted under a nitrogen atmosphere at 65° C. for 24 hours to synthesize a product in a similar method to that of Intermediate I-1 and crystallized with acetone/iso-propanol to obtain Intermediate I-5 (m=27.3 gr, 75 mmol, mw=363.37 g/mol) in a white solid state (a yield: 75.0%).

R$_f$=0.75 (Eluent: ethylacetate:hexane=1:1, TLC silica gel 60 F$_{254}$); and $^1$H NMR (DMSO-d$_6$) 300 MHz, δ, ppm: 5.46 (s, 2H), 6.84 (d, 1H, J$^{12}$=9 Hz), 6.99 (dd, 1H, J$^{12}$=9 Hz, J$^{13}$=3.0 Hz), 7.08-7.13 (m, 1H), 7.21 (d, 1H, J$^{13}$=3.0 Hz), 7.33-7.38 (m, 2H), 7.63 (d, 2H, J$^{12}$=8.4 Hz), 7.78 (d, 2H, J$^{12}$=7.8 Hz), 7.99 (d, 2H, J$^{12}$=8.4 Hz), 9.23 (s, 1H, OH), 9.90 (s, 1H, OH), 10.27 (s, 1H, NH).

Step 2: Synthesis of Monomer M-5 (bis-trimellitic acid anhydride ester of 2,5-dihydroxybenzoic acid 4-phenylcarbamoylbenzyl ester)

Intermediate I-5 (m=19 gr, 52.2 mmol, mw=363.37 g/mol), trimellitic anhydride chloride (m=24.2 gr, 114.9 mmol, mw=210.57 g/mol), and triethylamine (m=11.6 gr, 114.9 mol, mw=101.19 g/mol) are added to 1 L of acetonitrile, and the mixture is reacted in a similar method to that of monomer M-1 to obtain monomer M-5. When a reaction is complete, a product therefrom is twice crystallized with acetonitrile while acetic anhydride is added thereto, and a solid crystallized therein is washed with a small amount of acetonitrile and dried under vacuum at 90° C. for 24 hours to obtain Monomer M-5 (m=26.3 gr, 37 mmol, mw=711.60 g/mol) in a white solid state (a yield: 70.9%).

$^1$H NMR (DMSO-d$_6$) 300 MHz, δ, ppm: 5.30 (s, 2H), 7.09-7.14 (m, 1H), 7.33-7.43 (m, 4H), 7.66 (d, 1H, J$^{13}$=9 Hz), 7.71-7.76 (m, 4H), 7.86 (dd, 1H, J$^{12}$=9 Hz, J$^{13}$=3 Hz), 8.18-8.20 (m, 2H), 8.30 (d, 1H, $J^{12}$=8.1 Hz), 8.41 (s, 1H), 8.49 (dd, 1H, $J^{12}$=8.1 Hz, J=1.5 Hz), 8.66-8.69 (m, 2H);

HRMS APCI (m/z) for $C_{39}H_{21}NO_{13}$: 712.1098 (measured mass), 712.1091 (calculated mass) for $[M+H]^+$; and Thermal analysis: TGA (heating 10° C./min, $N_2$ atmosphere): 1 wt % loss (304° C.); DSC (heating 10° C./min, $N_2$ atmosphere): mp=259° C.

Example 6: Synthesis of Monomer M-6

Compound M-6 is prepared according to Reaction Scheme M-6, and a method of preparing Intermediate I-6 and Compound M-6 as a final product is classified into Steps 1 and 2 and illustrated in detail as follows:

Reaction Scheme M-6

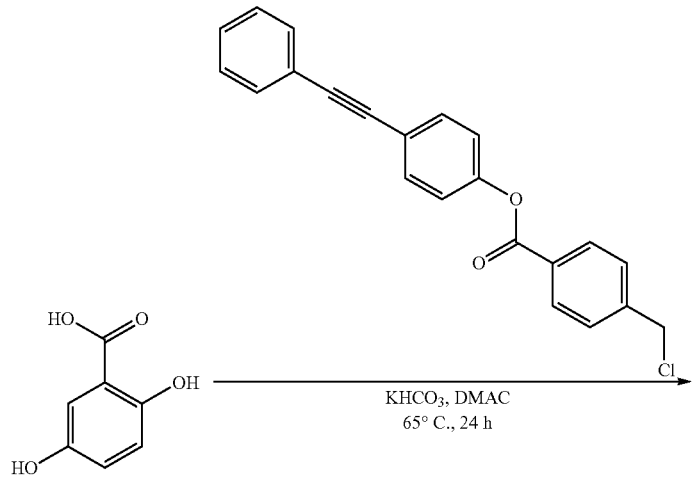

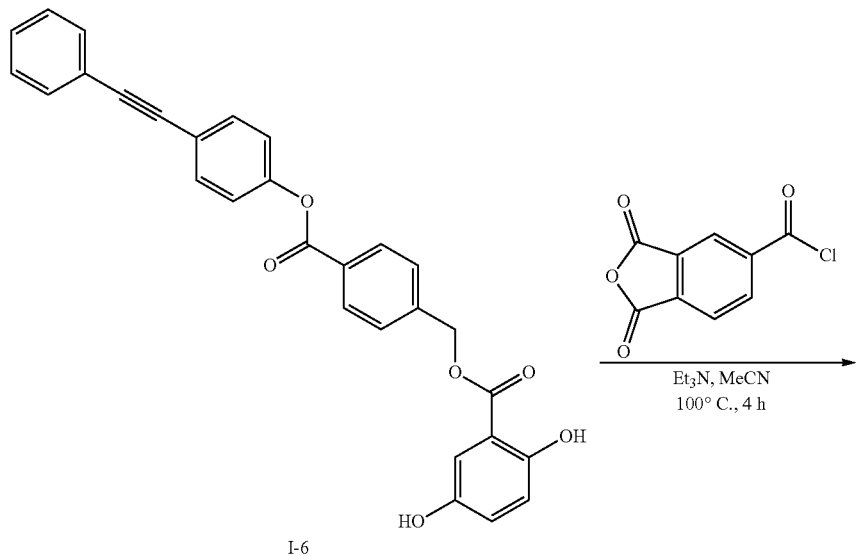

I-6

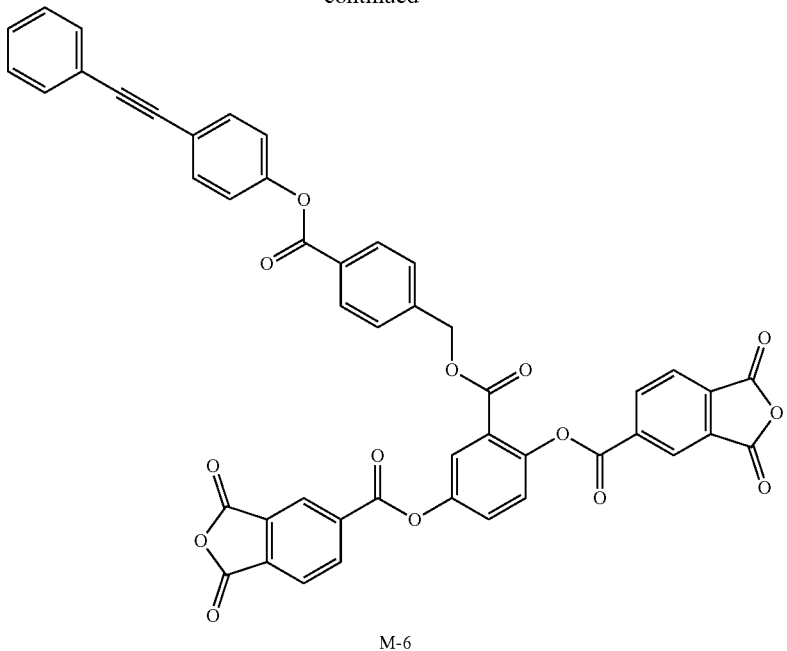

M-6

Step 1: Synthesis of Intermediate I-6 (2,5-dihydroxybenzoic acid 4-(4-phenylethynylphenoxycarbonyl)benzyl ester):

2,5-dihydroxybenzoic acid (m=13.6 gr, 88.1 mmol, mw=154.12 g/mol), 4-chloromethylbenzoic acid 4-phenylethynylphenyl ester (m=30.55 gr, 88.1 mmol, mw=316.82 g/mol), and potassium hydrogen carbonate (m=26.5 gr, 264.3 mmol, mw=100.12 g/mol) are added to 0.3 L of dimethyl acetamide, and the mixture is reacted under a nitrogen atmosphere at 65° C. for 24 hours in a similar method to that of Intermediate I-1 to obtain Intermediate I-6. The product is crystallized with acetone/iso-propanol to obtain Intermediate I-6 (m=27.9 gr, 60 mmol, mw=464.48 g/mol) in a white solid state (a yield: 68.1%).

$^1$H NMR (DMSO-d6) 300 MHz, δ, ppm: 5.50 (s, 2H), 6.85 (d, 1H, J12=9 Hz), 7.00 (dd, 1H, J12=9 Hz, J13=3.0 Hz), 7.23 (d, 1H, J13=3.0 Hz), 7.36-7.46 (m, 5H), 7.56-7.60 (m, 2H), 7.65-7.74 (m, 4H), 8.15-8.20 (m, 2H), 9.23 (s, 1H, OH), 9.89 (s, 1H, OH).

Step 2: Synthesis of Monomer M-6 (bis-trimellitic acid anhydride ester of 2,5-dihydroxybenzoic acid 4-(4-phenylethynylphenoxycarbonyl)benzyl ester)

Intermediate I-6 (m=22.7 gr, 48.9 mmol, mw=464.48 g/mol), trimellitic anhydride chloride (m=22.6 gr, 107.5 mmol, mw=210.57 g/mol), and triethylamine (m=10.9 gr, 107.5 mol, mw=101.19 g/mol) are added to 1 L of acetonitrile, and the mixture is reacted to synthesize Monomer M-6 in a similar method to that of Monomer M-1. When the reaction is complete, the product is twice crystallized with acetonitrile while acetic anhydride is added thereto, and a solid crystallized therein is washed with a small amount of acetonitrile and then, dried under vacuum at 90° C. for 24 hours to obtain Monomer M-6 (m=24.6 gr, 30.3 mmol, mw=812.71 g/mol) in a white solid state (a yield: 62.0%).
$^1$H NMR (DMSO-d$_6$) 300 MHz, δ, ppm: 5.33 (s, 2H), 7.37-7.68 (m, 11H), 7.87-7.93 (m, 3H), 8.19-8.30 (m, 3H), 8.42 (brs, 1H), 8.53 (br s, 1H), 8.67 (br s, 1H).

Example 7: Synthesis of Monomer M-7

Compound M-7 is prepared according to Reaction Scheme M-7, and a method of preparing Intermediate I-7 and Compound M-7 as a final product are classified into Steps 1 and 2 and illustrated in detail as follows:

Reaction Scheme M-7

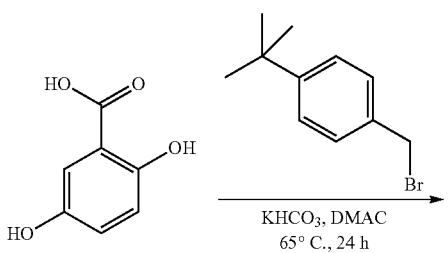

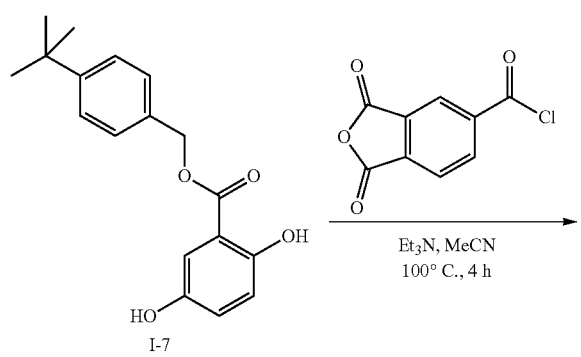

I-7

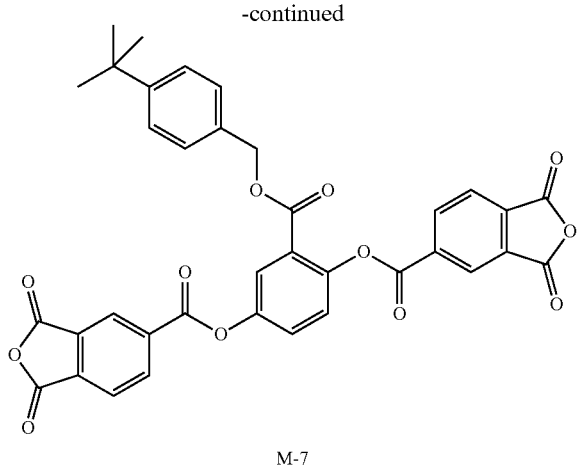

M-7

Step 1: Synthesis of Intermediate I-7
(2,5-dihydroxybenzoic acid 4-tert-butylbenzyl ester)

2,5-dihydroxybenzoic acid (m=33.72 gr, 218.81 mmol, mw=154.12 g/mol), 4-tert-butylbenzyl bromide (m=26.95 gr, 218.81 mmol, mw=227.14 g/mol), and potassium hydrogen carbonate (m=43.81 gr, 437.62 mmol, mw=100.12 g/mol) are added to 0.3 L of dimethyl acetamide, and the mixture is reacted under a nitrogen atmosphere at 65° C. for 24 hours in a similar method to that of Intermediate I-1 to obtain Intermediate I-7 (m=65 gr, 216.41 mmol, mw=300.36 g/mol). Intermediate I-7 is in a yellow solidified oil state at a low temperature (a yield: 98.9%).

$R_f$=0.79 (Eluent: ethylacetate:hexane=1:2, TLC silica gel 60 F254); and $^1$H NMR (DMSO-d6) 300 MHz, δ, ppm: 1.28 (s, 9H), 5.32 (s, 2H), 6.83 (d, 1H, J12=9.0 Hz), 6.97 (dd, 1H, J12=9.0 Hz, J13=3.0 Hz), 7.18 (d, 1H, J13=3.0 Hz), 7.38-7.45 (m, 4H), 9.60 (br s, 2H).

Step 2: Synthesis of Monomer M-7 (bis-trimellitic acid anhydride ester of 2,5-dihydroxybenzoic acid 4-tert-butylbenzyl ester)

A Monomer M-7 solution is prepared in a similar method to that of Monomer M-1 except for adding trimellitic anhydride chloride (m=99 gr, 470 mmol, mw=210.57 g/mol), Intermediate I-7 (m=65.7 gr, 218.7 mmol, mw=300.36 g/mol), and triethylamine (m=47.5 gr, 470 mmol, mw=101.19 g/mol) to 1.5 L of acetonitrile. When the solution is filtered in a hot state to remove an insoluble material, a reaction product having low solubility in acetonitrile is immediately precipitated. The precipitate is twice refluxed for 2 hours with acetic anhydride (50 mL) dissolved in acetonitrile (800 mL). The solid is cooled down to room temperature and filtered and then, washed with a small amount of acetonitrile and dried under vacuum at 90° C. for 24 hours to obtain Monomer M-7 (m=96.6 gr, 148.9 mmol, mw=648.59 g/mol) in a white solid state (a yield: 68.1%).

$^1$H NMR (DMSO-d$_6$) 300 MHz, δ, ppm: 1.22 (s, 9H), 5.17 (s, 2H), 7.20 (d, 2H, $J^{12}$=8.4 Hz), 7.27 (d, 2H, $J^{12}$=8.4 Hz), 7.67 (d, 1H, $J^{12}$=8.7 Hz), 7.85 (dd, 1H, $J^{12}$=8.7 Hz, $J^{13}$=2.7 Hz), 8.12 (d, 1H, $J^{13}$=2.7 Hz), 8.24 (dd, 1H, $J^{12}$=7.5 Hz, $J^{14}$=1.2 Hz), 8.29 (d, 1H, $J^{12}$=8.4 Hz), 8.53-8.59 (m, 1H), 8.64-8.68 (m, 1H);

Thermal analysis: TGA (heating 10° C./min, N$_2$ atmosphere): 1 wt % loss (305.5° C.); and DSC (heating 10° C./min, N$_2$ atmosphere): mp=234.7° C.

Example 8: Synthesis of Monomer M-8

Compound M-8 is prepared according to Reaction Scheme M-8, and a method of preparing Intermediate I-8 and Compound M-8 as a final product are respectively classified into Steps 1 and 2 and illustrated in detail as follows:

Reaction Scheme M-8

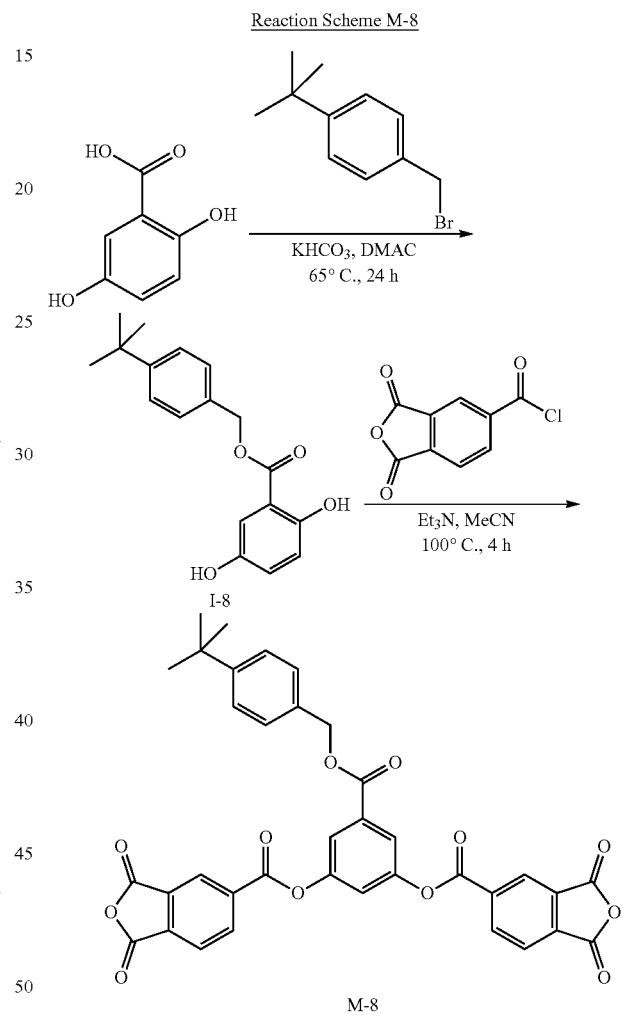

M-8

Step 1: Synthesis of Intermediate I-8
(3,5-dihydroxybenzoic acid 4-tert-butylbenzyl ester)

3,5-dihydroxybenzoic acid (m=15.41 gr, 0.1 mol, mw=154.12 g/mol), 4-tert-butylbenzyl bromide (m=22.71 gr, 0.1 mol, mw=227.14 g/mol), and potassium hydrogen carbonate (m=20.804 gr, 0.2 mol, mw=100.12 g/mol) are added to 100 mL of dimethyl acetamide, and then, they are reacted under a nitrogen atmosphere at 65° C. for 24 hours in a similar method to that of Intermediate I-1 to obtain Intermediate I-8 (m=57.7 gr, 0.192 mol, mw=300.36 g/mol) in a white solid state (a yield: 96.0%).

$R_f$=0.38 (Eluent: ethylacetate:hexane=1:2, TLC silica gel 60 F254);

Mp=186-188° C.; and $^1$H NMR (DMSO-d6) 300 MHz, δ, ppm: 1.28 (s, 9H), 5.24 (s, 2H), 6.43 (t, 1H, J13=2.4 Hz), 6.84 (d, 2H, J13=2.4 Hz), 7.34-7.44 (m, 4H), 9.65 (brs, 2H).

Step 2: Synthesis of Monomer M-8 (Bis-Trimellitic Acid Anhydride Ester of 3,5-Dihydroxybenzoic Acid 4-Tert-Butylbenzyl Ester)

Intermediate I-8 (m=15.01 gr, 50 mmol, mw=300.36 g/mol), trimellitic anhydride chloride (m=23.16 gr, 110 mmol, mw=210.57 g/mol), and triethylamine (m=11.11 gr, 110 mol, mw=101.19 g/mol) are added to 0.5 L of acetonitrile and then, they are reacted in a similar method to that of Monomer M-1 to obtain a Monomer M-8 solution. The Monomer M-8 solution is filtered in a hot state to remove an insoluble material, concentrated down to 250 mL, and stored in a refrigerator for 48 hours.

A solid therefrom is filtered and then, twice crystallized with acetonitrile (200 mL) while acetic anhydride (10 mL) is added thereto. The product is dried under vacuum at 80° C. for 24 hours to obtain Monomer M-8 (m=18.34 gr, 28.3 mmol, mw=648.59 g/mol) in a white solid state (a yield: 56.6%).

$^1$H NMR (DMSO-d6) 300 MHz, δ, ppm: 1.27 (s, 9H), 5.37 (s, 2H), 7.43 (s, 4H), 7.88 (t, 1H, J13=2.1 Hz), 8.04 (d, 2H, J13=2.1 Hz), 8.29 (d, 2H, J13=8.1 Hz), 8.63-8.67 (m, 4H);

Thermal analysis: TGA (heating 10° C./min, N$_2$ atmosphere): 1 wt % loss (316.4° C.); and DSC (heating 10° C./min, N$_2$ atmosphere): mp=212.6° C.

Example 9: Synthesis of Monomer M-9

Compound M-9 is prepared according to Reaction Scheme M-9, and a method of preparing Intermediates I-9a and I-9b and Compound M-9 as a final product is respectively classified into Steps 1 to 3 and illustrated in detail as follows:

Reaction Scheme M-9

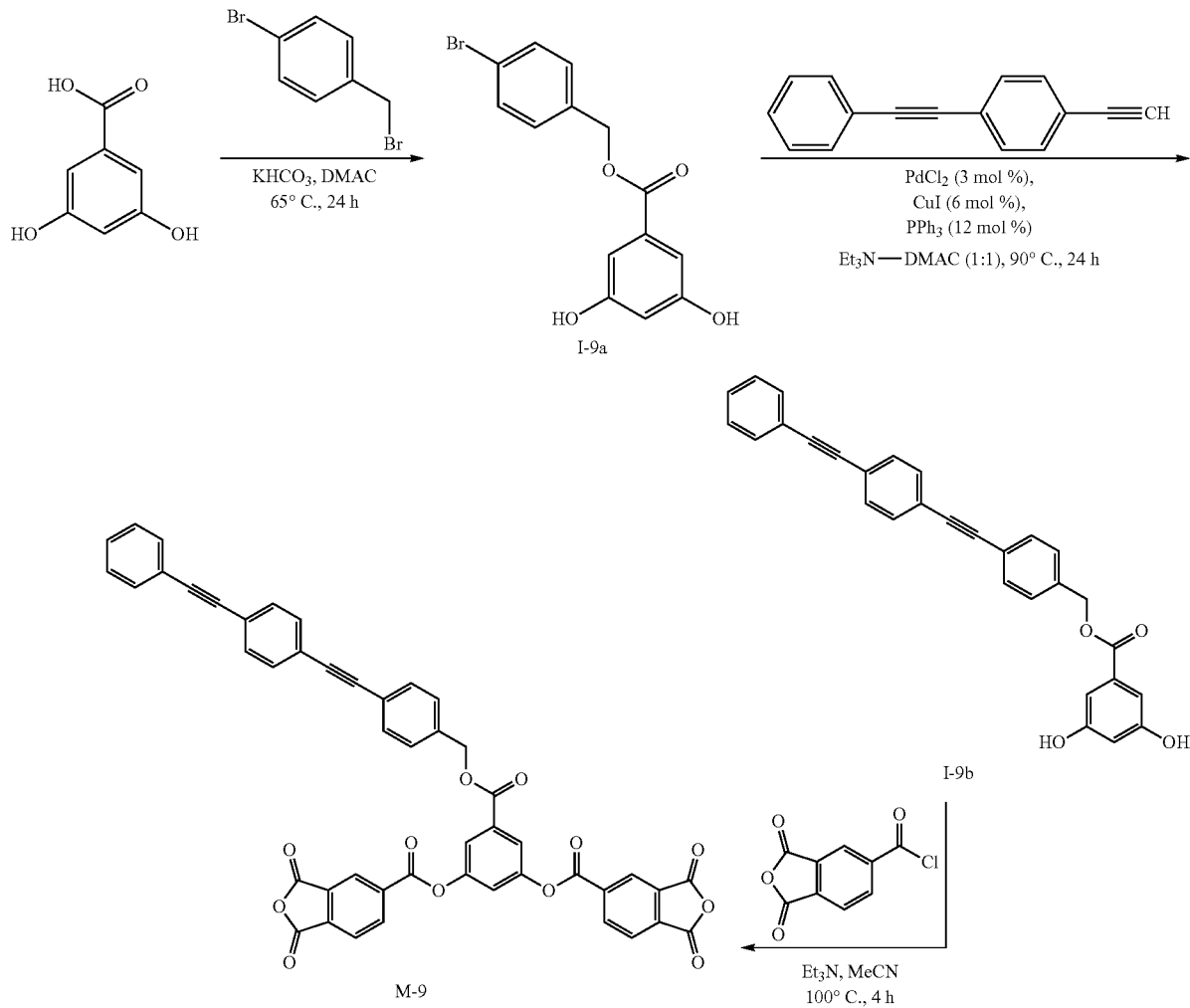

Product yields: I-9a, (DA#553, 98%), I-9b (DA#556, 45%), M-9 (DA#557, 61.3%)

Step 1: Synthesis of Intermediate I-9a
(3,5-dihydroxybenzoic acid 4-bromobenzyl ester)

3,5-dihydroxybenzoic acid (m=47.68 gr, 309.4 mmol, mw=154.13 g/mol), 1-bromo-4-bromomethylbenzene (m=77.32 gr, 309.4 mmol, mw=249.93 g/mol), and potassium hydrogen carbonate (m=62.1 gr, 620 mmol, mw=100.12 g/mol) are added to 500 mL of dimethyl acetamide, and then, the mixture is stirred under a nitrogen atmosphere at 65° C. for 24 hours. When a reaction is complete, the reactant is poured into 2 L of water, and the mixture is vigorously stirred. A precipitate therein is filtered, thoroughly washed with water, and dried under a reduced pressure at 80° C. for 24 hours to obtain Intermediate I-9a (m=98 gr, 303.3 mmol, mw=323.15 g/mol) in a white powder state (a yield: 98.0%).

$R_f$=0.27 (Eluent: ethylacetate:hexane=1:2, TLC silica gel 60 F254); and $^1$H NMR (DMSO-d6) 300 MHz, δ, ppm: 5.26 (s, 2H), 6.45 (dd, 1H, J13=2.1 Hz), 6.84 (d, 2H, J13=2.1 Hz), 7.40 (d, 2H, J12=8.4 Hz), 7.61 (d, 2H, J12=8.4 Hz), 9.65 (s, 2H, OH).

Step 2: Synthesis of Intermediate I-9b
(3,5-dihydroxybenzoic acid
4-(4-phenylethynyl-phenylethynyl)benzyl ester)

Intermediate I-9a (m=48.47 gr, 150 mmol, mw=323.15 g/mol) and 1-ethynyl-4-phenylethynylbenzene (m=30.34 gr, 150 mmol, mw=202.26 g/mol) are added to 600 mL of a mixed solvent of triethylamine and dimethyl acetamide (1:1) and dissolved therein in a 1 L 3-necked round-bottomed flask equipped with a nitrogen inlet and a condenser. The solution is stirred and purged with dry nitrogen gas for 1 hour, palladium (II) chloride (m=0.8 gr, 4.5 mmol, mw=177.33 g/mol), copper (I) iodide (m=1.71 gr, 9 mmol, mw=190.45 g/mol) and triphenylphosphine (m=4.72 gr, 18 mmol, mw=262.45 g/mol) are added thereto. After injecting nitrogen gas additionally for 10 minutes and closing the nitrogen outlet, the mixture is maintained under nitrogen at 80° C. for 24 hours while stirred. When a reaction is complete, a solution obtained by evaporating the triethylamine under a reduced pressure is poured into 2 L of water to obtain a brown solid. The solid is filtered and purified by being washed with water, suspended in 500 mL of DCM, boiled for 30 minutes, cooled down to room temperature, and is filtered again. This process is repeated three times. Herein, the first mother solution appears bright brown and includes some precipitate, the second mother solution appears light brown and includes tiny amount of precipitate, and the last mother solution appears light yellow. The obtained product in a light brown powder state is dried under vacuum at 75° C. for 24 hours to obtain Intermediate I-9b (m=30 gr, 67.5 mmol, mw=444.49 g/mol) in a light brown powder state (a yield: 45.0%).

$R_f$=0.72 (Eluent: ethylacetate:hexane=1:1, TLC silica gel 60 F254);

$^1$H NMR (DMSO-d6) 300 MHz, δ, ppm: 5.34 (s, 2H), 6.45 (dd, 1H, J13=2.1 Hz), 6.87 (d, 2H, J13=2.1 Hz), 7.43-7.64 (m, 13H), 9.66 (s, 2H, OH).

Step 3: Synthesis of Monomer M-9 (bis-trimellitic acid anhydride ester of 3,5-dihydroxybenzoic acid 4-(4-phenylethynyl-phenylethynyl)benzyl ester)

Intermediate I-9b (m=29.25 gr, 65.8 mmol, mw=444.49 g/mol), trimellitic anhydride chloride (m=30.4 gr, 144.8 mmol, mw=210.57 g/mol), and triethylamine (m=14.62 gr, 144.8 mol, mw=101.19 g/mol) are added to 1.5 L of acetonitrile, and they are reacted in a similar method to that of Monomer M-1 to synthesize a M-9 solution, charcoal is added to the solution, and the obtained mixture is filtered while hot. Then, when the mixture is cooled down to room temperature, a solid is precipitated. The product having low solubility in acetonitrile is suspended in 500 mL of acetonitrile and 20 mL of acetic anhydride, and then, boiled for 2 hours and cooled down to room temperature, and a solid therein is filtered and purified. This process is repeated twice. The crystallized solid is washed with a small amount of acetonitrile and dried under vacuum at 75° C. for 24 hours to obtain Monomer M-9 (m=32 gr, 40.4 mmol, mw=792.72 g/mol) in a yellow solid state (a yield: 61.3%).

$^1$H NMR (DMSO-d$_6$) 300 MHz, δ, ppm: 5.46 (s, 2H), 7.44-7.47 (m, 3H), 7.56-7.64 (m, 10H), 7.91 (dd, 1H, J$^{13}$=2.1 Hz), 8.08 (d, 2H, J$^{13}$=2.1 Hz), 8.29 (d, 2H, J$^{12}$=8.4 Hz), 8.62-8.68 (m, 4H);

HRMS APCI (m/z) for $C_{48}H_{24}O_{12}$: 712.1197 (measured mass), 792.1268 (calculated mass) for [M+H]$^+$;

Thermal analysis: TGA (heating 10° C./min, N$_2$ atmosphere): 1 wt % loss (316° C.); and DSC (heating 10° C./min, N$_2$ atmosphere): mp=225° C.

Example 10: Synthesis of Monomer M-10

Compound M-10 is prepared according to Reaction Scheme M-10, and a method of preparing Intermediate I-10 and Compound M-10 as a final product is classified into Steps 1 and 2 and illustrated in detail as follow:

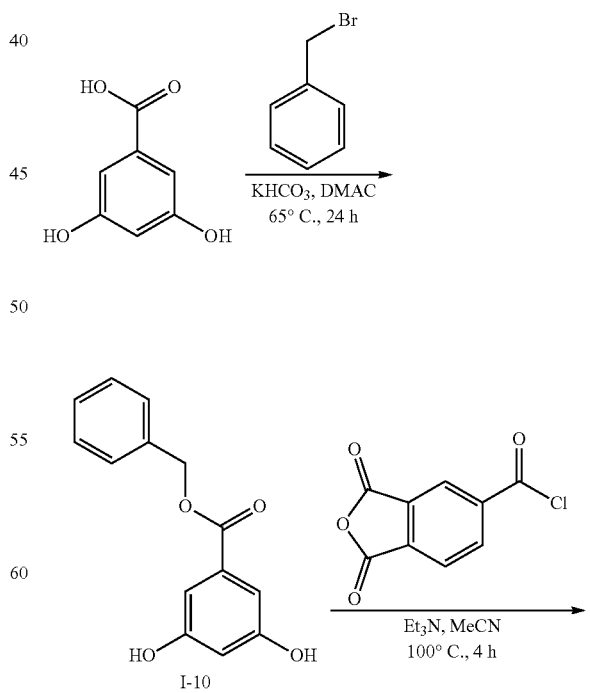

Reaction Scheme M-10

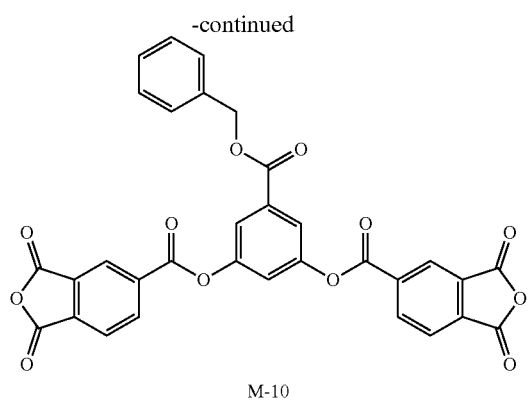

M-10

Step 1: Synthesis of Intermediate I-10 (3,5-dihydroxybenzoic acid benzyl ester)

3,5-dihydroxybenzoic acid (m=31.44 gr, 0.2 mol, mw=154.12 g/mol), benzyl bromide (m=34.2 gr, 0.2 mol, mw=171.04 g/mol), and potassium hydrogen carbonate (m=40 gr, 0.4 mol, mw=100.12 g/mol) are added to 0.3 L of dimethyl acetamide (DMAC) and then, they are reacted under a nitrogen atmosphere at 65° C. for 24 hours to synthesize a product in a similar method to that of Intermediate I-1, and the mixture is poured into 1 L of water to extract ethyl acetate as an oil-type precipitate. The ethyl acetate solution is washed with a 3% hydrochloric acid aqueous solution and water and then, dried with anhydrous magnesium sulfate. A solid obtained by evaporating a solvent under a reduced pressure is dried under vacuum at 100° C. to obtain Intermediate I-10 (m=48 gr, 196.52 mmol, mw=244.24 g/mol) in a white solid state (a yield: 98.3%).

$R_f$=0.34 (Eluent: ethylacetate:hexane=1:2, TLC silica gel 60 F254);

mp=130-132° C.; and $^1$H NMR (DMSO-d6) 300 MHz, δ, ppm: 5.29 (s, 2H), 6.44 (t, 1H, J13=2.4 Hz), 6.85 (d, 2H, J13=2.4 Hz), 7.33-7.47 (m, 5H), 9.64 (s, 2H).

Step 2: Synthesis of Monomer M-10 (bis-trimellitic acid anhydride ester of 3,5-dihydroxybenzoic acid benzyl ester)

Intermediate I-10 (m=30 gr, 122.8 mmol, mw=244.24 g/mol), trimellitic anhydride chloride (m=55.6 gr, 264 mmol, mw=210.57 g/mol), and triethylamine (m=26.7 gr, 264 mmol, mw=101.19 g/mol) are added to 0.8 L of acetonitrile, and then, they are reacted in a similar method to that of Monomer M-1 to synthesize Monomer M-10. The obtained solution is filtered while hot to remove an insoluble material, and a product therefrom is dissolved to obtain an acetonitrile solution. The acetonitrile solution is cooled down to precipitate a solid, and the solid is twice recrystallized with a mixed solvent of acetonitrile (300 mL) and acetic anhydride (20 mL) and dried under vacuum at 80° C. for 24 hours to obtain Monomer M-10 (m=23 gr, 38.8 mmol, mw=592.48 g/mol) as a yellow crystalline material (a yield: 31.6%).

$^1$H NMR (DMSO-d$_6$) 300 MHz, δ, ppm: 5.42 (s, 2H), 7.44-7.53 (m, 5H), 7.90 (t, 1H, $J^{13}$=2.1 Hz), 8.06 (d, 2H, $J^{13}$=2.1 Hz), 8.29 (d, 2H, $J^{12}$=8.4 Hz), 8.63-8.67 (m, 4H);

Thermal analysis: TGA (heating 10° C./min, N$_2$ atmosphere): 1 wt % loss (197.5° C.); and DSC (heating 10° C./min, N$_2$ atmosphere): mp~150° C. (decomposition).

Example 11: Synthesis of Monomer M-11

Compound M-11 is prepared according to Reaction Scheme M-11, and a method of preparing Intermediate I-11 and Compound M-11 as a final product is respectively classified into Steps 1 and 2 and illustrated in detail as follows:

Reaction Scheme M-11

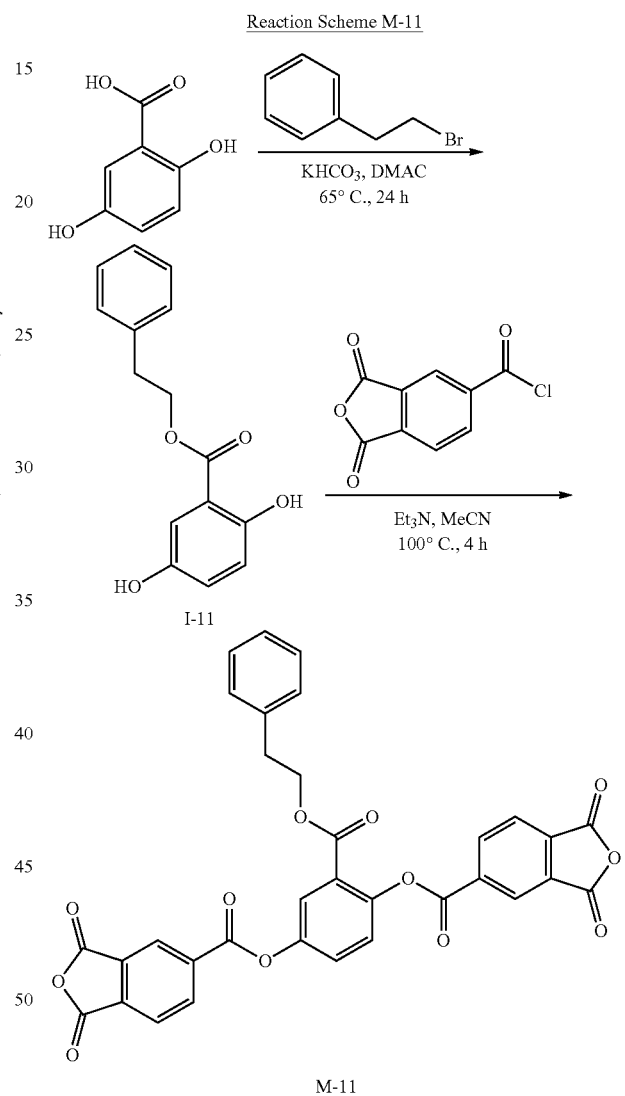

M-11

Step 1: Synthesis of Intermediate I-11 (2,5-dihydroxybenzoic acid 2-phenylethyl ester)

2,5-dihydroxybenzoic acid (m=18.14 gr, 117.68 mmol, mw=154.12 g/mol), 2-bromoethylbenzene (m=21.35 gr, 115.37 mol, mw=185.06 g/mol), and potassium hydrogen carbonate (m=23.4 gr, 230.74 mmol, mw=100.12 g/mol) are added to 0.1 L of dimethyl acetamide (DMAC), and they are reacted under a nitrogen atmosphere at 65° C. for 24 hours in a similar method to that of Intermediate I-1. The mixture is poured into 1 L of water, and a precipitate in an oil state gradually becomes solid. The product is filtered, washed with water, and dried at room temperature to obtain Intermediate I-11 (m=27.6 gr, 106.86 mmol, mw=258.27 g/mol) in a yellowish white solid state (a yield: 92.6%).

$R_f$=0.64 (Eluent: ethylacetate:hexane=1:2, TLC silica gel 60 $F_{254}$);

Mp=88-90° C.; and $^1$H NMR (DMSO-$d_6$) 300 MHz, δ, ppm: 3.04 (t, 2H, $J^{12}$=6.9 Hz), 4.50 (t, 2H, $J^{12}$=6.9 Hz), 6.81 (d, 1H, $J^{12}$=8.7 Hz), 6.97 (dd, 1H, $J^{12}$=8.7 Hz, $J^{13}$=3.0 Hz), 7.11 (d, 1H, $J^{13}$=3.0 Hz), 7.20-7.29 (m, 1H), 7.31-7.33 (m, 4H), 9.22 (s, 1H), 9.37 (s, 1H).

Step 2: Synthesis of Monomer M-11 (bis-trimellitic acid anhydride ester of 2,5-dihydroxybenzoic acid 2-phenylethyl ester)

Trimellitic anhydride chloride (m=47.94 gr, 227.7 mmol, mw=210.57 g/mol), Intermediate M-17 (m=27.35 gr, 105.9 mmol, mw=258.27 g/mol), and triethylamine (m=23 gr, 227.7 mmol, mw=101.19 g/mol) are added to 0.6 L of acetonitrile to obtain a Monomer M-11 solution in a similar method to that of Monomer M-1. The obtained solution is filtered while hot to remove an insoluble material, and an acetonitrile solution having a product dissolved therein is obtained. Then, a solid precipitated therein by cooling down the solution is twice recrystallized with a mixed solvent of acetonitrile (300 mL) and acetic anhydride (20 mL) and dried under vacuum at 80° C. for 24 hours to obtain Monomer M-11 (m=32 gr, 52.76 mmol, mw=606.50 g/mol) as a yellow crystalline material (a yield: 49.8%).

$^1$H NMR (DMSO-$d_6$) 300 MHz, δ, ppm: 2.86 (t, 2H, $J^{12}$=6.9 Hz), 4.38 (t, 2H, $J^{12}$=6.9 Hz), 7.14-7.27 (m, 5H), 7.67 (d, 1H, $J^{12}$=8.7 Hz), 7.85 (dd, 1H, $J^{12}$=8.7 Hz, $J^{13}$=3.0 Hz), 8.01 (d, 1H, $J^{13}$=3.0 Hz), 8.28-8.33 (m, 2H), 8.59-8.69 (m, 4H);

Thermal analysis: TGA (heating 10° C./min, $N_2$ atmosphere): 1 wt % loss (189° C.);

DSC (heating 10° C./min, $N_2$ atmosphere): mp=117.4° C. (decomposition).

Example 12: Synthesis of Monomer M-12

Compound M-12 is prepared according to Reaction Scheme M-12, and a method of preparing Intermediate I-12 and Compound M-12 as a final product is classified into Steps 1 and 2, and are illustrated in detail as follows:

Reaction Scheme M-12

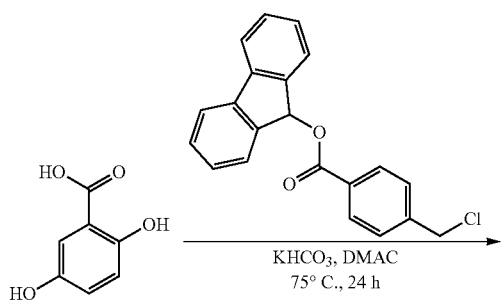

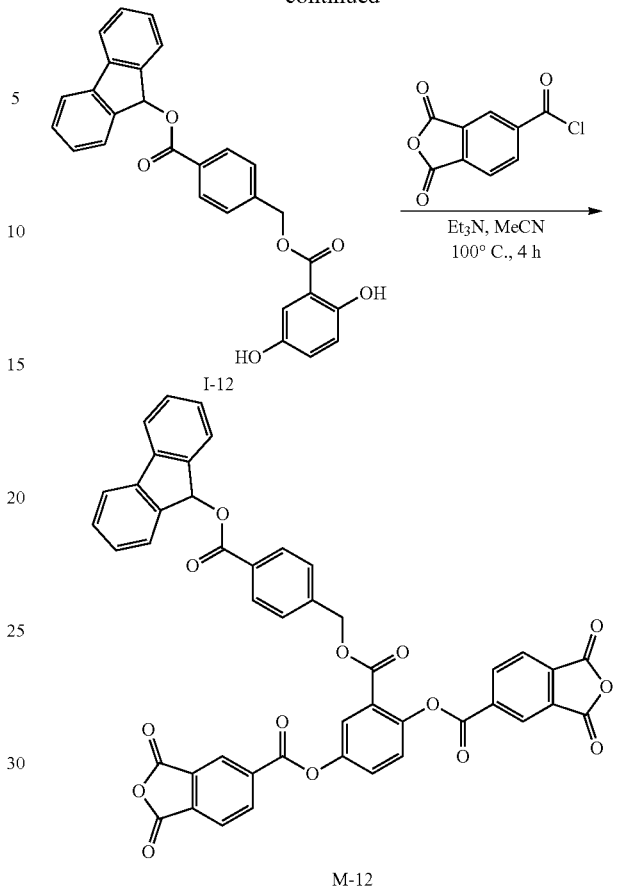

Step 1: Synthesis of Intermediate I-12 (2,5-dihydroxybenzoic acid 4-(9H-fluoren-9-yloxycarbonyl)benzyl ester)

Intermediate I-12 is synthesized in a similar method to that of Intermediate I-1 by adding 2,5-dihydroxybenzoic acid (m=3154.12 gr, 126.76 mmol, m=19.54 gr), 4-chloromethyl-benzoic acid 9H-fluoren-9-yl ester (mw=334.80 g/mol, 120.73 mmol, m=40.42 gr), and potassium hydrogen carbonate (mw=100.12 g/mol, 241.46 mmol, m=24.17 gr) to 0.2 L of dimethyl acetamide (DMAC) and reacting them under a nitrogen atmosphere at 75° C. for 24 hours. The product is poured into 1.5 L of water, and a white solid precipitated therein is filtered, washed with water, and crystallized from dichloromethane/isopropanol under a reduced pressure, and dried at 95° C. under a reduced pressure for 24 hours to obtain Intermediate I-12 (m=35 gr, mw=452.46 g/mol, 77.35 mmol) as a white crystalline solid (yield: 64.1%).

$R_f$=0.56 (Eluent: ethylacetate:hexane=1:2, TLC silica gel 60 $F_{254}$);

Mp=200-202° C.; and $^1$H NMR (DMSO-$d_6$) 300 MHz, δ, ppm: 5.44 (s, 2H), 6.83 (d, 1H, $J^{12}$=8.7 Hz), 6.97-7.00 (m, 2H), 7.18 (d, 1H, $J^{13}$=3.0 Hz), 7.35 (td, 2H, $J^{12}$=7.5 Hz, $J^{13}$=0.9 Hz), 7.49 (t, 2H, $J^{12}$=7.5 Hz), 7.63 (t, 4H, $J^{12}$=8.4 Hz), 7.89 (d, 2H, $J^{12}$=7.5 Hz), 8.02 (d, 2H, $J^{12}$=8.4 Hz), 9.21 (s, 1H), 9.85 (s, 1H).

Step 2: Synthesis of Monomer M-12 (bis-trimellitic acid anhydride ester of 2,5-dihydroxybenzoic acid 4-(9H-fluoren-9-yloxycarbonyl)benzyl ester)

Monomer M-12 is synthesized in a similar method to that of Monomer M-1 by adding trimellitic anhydride chloride (mw=210.57 g/mol, 101.83 mmol, m=21.44 gr), 2,5-dihydroxybenzoic acid 4-(9H-fluoren-9-yloxycarbonyl)benzyl ester (mw=452.47 g/mol, 47.36 mmol, m=21.43 gr), and triethylamine (mw=101.19 g/mol, 101.83 mmol, m=10.30 gr) to 1 L of acetonitrile and reacting them. When the reaction is complete, the solution is concentrated down to 0.4 L of a volume. When the concentrated solution is cooled down to room temperature, a precipitate is formed. The solid is filtered, washed with a small amount of water to remove triethylamine hydrochloride, and then, dried at 80° C. under a reduced pressure. A crude product therefrom is twice recrystallized with a mixture of acetonitrile (400 mL) and acetic anhydride (20 mL), charcoal is added to the second recrystallized solution, the mixture is filtered, the solvent of the filtrate is removed, and the residue is dried at 85° C. under a reduced pressure for 24 hours. Monomer M-12 is obtained therefrom as a bright yellow solid (m=14.49 gr, mw=800.70 g/mol, 18.1 mmol) (yield: 38.2%).

$^1$H NMR (DMSO-$d_6$) 300 MHz, δ, ppm: 5.27 (s, 2H), 6.93 (s, 1H), 7.32-7.51 (m, 6H), 7.63-7.66 (m, 3H), 7.77-7.88 (m, 6H), 8.15 (d, 2H, $J^{13}$=2.7 Hz), 8.20 (d, 1H, $J^{12}$=8.1 Hz), 8.27 (d, 1H, $J^{12}$=8.4 Hz), 8.44 (s, 1H), 8.52 (d, 1H, $J^{12}$=7.8 Hz), 8.64-8.66 (m, 2H);

Thermal analysis: TGA (heating 10° C./min, $N_2$ atmosphere): 1 wt % loss (154.4° C.); and DSC (heating 10° C./min, $N_2$ atmosphere): mp=170.3° C. (decomp.).

Example 13: Synthesis of Monomer M-13

Compound M-13 is prepared according to Reaction Scheme M-13, and a method of preparing Intermediate I-13 and Compound M-13 as a final product is classified into Steps 1 and 2 and illustrated in detail as follows:

Reaction Scheme M-13

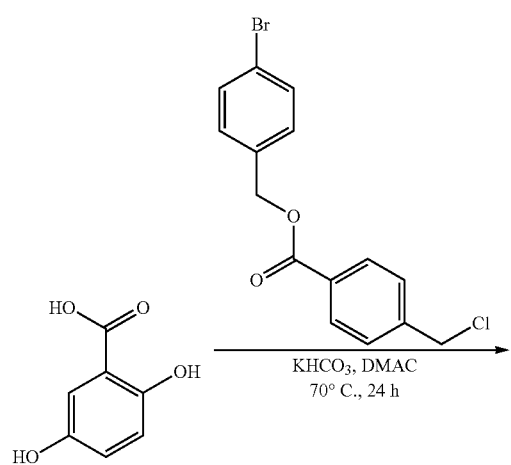

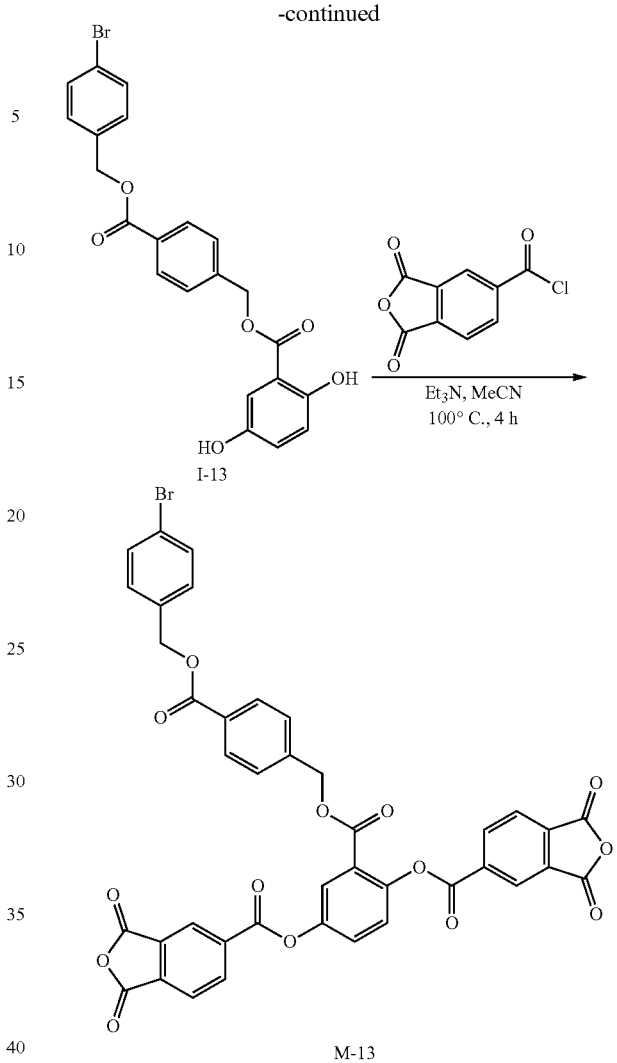

Step 1: Synthesis of Intermediate I-13 (2,5-dihydroxybenzoic acid 4-(4-bromobenzyloxycarbonyl)benzyl ester)

Intermediate I-13 is obtained in a similar method to that of Intermediate I-1 by adding 2,5-dihydroxybenzoic acid (mw=154.12 g/mol, 75.66 mmol, m=11.66 gr), 4-chloromethyl-benzoic acid 4-bromobenzyl ester (mw=339.62 g/mol, 75.66 mmol, m=25.69 gr), and potassium hydrogen carbonate (mw=100.12 g/mol, 151.32 mmol, m=15.15 gr) to 0.2 L dimethyl acetamide (DMAC), and reacting them at 70° C. under a nitrogen atmosphere for 24 hours. When the reaction is complete, the mixture is added to 1 L of water, a white solid produced therein is filtered, washed with water, crystallized with dichloromethane/methanol, and dried at 95° C. under a reduced pressure for 24 hours. Intermediate I-13 as the product is obtained as a white crystalline solid (yield: 90.2%), m=31.2 gr (mw=457.28 g/mol, 68.23 mmol).

$R_f$=0.46 (Eluent: ethylacetate:hexane=1:2, TLC silica gel 60 $F_{254}$); and mp=146-148° C. $^1$H NMR (DMSO-$d_6$) 300 MHz, δ, ppm: 5.34 (s, 2H), 5.45 (s, 2H), 6.83 (d, 1H, $J^{12}$=8.7 Hz), 6.98 (dd, 1H, $J^{12}$=9.0 Hz, $J^{13}$=3.0 Hz), 7.19 (d, 1H, $J^{13}$=3.0 Hz), 7.44

(d, 2H, $J^{12}$=8.4 Hz), 7.59-7.64 (m, 4H), 8.04 (d, 2H, $J^{12}$=8.4 Hz), 9.21 (s, 1H), 9.86 (s, 1H).

Step 2: Synthesis of Monomer M-13 (bis-trimellitic acid anhydride ester of 2,5-dihydroxybenzoic acid 4-(4-bromobenzyloxycarbonyl)benzyl ester)

Monomer M-13 is obtained in a similar method to that of Monomer M-1 by adding trimellitic anhydride chloride (mw=210.57 g/mol, 66.76 mmol, m=14.06 gr), 2,5-dihydroxybenzoic acid 4-(4-bromobenzyloxycarbonyl)benzyl ester (mw=457.28 g/mol, 31.05 mmol, m=14.20 gr), and trimethylamine (mw=101.19 g/mol, 66.76 mmol, m=6.74 gr) to 0.8 L of acetonitrile, and reacting them. When the reaction is complete, the solution is concentrated down to 0.4 L of a volume. When the solution is cooled down to room temperature, a precipitate is formed. The solid is filtered, washed with a small amount of water to remove the triethylamine hydrochloride, and then, dried at 80° C. under a reduced pressure. A crude product therefrom is recrystallized twice from a mixture of acetonitrile (300 mL) and acetic anhydride (20 mL), and then, charcoal is added to the second recrystallized solution, the mixture is filtered, the solvent of the filtrate is removed and the residue is dried at 85° C. for 24 hours. Monomer M-13 is obtained as a white solid. m=15.56 gr (mw=805.51 g/mol, 19.32 mmol), yield: 62.2%.

$^1$H NMR (DMSO-$d_6$) 300 MHz, δ, ppm: 5.28 (s, 2H), 5.29 (s, 2H), 7.38-7.45 (m, 4H), 7.61 (d, 2H, $J^{12}$=8.4 Hz), 7.66 (d, 1H, $J^{12}$=8.7 Hz), 7.76 (d, 2H, $J^{12}$=8.7 Hz), 7.85 (dd, 1H, $J^{12}$=8.7 Hz, $J^{13}$=2.7 Hz), 8.16-8.19 (m, 2H), 8.30 (d, 1H, $J^{12}$=8.1 Hz), 8.39 (s, 1H), 8.49 (d, 1H, $J^{12}$=8.1 Hz), 8.65-8.68 (m, 2H); and Thermal analysis: TGA (heating 10° C./min, $N_2$ atmosphere): 1 wt % loss (348.7° C.); DSC (heating 10° C./min, $N_2$ atmosphere): mp=227.5° C.

Example 14: Synthesis of Monomer M-14

Compound M-14 is prepared according to Reaction Scheme M-14, and a method of preparing Intermediate I-14 and Compound M-14 as a final product is respectively classified into Steps 1 and 2 and illustrated in detail as follows:

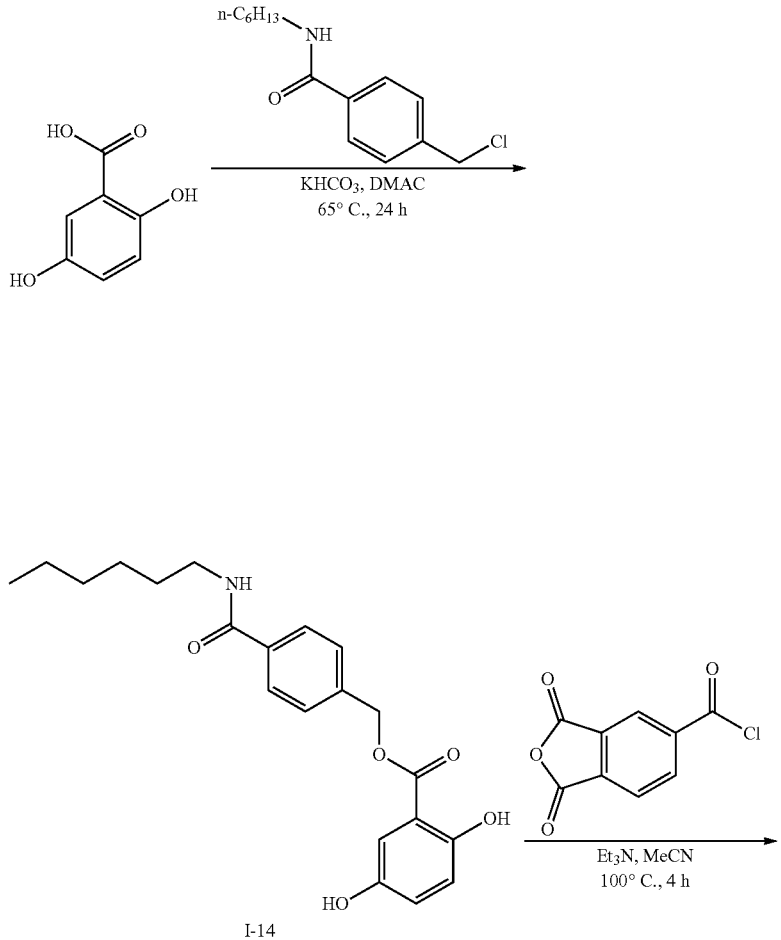

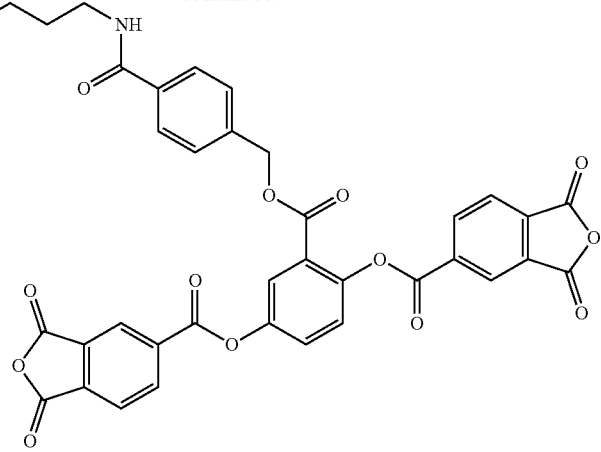

M-14

Step 1: Synthesis of Intermediate I-14 (2,5-dihydroxybenzoic acid 4-hexylcarbamoylbenzyl ester)

Intermediate I-14 is obtained in a similar method to that of Intermediate I-1 by adding 2,5-dihydroxybenzoic acid (mw=154.12 g/mol, 118.9 mmol, m=18.33 gr), 4-chloromethyl-N-n-hexylbenzamide (mw=253.77 g/mol, 115.5 mol, m=29.30 gr), and potassium hydrogen carbonate (mw=100.12 g/mol, 231 mmol, m=23.13 gr) to 0.2 L of dimethyl acetamide (DMAC), and reacting them at 65° C. under a nitrogen atmosphere for 24 hours. When the reaction is complete, the mixture is poured into 1.5 L of water, and a white solid precipitated therein is filtered, washed with water, crystallized from aqueous methanol, and dried at 95° C. under a reduced pressure for 24 hours. Intermediate I-14 produced therefrom is a white crystalline solid. $R_f$=0.21 (Eluent: ethylacetate:hexane=1:2, TLC silica gel 60 $F_{254}$), m=37.63 gr (mw=371.43 g/mol, 101.3 mmol), yield: 87.7%, mp=127-128° C.

$^1$H NMR (DMSO-$d_6$) 300 MHz, δ, ppm: 0.86 (t, 3H, $J^{12}$=6.9 Hz), 1.25-1.35 (m, 6H), 1.46-1.56 (m, 2H), 3.24 (dt, J=6 Hz, 6.9 Hz), 5.41 (s, 2H), 6.84 (d, 1H, $J^{12}$=8.7 Hz), 6.98 (dd, 1H, $J^{12}$=8.7 Hz, $J^{13}$=3.0 Hz), 7.18 (d, 1H, $J^{13}$=3.0 Hz), 7.55 (d, 1H, $J^{12}$=8.4 Hz), 7.86 (d, 1H, $J^{12}$=8.4 Hz), 8.46 (t, 1H, J=6 Hz, NH), 9.21 (s, 1H), 9.89 (s, 1H).

Step 2: Synthesis of Monomer M-14 (bis-trimellitic acid anhydride ester of 2,5-dihydroxybenzoic acid 4-hexylcarbamoylbenzyl ester)

Monomer M-14 is obtained in a similar method to that of Monomer M-1 by adding trimellitic anhydride chloride (mw=210.57 g/mol, 216.5 mmol, m=45.59 gr), Intermediate I-14 (2,5-dihydroxybenzoic acid 4-hexylcarbamoylbenzyl ester, mw=371.43 g/mol, 100.7 mmol, m=37.40 gr), and triethylamine (mw=101.19 g/mol, 216.5 mmol, m=21.87 gr) to 1 L of acetonitrile, and reacting them. The obtained solution is filtered while hot to remove an insoluble material and then, concentrated down to 0.5 L of a volume. Then, a crude product is precipitated by adding water thereto, filtered, and washed with water. The crude product is twice recrystallized with a mixture of acetonitrile (500 mL) and acetic anhydride (40 mL) and dried under vacuum at 95° C. for 24 hours to obtain Monomer M-14 as a white crystalline material. m=39 gr (mw=719.66 g/mol, 54.18 mmol), yield: 53.8%.

$^1$H NMR (DMSO-$d_6$) 300 MHz, δ, ppm: 0.85-0.90 (m, 3H), 1.29 (br s, 6H), 1.48-1.53 (m, 2H), 3.17-3.24 (m, 2H), 5.25 (s, 2H), 7.31 (d, 2H, $J^{12}$=8.4 Hz), 7.58 (d, 2H, $J^{12}$=8.4 Hz), 7.64 (d, 1H, $J^{12}$=8.7 Hz), 7.85 (dd, 1H, $J^{12}$=8.7 Hz, $J^{13}$=3.0 Hz), 8.12-8.17 (m, 2H), 8.28-8.35 (m, 3H), 8.44 (dd, 1H, $J^{12}$=8.1 Hz, $J^{14}$=1.2 Hz), 8.65-8.70 (m, 2H); and Thermal analysis: TGA (heating 10° C./min, $N_2$ atmosphere): 1 wt % loss (309.5° C.); DSC (heating 10° C./min, $N_2$ atmosphere): mp=207.2° C.

Example 15: Synthesis of Monomer M-15

Compound M-15 is prepared according to Reaction Scheme M-15, and a method of preparing Intermediate I-15 and Compound M-15 as a final product is respectively classified into Steps 1 and 2 and illustrated in detail as follows:

Reaction Scheme M-15

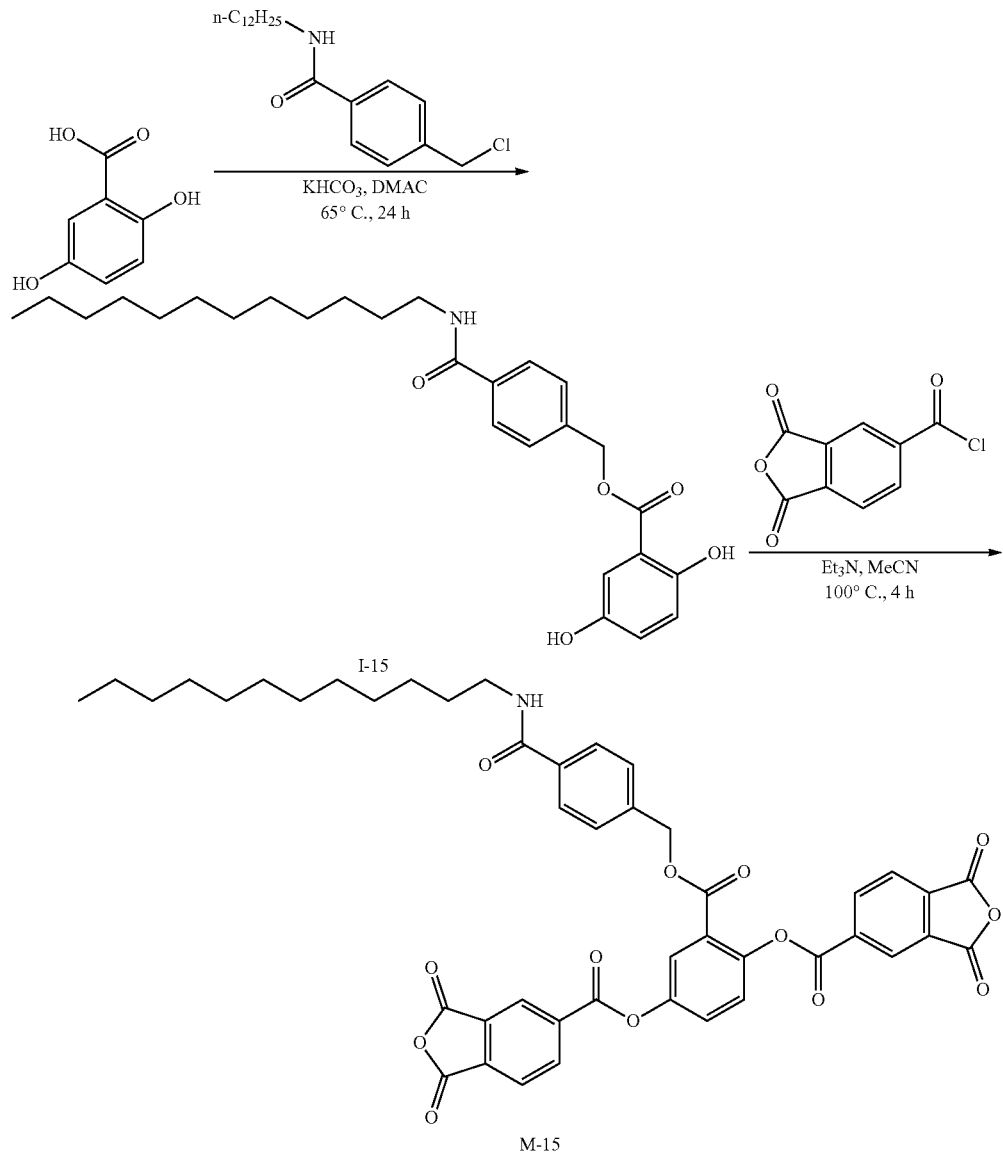

Step 1: Synthesis of Intermediate I-15 (2,5-dihydroxybenzoic acid 4-dodecylcarbamoylbenzyl ester)

Intermediate I-15 is obtained in a similar method to that of Intermediate I-1 by adding 2,5-dihydroxybenzoic acid (mw=154.12 g/mol, 101.1 mmol, m=15.58 gr), 4-chloromethyl-N-n-dodecylbenzamide (mw=337.94 g/mol, 98.15 mol, m=33.17 gr), and potassium hydrogen carbonate (mw=100.12 g/mol, 200 mmol, m=20.02 gr) to 0.2 L of dimethyl acetamide (DMAC) and reacting them under a nitrogen atmosphere at 65° C. for 24 hours. When the reaction is complete, the mixture is poured into 1.5 L of water, a white solid precipitated therein is filtered, washed with water, crystallized with 500 mL of methanol, and dried under a reduced pressure at 90° C. for 24 hours to obtain Intermediate I-15 as a white crystalline solid. $R_f$=0.24 (Eluent: ethylacetate:hexane=1:2, TLC silica gel 60 $F_{254}$), m=34.1 gr (mw=455.60 g/mol, 74.85 mmol), yield: 76.3%, mp=122-124° C.

$^1$H NMR (DMSO-$d_6$) 300 MHz, δ, ppm: 0.82-0.86 (m, 3H), 1.23-1.26 (m, 18H), 1.51 (t, 2H, $J^{12}$=6.3 Hz), 3.21-3.28 (m, 2H), 5.41 (s, 2H), 6.83 (d, 1H, $J^{12}$=9.0 Hz), 6.98 (dd, 1H, $J^{12}$=8.7 Hz, $J^{13}$=3.0 Hz), 7.19 (d, 1H, $J^{13}$=3.0 Hz), 7.54 (d, 2H, $J^{12}$=8.1 Hz), 7.86 (d, 2H, $J^{12}$=8.1 Hz), 8.46 (t, 1H, $J^{12}$=5.6 Hz), 9.20 (s, 1H), 9.89 (s, 1H).

Step 2: Synthesis of Monomer M-15 (bis-trimellitic acid anhydride ester of 2,5-dihydroxybenzoic acid 4-n-dodecylcarbamoylbenzyl ester)

Monomer M-15 is obtained in a similar method to that of Monomer M-1 by adding trimellitic anhydride chloride (mw=210.57 g/mol, 114.69 mmol, m=24.15 gr), Intermediate I-15 (2,5-dihydroxybenzoic acid 4-dodecylcarbamoylbenzyl ester) (mw=455.60 g/mol, 54.61 mmol, m=24.88 gr), and triethylamine (mw=101.19 g/mol, 117.40 mmol, m=11.88 gr) to 1.2 L of acetonitrile, and reacting them. When the reaction is complete, the solution is filtered to remove an insoluble material and then, concentrated down to 0.4 L of a volume and allowed to stand for 2 days to form a precipitate. The solid is filtered and washed with a small amount of acetonitrile. A crude product therefrom is twice recrystallized with a mixture of acetonitrile (300 mL) and acetic anhydride (15 mL), charcoal is added to the second recrystallized solution, the mixture is filtered, the solvent of the filtrate is removed and the residue is dried at 85° C. under vacuum for 24 hours to obtain Monomer M-15 in a white solid state. m=10.28 gr (mw=803.83 g/mol, 12.78 mmol), yield: 23.4%.

$^1$H NMR (DMSO-$d_6$) 300 MHz, δ, ppm: 0.82-0.87 (m, 3H), 1.20-1.30 (m, 18H), 1.50 (m, 2H), 3.17-3.21 (m, 2H), 5.24 (s, 2H), 7.31 (d, 2H, $J^{12}$=8.1 Hz), 7.57 (d, 2H, $J^{12}$=8.4 Hz), 7.64 (d, 2H, $J^{12}$=9.0 Hz), 7.85 (dd, 1H, $J^{12}$=8.7 Hz, $J^{13}$=2.7 Hz), 8.12-8.17 (m, 2H), 8.28-8.35 (m, 3H), 8.44 (dd, 1H, $J^{12}$=7.8 Hz, $J^{13}$=1.2 Hz), 8.65-8.68 (m, 2H).

Thermal analysis: TGA (heating 10° C./min, $N_2$ atmosphere): 1 wt % loss (317.2° C.); DSC (heating 10° C./min, $N_2$ atmosphere): mp=172.3° C.

Example 16: Synthesis of Monomer M-16

Compound M-16 is prepared according to Reaction Scheme M-16, and a method of preparing Intermediate I-16 and Compound M-16 as a final product is respectively classified into Steps 1 and 2, and illustrated in detail as follows:

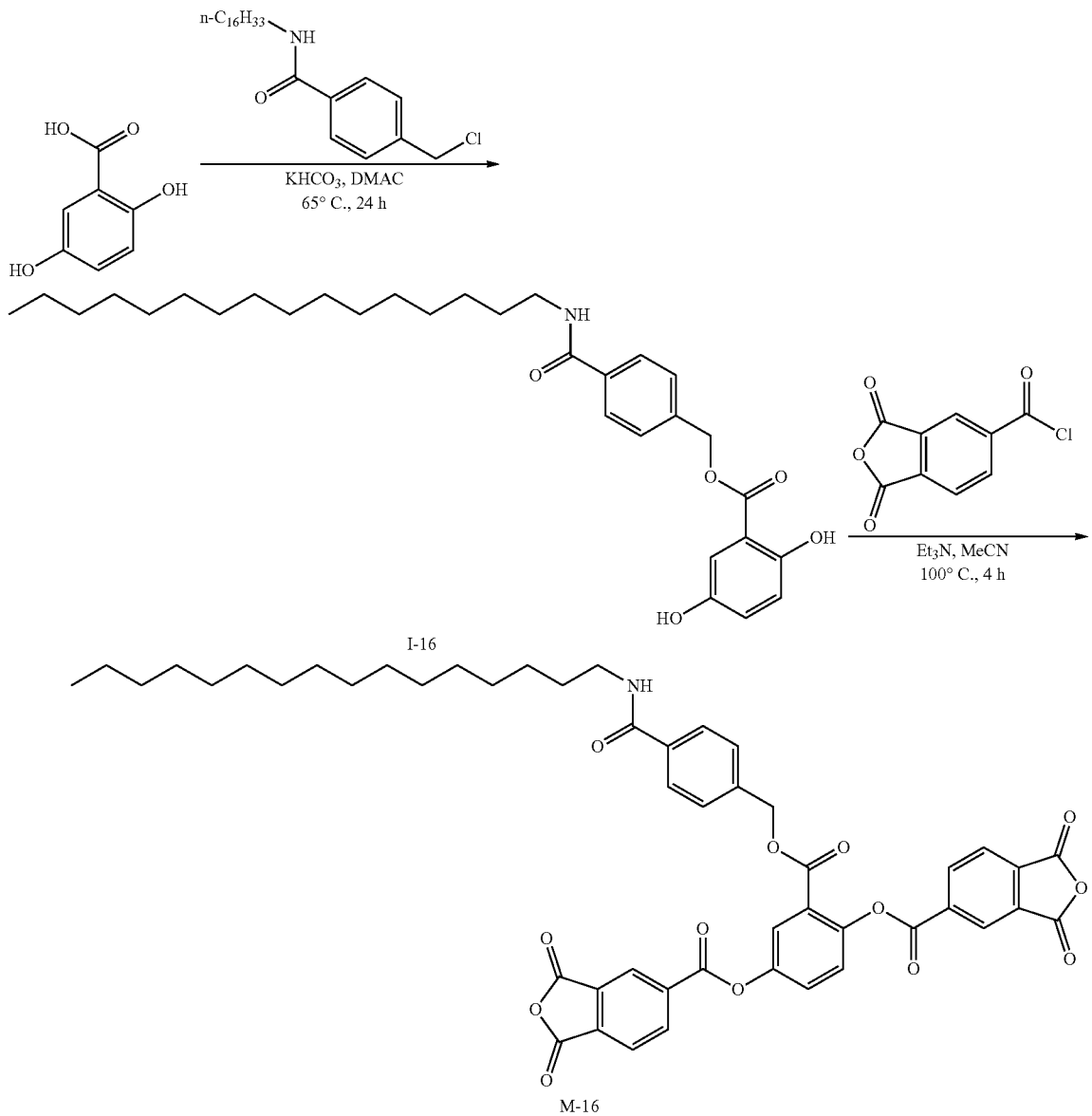

Step 1: Synthesis of Intermediate I-16 (2,5-dihydroxybenzoic acid 4-hexadecylcarbamoylbenzyl ester)

Intermediate I-16 is obtained in a similar method to that of Intermediate I-1 by adding 2,5-dihydroxybenzoic acid (mw=154.12 g/mol, 198.93 mmol, m=30.66 gr), 4-chloromethyl-N-n-hexadecylbenzamide (mw=394.04 g/mol, 195.03 mol, m=76.85 gr), and potassium hydrogen carbonate (mw=100.12 g/mol, 390.06 mmol, m=39.05 gr) to 0.5 L of dimethyl acetamide (DMAC), and reacting them under a nitrogen atmosphere at 65° C. for 24 hours. When the reaction is complete, the mixture is poured into 3 L of water, and a white solid precipitated therein is filtered and washed with water. A crude product therefrom is suspended in hot water at 80° C. and then, stirred for 30 minutes and filtered. A resulting solid is dried for 24 hours and then, at 90° C. under a reduced pressure for 24 hours. The product is obtained as a white solid. $R_f$=0.30 (Eluent: ethylacetate:hexane=1:2, TLC silica gel 60 $F_{254}$), m=95.4 gr (mw=511.7 g/mol, 186.44 mmol), yield: 95.6%, mp=118-120° C.

$^1$H NMR (DMSO-$d_6$) 300 MHz, δ, ppm: 0.82-0.87 (m, 3H), 1.16-1.27 (m, 26H), 1.48-1.52 (m, 2H), 3.21-3.29 (m, 2H), 5.41 (s, 2H), 6.83 (dd, 1H, $J^{12}$=9.0 Hz, $J^{13}$=3.0 Hz), 7.19 (d, 1H, $J^{13}$=3.0 Hz), 7.54 (d, 2H, $J^{12}$=8.1 Hz), 7.86 (d, 2H, $J^{12}$=8.1 Hz), 8.46 (t, 1H, $J^{12}$=5.6 Hz), 9.21 (s, 1H), 9.90 (s, 1H).

Step 2: Synthesis of Monomer M-16 (bis-trimellitic acid anhydride ester of 2,5-dihydroxybenzoic acid 4-n-hexadecylcarbamoylbenzyl ester)

Monomer M-16 is prepared in a similar method to that of Monomer M-1 by adding trimellitic anhydride chloride (mw=210.57 g/mol, 390.28 mmol, m=82.18 gr), Intermediate I-16 (2,5-dihydroxybenzoic acid 4-n-hexadecylcarbamoylbenzyl ester, mw=511.70 g/mol, 185.85 mmol, m=95.1 gr), and triethylamine (mw=101.19 g/mol, 408.87 mmol, m=41.37 gr) to 1.5 L of acetonitrile, and reacting them. When the reaction is complete, the obtained solution is filtered to remove an insoluble material and concentrated down to 0.5 L of a volume and then, diluted with 1.5 L of water. The solid is filtered and washed with water. Then, a solid obtained therefrom is dried for 24 hours in the air and then, at 80° C. under a reduced pressure for 24 hours. A crude product is twice recrystallized with a mixture of acetonitrile (600 mL) and acetic anhydride (100 mL) and then, dried under vacuum at 80° C. for 24 hours by adding charcoal during the second recrystallization. A product of Monomer M-16 is obtained as a white solid. m=88.7 gr (mw=859.94 g/mol, 103.15 mmol), yield: 55.5%.

$^1$H NMR (CDCl$_3$) 300 MHz, δ, ppm: 0.87-0.92 (m, 3H), 1.16-1.36 (m, 26H), 1.60-1.64 (m, 2H), 3.41-3.48 (m, 2H), 5.24 (s, 2H), 6.13 (t, 1H, J=5.4 Hz), 7.25-7.38 (m, 3H), 7.51-7.63 (m, 3H), 8.04-8.10 (m, 2H), 8.22 (d, 1H, $J^{12}$=8.1 Hz), 8.53-8.56 (m, 2H), 8.75 (dd, 1H, $J^{12}$=8.1 Hz, $J^{13}$=1.5 Hz), 8.84 (s, 1H).

Thermal analysis: TGA (heating 10° C./min, N$_2$ atmosphere): 1 wt % loss (263.4° C.); DSC (heating 10° C./min, N$_2$ atmosphere): mp=155.0° C.

Example 17: Synthesis of Monomer M-17

Compound M-17 is prepared according to Reaction Scheme M-17, and a method of preparing Intermediate I-17 and Compound M-17 as a final product is respectively classified into Steps 1 and 2 and illustrated in detail as follow:

Reaction Scheme M-17

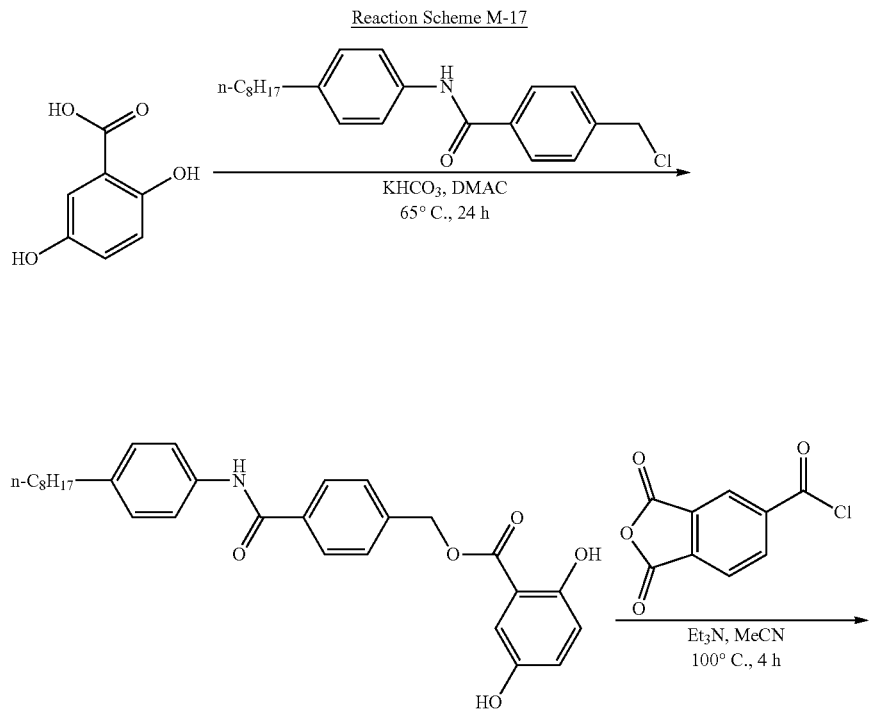

I-17

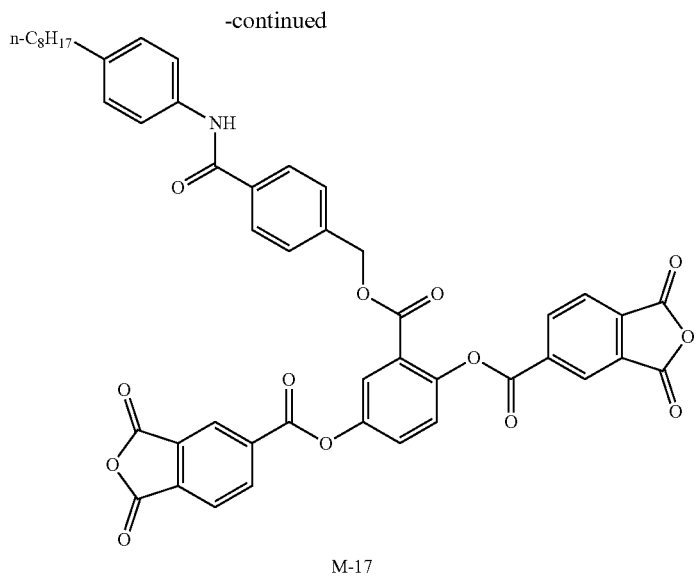

M-17

Step 1: Synthesis of Intermediate I-17 (2,5-dihydroxybenzoic acid 4-(4-octylphenylcarbamoyl)benzyl ester (1:2 mixture of conformers))

Intermediate I-17 is prepared in a similar method to that of Intermediate I-1 by adding 2,5-dihydroxybenzoic acid (mw=154.12 g/mol, 117.12 mmol, m=18.05 gr), 4-chloromethyl-N-(4-octylphenyl)benzamide) (mw=357.93 g/mol, 113.71 mol, m=40.7 gr), and potassium hydrogen carbonate (mw=100.12 g/mol, 227 mmol, m=22.72 gr) to 0.3 L dimethyl acetamide (DMAC), and reacting them under a nitrogen atmosphere at 65° C. for 24 hours. When the reaction is complete, a white solid is precipitated by pouring the mixture into 1.5 L of water, and is twice purified by being filtered and washed with water and then, being re-suspended in 0.5 L of methanol and boiling the suspension, cooled it down to room temperature, and filtering it. A product therefrom is dried at 80° C. under a reduced pressure for 24 hours and obtained as a white solid. $R_f$=0.38 (Eluent: ethylacetate:hexane=1:2, TLC silica gel 60 $F_{254}$), m=44.87 gr (mw=475.59 g/mol, 94.35 mmol), yield 83%. Mp=136° C.

$^1$H NMR (DMSO-$d_6$) 300 MHz, δ, ppm: 0.85 (t, 4.5H, J=6.7 Hz), 1.20-1.30 (m, 15H), 1.50-1.60 (m, 3H), 2.50-2.55 (m, 3H), 4.84 (s, 1H, CH$_2$), 5.45 (s, 2H, CH$_2$), 6.85 (d, 1H, J$^{12}$=8.7 Hz), 6.99 (dd, 1H, J$^{12}$=9.0 Hz, J$^{13}$=3.0 Hz), 7.15 (d, 3H, J$^{12}$=8.4 Hz), 7.20 (d, 1H, J$^{12}$=3.0 Hz), 7.57-7.68 (m, 6H), 7.93-7.99 (m, 3H), 9.24 (s, 1H), 9.90 (br s, 1H), 10.19 (s, 1.5H).

Step 2: Synthesis of Monomer M-17 (bis-trimellitic acid anhydride ester of 2,5-dihydroxybenzoic acid 4-(4-octylphenylcarbamoyl)benzyl ester)

Monomer M-17 is obtained in a similar method to that of Monomer M-1 by adding trimellitic anhydride chloride (mw=210.57 g/mol, 196.5 mmol, m=41.38 gr), Intermediate I-17 (2,5-dihydroxybenzoic acid 4-(4-octylphenylcarbamoyl)benzyl ester, mw=475.59 g/mol, 93.67 mmol, m=44.5 gr), and triethylamine (mw=101.19 g/mol, 205.85 mmol, m=20.83 gr) to 1 L of acetonitrile, and reacting them. When the reaction is complete, the obtained brown solution is filtered while hot to remove an insoluble material and cooled down to room temperature. A solid immediately starts to precipitate in a hot solution state. The solid is filtered and washed with a small amount of acetonitrile. A crude product is purified by suspending the solid with a mixture of acetonitrile (800 mL) and acetic anhydride (50 mL) and boiling the suspension and subsequently, cooled down to room temperature and filtered. The obtained product is dried at 100° C. under vacuum for 24 hours. The product is Monomer M-17 of a yellowish crystalline solid. m=32.77 gr (mw=823.82 g/mol, 39.78 mmol), yield: 42.5%.

$^1$H NMR (DMSO-$d_6$) 300 MHz, δ, ppm: 0.85 (m, 3H), 1.20-1.30 (m, 10H), 1.50-1.60 (m, 2H), 2.50-2.57 (m, 2H), 5.29 (s, 2H, CH$_2$), 7.15 (d, 1H, J$^{12}$=8.7 Hz), 7.40 (d, 1H, J$^{12}$=8.1 Hz), 7.61-7.72 (m, 5H), 7.83-7.88 (m, 1H), 8.17-8.19 (m, 2H), 8.29 (d, 1H, J$^{12}$=8.4 Hz), 8.39-8.40 (m, 1H), 8.47-8.50 (m, 1H), 8.65-8.69 (m, 1H), 10.06 (s, 1H, NH). Thermal analysis: TGA (heating 10° C./min, N$_2$ atmosphere): 1 wt % loss (320.3° C.); DSC (heating 10° C./min, N$_2$ atmosphere): mp=230.1° C.

Example 18: Synthesis of Monomer M-18

Compound M-18 is prepared according to Reaction Scheme M-18, and a method of preparing Intermediate I-18 and Compound M-18 as a final product is respectively classified into Steps 1 and 2 and illustrated in detail as follows:

Reaction Scheme M-18

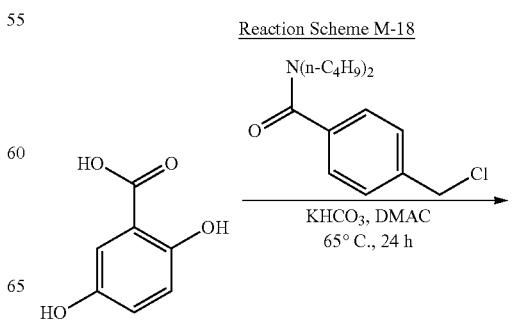

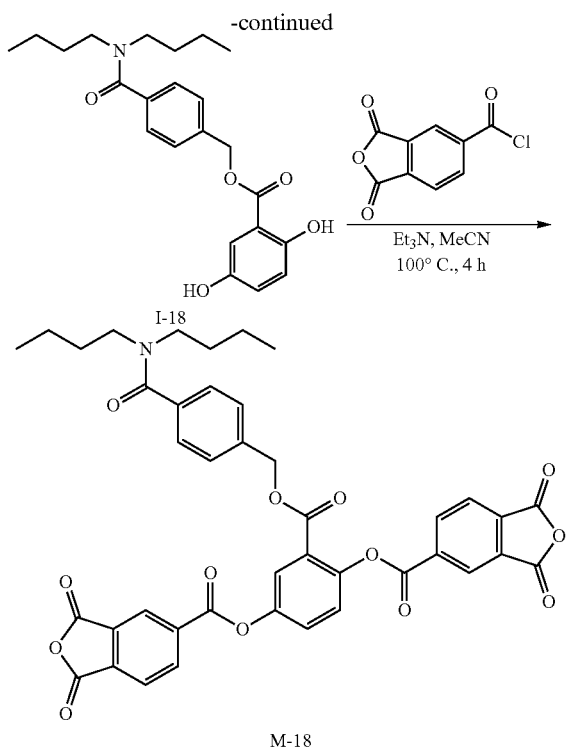

I-18

M-18

Step 1: Synthesis of Intermediate I-18 (2,5-dihydroxybenzoic acid 4-N,N-dibutylcarbamoylbenzyl ester)

Intermediate I-18 is synthesized in a similar method to that of Intermediate I-1 by adding 2,5-dihydroxybenzoic acid (mw=154.12 g/mol, 99.35 mmol, m=15.31 gr), N,N-dibutyl-4-chloromethylbenzamide (mw=281.83 g/mol, 99.35 mol, m=33.17 gr), and potassium hydrogen carbonate (mw=100.12 g/mol, 200 mmol, m=20.02 gr) to 0.2 L of dimethyl acetamide (DMAC), and reacting them under a nitrogen atmosphere at 65° C. for 24 hours. When the reaction is complete, the mixture is poured into 1.5 L of water, a white sticky solid precipitated therein is filtered, washed with water, dried, and crystallized with about 400 mL of hexane/dichloromethane. A white crystalline material obtained therefrom is filtered, washed with hexane, and dried at 80° C. under a reduced pressure for 24 hours. A final product therefrom is a white crystalline solid. $R_f$=0.23 (Eluent: ethylacetate:hexane=1:2, TLC silica gel 60 $F_{254}$), m=31.4 gr (mw=399.49 g/mol, 78.60 mmol), yield: 79.1%, mp=117-119° C.

$^1$H NMR (DMSO-$d_6$) 300 MHz, δ, ppm: 0.65-0.75 (m, 3H), 0.88-0.98 (m, 3H), 1.00-1.12 (m, 2H), 1.27-1.37 (m, 2H), 1.39-1.49 (m, 2H), 1.51-1.61 (m, 2H), 3.09-3.19 (m, 2H), 3.35-3.45 (m, 2H), 5.40 (s, 2H), 6.83 (d, 1H, $J^{12}$=9.0 Hz), 6.98 (dd, 1H, $J^{12}$=9.0 Hz, $J^{13}$=3.0 Hz), 7.19 (d, 1H, $J^{13}$=3.0 Hz), 7.36 (d, 2H, $J^{12}$=8.4 Hz), 7.53 (d, 2H, $J^{12}$=8.4 Hz), 9.24 (br s, 1H), 9.89 (br s, 1H).

Step 2: Synthesis of Monomer M-18 (bis-trimellitic acid anhydride ester of 2,5-dihydroxybenzoic acid 4-N,N-dibutylcarbamoylbenzyl ester)

Monomer M-18 is prepared in a similar method to that of Monomer M-1 by adding trimellitic anhydride chloride (mw=210.57 g/mol, 164.13 mmol, m=34.56 gr), Intermediate I-18 (2,5-dihydroxybenzoic acid 4-N,N-dibutylcarbamoylbenzyl ester, mw=399.49 g/mol, 78.15 mmol, m=31.22 gr), and triethylamine (mw=101.19 g/mol, 168 mmol, m=17 gr) to 1 L of acetonitrile, and reacting them. When the reaction is complete, the obtained brown solution is filtered while hot to remove an insoluble material and then, concentrated down to 0.4 L of a volume. From the hot solution, a white solid is almost immediately precipitated. The solid is filtered and washed with a small amount of acetonitrile. A crude product therefrom is twice recrystallized from a mixture of acetonitrile (500 mL) and acetic anhydride (30 mL) and dried under vacuum at 85° C. for 24 hours to obtain Monomer M-18 as a white crystalline solid. m=35.09 gr (mw=747.72 g/mol, 46.93 mmol), yield: 60.5%.

$^1$H NMR (DMSO-$d_6$) 300 MHz, δ, ppm: 0.62-0.72 (m, 3H), 0.90-1.08 (m, 5H), 1.25-1.60 (m, 6H), 3.00-3.10 (m, 2H), 3.35-3.45 (m, 2H), 5.24 (s, 2H), 7.11 (d, 2H, $J^{12}$=8.1 Hz), 7.32 (d, 2H, $J^{12}$=8.1 Hz), 7.65 (d, 1H, $J^{12}$=8.7 Hz), 7.85 (dd, 1H, $J^{12}$=9.0 Hz, $J^{13}$=3.0 Hz), 8.15 (d, 1H, $J^{13}$=3.0 Hz), 8.19 (d, 1H, $J^{12}$=7.8 Hz), 8.29 (d, 1H, $J^{12}$=8.4 Hz), 8.40 (br s, 1H), 8.49 (dd, 1H, $J^{12}$=7.8 Hz, $J^{13}$=1.5 Hz), 8.65-8.68 (m, 2H).

Thermal analysis: TGA (heating 10° C./min, $N_2$ atmosphere): 1 wt % loss (332.8° C.); DSC (heating 10° C./min, $N_2$ atmosphere): mp=180.0° C.

Example 19: Synthesis of Monomer M-19

Compound M-19 is prepared according to Reaction Scheme M-19, and a method of preparing Intermediate I-19 and Compound M-19 as a final product is respectively classified into Steps 1 and 2 and illustrated in detail as follows:

Reaction Scheme M-19

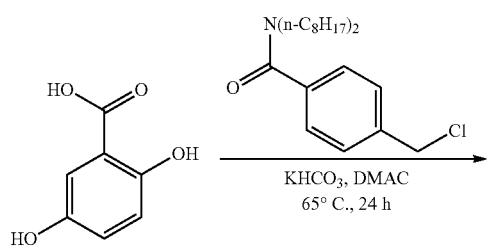

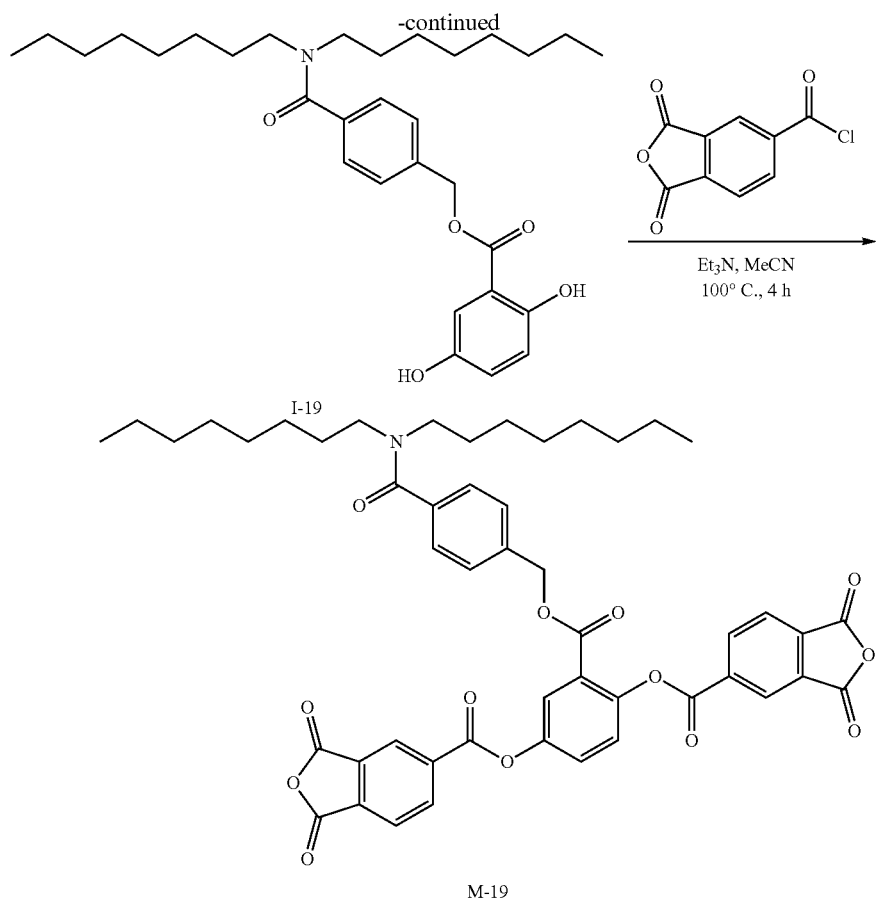

Step 1: Synthesis of Intermediate I-19 (2,5-dihydroxybenzoic acid 4-N,N-dioctylcarbamoylbenzyl ester)

Intermediate I-19 is synthesized in a similar method to that of Intermediate I-1 by adding 2,5-dihydroxybenzoic acid (mw=154.12 g/mol, 166.57 mmol, m=25.67 gr), N,N-dioctyl-4-chloromethylbenzamide (mw=394.04 g/mol, 163.31 mol, m=64.35 gr), and potassium hydrogen carbonate (mw=100.12 g/mol, 326.62 mmol, m=32.70 gr) to 0.35 L of dimethyl acetamide (DMAC), and reacting them under a nitrogen atmosphere at 65° C. for 24 hours. When the reaction is complete, the mixture is poured into 2 L of water, and oil precipitated therein is extracted with 1 L of ethyl acetate. An organic layer therefrom is three times washed with aqueous hydrocarbon and water, and then, dried with aqueous sodium sulfate. The ethyl acetate is evaporated under a reduced pressure, and then, an oily residue is dissolved in hot hexane (0.7 L), treated with silica gel, and then, filtered while hot to remove impurities. The hexane is evaporated under a reduced pressure to obtain a colorless sticky oily product. $R_f$=0.48 (Eluent: ethylacetate:hexane=1:2, TLC silica gel 60 $F_{254}$), m=67.8 gr (mw=511.71 g/mol, 132.50 mmol), yield: 81.1%.

$^1$H NMR (DMSO-$d_6$) 300 MHz, δ, ppm: 0.80-0.86 (m, 6H), 1.03-1.56 (m, 20H), 1.44-1.56 (m, 4H), 3.13 (s, 2H), 3.29 (s, 2H), 5.40 (s, 2H), 6.83 (d, 1H, $J^{12}$=9.0 Hz), 6.98 (dd, 1H, $J^{12}$=9.0 Hz, $J^{13}$=3.0 Hz), 7.19 (d, 1H, $J^{13}$=3.0 Hz), 7.36 (d, 2H, $J^{12}$=8.4 Hz), 7.53 (d, 2H, $J^{12}$=8.4 Hz), 9.20 (s, 1H), 9.91 (s, 1H).

Step 2: Synthesis of Monomer M-19 (bis-trimellitic acid anhydride ester of 2,5-dihydroxybenzoic acid 4-N,N-dioctylcarbamoylbenzyl ester)

Monomer M-19 is synthesized in a similar method to that of Monomer M-1 by adding trimellitic anhydride chloride (mw=210.57 g/mol, 277.43 mmol, m=58.24 gr), Intermediate I-19 (2,5-dihydroxybenzoic acid 4-N,N-dioctylcarbamoylbenzyl ester, mw=511.71 g/mol, 132.11 mmol, m=67.6 gr), and triethylamine (mw=101.19 g/mol, 290.64 mmol, m=29.41 gr) to 1.2 L of acetonitrile, and reacting them. When the reaction is complete, a brown solution is filtered while hot to remove an insoluble material and concentrated down to 0.5 L of a volume. The solution is cooled down to room temperature to precipitate a white solid. The solid is filtered and washed with a small amount of acetonitrile. A crude product therefrom is twice recrystallized with a mixed solvent of acetonitrile (600 mL) and acetic anhydride (30 mL), and decolorizing charcoal is added thereto during the second recrystallization. A product therefrom is dried under vacuum at 90° C. for 24 hours to obtain Monomer M-19 of a white crystalline solid as a final product. m=71.4 gr (mw=859.94 g/mol, 83.03 mmol), yield: 62.8%.

$^1$H NMR (CDCl$_3$) 300 MHz, δ, ppm: 0.82-0.91 (m, 6H), 1.09-1.63 (m, 24H), 3.08-3.14 (m, 2H), 3.41-3.47 (m, 2H), 5.23 (s, 2H), 7.15 (d, 2H, $J^{12}$=8.1 Hz), 7.29 (d, 2H, $J^{12}$=8.1 Hz), 7.36 (d, 1H, $J^{12}$=8.7 Hz), 7.60 (dd, 1H, $J^{12}$=9.0 Hz, $J^{13}$=3.0 Hz), 8.06 (d, 1H, $J^{13}$=3.0 Hz), 8.11 (d, 1H, $J^{12}$=7.8 Hz), 8.22 (d, 1H, $J^{12}$=8.1 Hz), 8.53 (dd, 1H, $J^{12}$=7.8 Hz, $J^{13}$=1.5 Hz), 8.59 (s, 1H), 8.76 (dd, 1H, $J^{12}$=8.1 Hz, $J^{13}$=1.5 Hz), 8.85 (s, 1H).

Thermal analysis: TGA (heating 10° C./min, N$_2$ atmosphere): 1 wt % loss (293° C.); DSC (heating 10° C./min, N$_2$ atmosphere): mp=182.7° C.

Example 20: Synthesis of Monomer M-20

Compound M-20 is prepared according to Reaction Scheme M-20, and a method of preparing Intermediate I-20 and Compound M-20 as a final product is respectively classified into Steps 1 and 2 and illustrated in detail as follows:

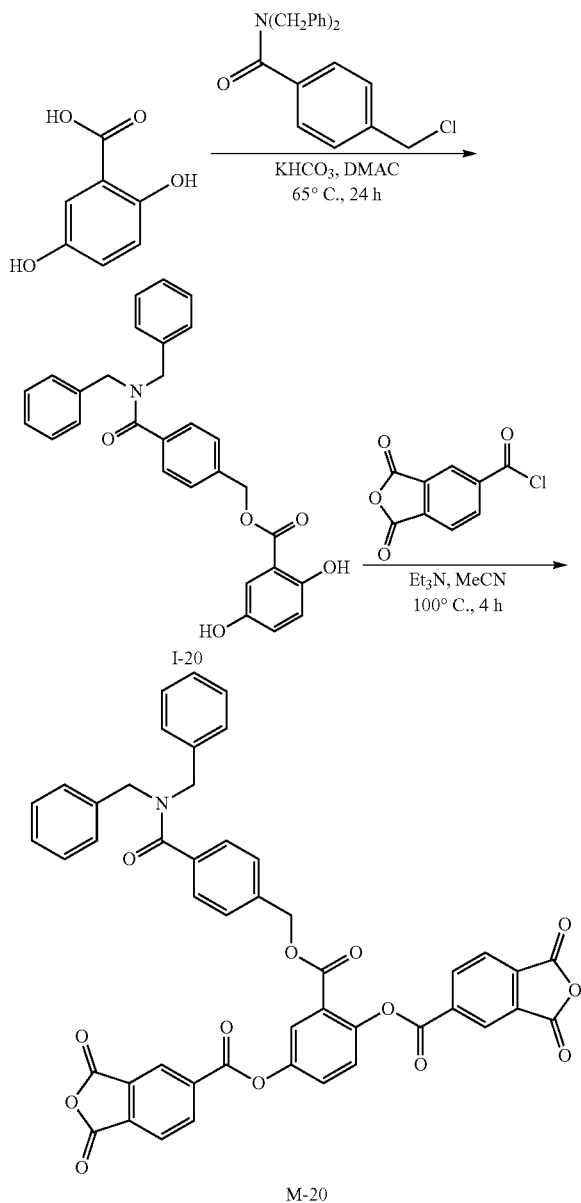

Reaction Scheme M-20

M-20

Step 1: Synthesis of Intermediate I-20 (2,5-dihydroxybenzoic acid 4-N,N-dibenzylcarbamoylbenzyl ester)

Intermediate I-20 is synthesized in a similar method to that of Intermediate I-1 by adding 2,5-dihydroxybenzoic acid (mw=154.12 g/mol, 128.24 mmol, m=19.76 gr), N,N-dibenzyl-4-chloromethylbenzamide (mw=349.86 g/mol, 124.51 mol, m=43.56 gr), and potassium hydrogen carbonate (mw=100.12 g/mol, 249.02 mmol, m=24.93 gr) to 0.2 L of dimethyl acetamide (DMAC), and reacting them under a nitrogen atmosphere at 65° C. for 24 hours. When the reaction is complete, the mixture is poured into 1 L of water, and a solid precipitated therein is filtered and twice crystallized with 400 mL of methanol. A product therefrom is dried at 70° C. under a reduced pressure for 12 hours. Intermediate I-20 is obtained therefrom as a white solid and has $R_f$=0.25 (Eluent: ethylacetate:hexane=1:2, TLC silica gel 60 F$_{254}$), mp=90-92° C., m=41.73 gr (mw=467.52 g/mol, 89.26 mmol), and yield of 71.7%.

$^1$H NMR (DMSO-d$_6$) 300 MHz, δ, ppm: 4.41 (s, 2H), 4.59 (s, 2H), 5.38 (s, 2H), 6.83 (d, 1H, $J^{12}$=9.0 Hz), 6.98 (dd, 1H, $J^{12}$=9.0 Hz, $J^{13}$=3.0 Hz), 7.14-7.19 (m, 3H), 7.26-7.36 (m, 8H), 7.53 (s, 4H), 9.20 (s, 1H), 9.90 (bs, 1H).

Step 2: Synthesis of Monomer M-20 (bis-trimellitic acid anhydride ester of 2,5-dihydroxybenzoic acid 4-N,N-dibenzylcarbamoylbenzyl ester)

Monomer M-20 is prepared in a similar method to that of Monomer M-1 by adding trimellitic anhydride chloride (mw=210.57 g/mol, 186.59 mmol, m=39.29 gr), Intermediate I-16 (2,5-dihydroxybenzoic acid 4-N,N-dibenzylcarbamoylbenzyl ester, mw=467.52 g/mol, 88.85 mmol, m=41.54 gr), and triethylamine (mw=101.19 g/mol, 195.47 mmol, m=19.78 gr) to 1 L of acetonitrile, and reacting them. When the reaction is complete, the obtained brown solution is filtered while hot to remove an insoluble material and concentrated down to 0.5 L of a volume. When the resultant is cooled down to room temperature, a white solid is produced. The solid is filtered and washed with a small amount of acetonitrile. A crude product therefrom is twice recrystallized with a mixture of acetonitrile (500 mL) and acetic anhydride (50 mL), and a product therefrom is dried under vacuum at 80° C. for 24 hours to obtain Monomer M-20 of a white crystalline solid as a final product. m=45.36 gr (mw=815.75 g/mol, 55.61 mmol), yield: 62.6%.

$^1$H NMR (DMSO-d$_6$) 300 MHz, δ, ppm: 4.31 (s, 2H), 4.54 (s, 2H), 5.22 (s, 2H), 7.11-7.35 (m, 14H), 7.64 (d, 1H, $J^{12}$=9.0 Hz), 7.84 (dd, 1H, $J^{12}$=9.0 Hz, $J^{13}$=3.0 Hz), 8.15 (d, 1H, $J^{13}$=3.0 Hz), 8.19 (d, 1H, $J^{12}$=8.1 Hz), 8.29 (d, 1H, $J^{12}$=8.1 Hz), 8.42 (s, 1H), 8.48 (dd, 1H, $J^{12}$=7.8 Hz, $J^{13}$=1.2 Hz), 8.64-8.67 (m, 2H). Thermal analysis: TGA (heating 10° C./min, N$_2$ atmosphere): 1 wt % loss (333.7° C.); DSC (heating 10° C./min, N$_2$ atmosphere): mp=225.9° C.

Preparation Example: Synthesis of Polymer and Manufacture of Film

Preparation Examples 1-1 to 1-8: Synthesis of Polyester-Imide and Manufacture of Film Each polyester-amic acid is prepared by reacting reactants including Monomer M-1 according to Example 1 and 6FDA or BPDA as additional dianhydride, and TFDB and/or DADPS as diamine, in a ratio shown in Table 1.

Specifically, each polyester-amic acid solution according to Preparation Examples 1-1 to 1-8 is prepared by dissolving 1 equivalent of TFDB and/or DADPS as a diamine in DMAc of an anhydrous solvent, adding 1 equivalent of a mixture of Monomer M-1 according to Example 1 as a dianhydride and 6FDA or BPDA as an additional dianhydride in a ratio shown in Table 1 to the solution, and stirring the mixture at 25° C. for 24 hours. The obtained polyamic acid solution is mixed with 3 equivalent of acetic anhydride and 3 equivalent of pyridine and stirred therewith at 25° C. for 12 hours to obtain a chemically partially imidized polyester-imide solution.

The polyester-imide solution is spin-coated at 1,000 revolutions per minute (rpm) to 3,000 rpm on a 50×50 millimeters (mm) glass substrate. The coated film is dried on a hot plate set at 80° C. for 30 minutes, heated at a speed of 10° C./min in a furnace from about 25° C. to about 230° C., and maintained at 230° C. for 30 minutes.

Preparation Examples 2 to 11

Each polyester-imide film according to Preparation Examples 2 to 11 is prepared according to the same method as Preparation Examples 1-1 to 1-8 except for preparing polyester-amic acid by preparing each dianhydride mixture of Monomers M-2 to M-14 according to Examples 2 to 14 instead of Monomer M-1 with 6FDA in a ratio shown in Table 1 and reacting the mixture with TFDB as diamine in a mole ratio of 1:1.

Preparation Examples 12 to 17

Each polyester-imide solution according to Preparation Examples 12 to 17 is prepared according to the same method as Preparation Examples 1-1 to 1-8 except for respectively mixing Monomers M-15 to M-20 according to Examples 15 to 20 instead of monomer M-1 according to Example 1 with 6FDA in a ratio shown in Table 1 to prepare each dianhydride mixture and reacting the dianhydride mixture with TFDB as diamine in a mole ratio of 1:1 to prepare polyester-amic acid.

The polyester-imide solution is precipitated in distilled water, ground with a blender, and cleaned with ethanol. A white precipitate is filtered, dried in an 80° C. oven overnight, and redissolved in cyclopentanone (CP).

The obtained polyester-imide solution in CP is spin-coated at 1,000 rpm to 3,000 rpm on a 50×50 mm glass substrate. The coated film is dried on a hot plate set at 80° C. for 30 minutes, heated at a speed of 10° C./min in a furnace from about 25° C. to about 170° C., and maintained at 170° C. for 120 minutes.

Comparative Preparation Examples 1 and 2

A film according to Comparative Preparation Example 1 is formed according to the same method as Preparation Examples 1-1 to 1-8 except for reacting 6FDA alone as dianhydride and TFDB alone as diamine in a ratio of 1:1 without using Monomers M-1 to M-20 according to Examples 1 to 20.

In addition, a film according to Comparative Preparation Example 2 is formed according to the same method as Preparation Examples 1-1 to 1-8 except for using 6FDA and TAHQ (hydroquinone bis(trimellitate dianhydride)) as dianhydride in a ratio shown in Table 1 and reacting the mixture with TFDB as diamine in a ratio of 1:1 to manufacture polyimide.

Evaluation

The composition, inherent viscosity ($\eta$), a thickness, transmittance (%), a yellow index (YI), an out-of-plane birefringence ($\Delta n_{th}$), and a glass transition temperature ($T_g$) of each film according to Preparation Examples 1-1 to 1-8 and 2 to 17 and Comparative Preparation Examples 1 and 2 are shown in Table 1. A method of measuring the thickness, out-of-plane birefringence, transmittance, yellow index, and glass transition temperature of the film is as follows:

(1) The film thickness is measured by using Filmetrics F20 (Filmetrics, Inc., Kanagawa, Japan).

(2) The out-of-plane birefringence ($\Delta n_{th}$) of the film is measured at a wavelength of 450 nanometers (nm) by using a prism coupler (Metricon MODEL 2010/M).

(3) Optical characteristics (transmittance and yellow index) of the film are measured by using a spectrophotometer, "Konica Minolta CM3600d," in a transmittance opacity/haze mode.

(4) The inherent viscosity is measured about 0.5 grams per deciliter (g/dL) of a polymer solution in DMAc by using Cannon PolyVisc Automated Viscosimeter.

(5) The glass transition temperature ($T_g$) is measured with a fixed tension force of 0.05 Newtons (N) at a speed of 5° C./min within a temperature range of 50° C. to 400° C. by using a thermal mechanical analyzer (TMA Q400, TA Instruments).

TABLE 1

| Examples | Composition | Ratio (mol part) | $\eta_{inh}$ (dL/g) | Film thickness (μm) | Solvent (PEI content, wt %) | $T_{450}$ (%) | Y.I. (%) | Haze (%) | $T_g$ (° C.) | $\Delta n_{th}$ |
|---|---|---|---|---|---|---|---|---|---|---|
| Preparation Example 1-1 | M1/6-FDA/TFDB | 8:2:10 | 0.87 | 6.1 | DMAc 15 | 89.49 | 0.54 | 0.24 | 221 | 0.0781 |
| Preparation Example 1-2 | M1/6-FDA/TFDB | 6:4:10 | 0.80 | 7.5 | DMAc 15 | 89.80 | 0.43 | 0.37 | 233 | 0.0687 |
| Preparation Example 1-3 | M1/6-FDA/TFDB | 4:6:10 | 0.74 | 5.5 | DMAc 15 | 89.39 | 0.55 | 0.24 | 260 | 0.0589 |
| Preparation Example 1-4 | M1/6-FDA/TFDB | 2:8:10 | 0.91 | 4.9 | DMAc 15 | 89.80 | 0.46 | 0.12 | 289 | 0.0505 |
| Preparation Example 1-5 | M1/6-FDA/DADPS | 5:5:10 | — | 5.9 | DMAc 18 | 88.70 | 0.60 | 0.23 | 269 | 0.0397 |

TABLE 1-continued

| Examples | Composition | Ratio (mol part) | $\eta_{inh}$ (dL/g) | Film thickness (μm) | Solvent (PEI content, wt %) | $T_{450}$ (%) | Y.I. (%) | Haze (%) | $T_g$ (° C.) | $\Delta n_{th}$ |
|---|---|---|---|---|---|---|---|---|---|---|
| Preparation Example 1-6 | M1/BPDA/DADPS | 5:5:10 | — | 9.0 | DMAc 18 | 88.42 | 0.73 | 0.15 | 274 | 0.0553 |
| Preparation Example 1-7 | M1/6-FDA/TFDB/DADPS | 8:2:9:1 | — | 13.5 | DMAc 18 | 88.34 | 0.99 | 0.18 | — | 0.09195 |
| Preparation Example 1-8 | M1/6-FDA/TFDB/DADPS | 8:2:7.5:2.5 | — | 8.8 | DMAc 18 | 88.73 | 0.68 | 0.19 | 225 | 0.06653 |
| Preparation Example 2 | M2/6-FDA/TFDB | 6:4:10 | 1.08 | 17.9 | DMAc 20 | 86.51 | 3.57 | 0.11 | — | 0.0565 |
| Preparation Example 3 | M3/6-FDA/TFDB | 8:2:10 | 1.55 | 7.4 | DMAc 15 | 89.32 | 0.60 | 0.36 | 218 | 0.0894 |
| Preparation Example 4 | M5/6-FDA/TFDB | 6:4:10 | 0.69 | 7.9 | DMAC 20 | 89.50 | 0.81 | 0.28 | — | 0.0635 |
| Preparation Example 5 | M7/6-FDA/TFDB | 8:2:10 | 1.80 | 5.7 | DMAc 9 | 89.55 | 0.48 | 0.33 | 232 | 0.0945 |
| Preparation Example 6 | M8/6-FDA/TFDB | 8:2:10 | 0.46 | 6.5 | DMAc 18 | 90.01 | 0.37 | 0.19 | 227 | 0.0440 |
| Preparation Example 7 | M10/6-FDA/TFDB | 8:2:10 | 0.43 | 6.8 | DMAc 20 | 89.10 | 1.07 | 0.45 | 242 | 0.0462 |
| Preparation Example 8 | M11/6-FDA/TFDB | 8:2:10 | 1.27 | 9.8 | DMAc 18 | 88.35 | 1.11 | 0.24 | 207 | 0.0729 |
| Preparation Example 9 | M12/6-FDA/TFDB | 8:2:10 | 0.74 | 7.9 | DMAc 18 | 88.72 | 0.81 | 0.13 | 227 | 0.0579 |
| Preparation Example 10 | M13/6-FDA/TFDB | 8:2:10 | 2.27 | 8.1 | DMAc 13 | 88.87 | 0.94 | 0.55 | 196 | 0.0688 |
| Preparation Example 11 | M14/6-FDA/TFDB | 8:2:10 | 0.93 | 9.5 | DMAc 17 | 88.40 | 1.00 | 0.29 | 201 | 0.0816 |
| Preparation Example 12 | M15/6-FDA/TFDB | 8:2:10 | 1.22 | 5.9 | CP 9 | 89.03 | 0.65 | 0.11 | 170 | 0.0809 |
| Preparation Example 13 | M16/6-FDA/TFDB | 8:2:10 | 0.48 | 6.7 | CP 18 | 88.80 | 0.94 | 0.22 | 154 | 0.0572 |
| Preparation Example 14 | M17/6-FDA/TFDB | 8:2:10 | 1.45 | 5.1 | CP 10 | 88.21 | 1.41 | 0.24 | 189 | 0.0930 |
| Preparation Example 15 | M18/6-FDA/TFDB | 8:2:10 | 1.72 | 6.1 | CP 9 | 89.78 | 0.45 | 0.26 | 194 | 0.08574 |
| Preparation Example 16 | M19/6-FDA/TFDB | 8:2:10 | 1.20 | 5.3 | CP 12 | 89.26 | 0.57 | 0.15 | 162 | 0.0724 |
| Preparation Example 17 | M20/6-FDA/TFDB | 8:2:10 | 0.91 | 5.4 | CP 10 | 88.73 | 0.69 | 0.14 | 196 | 0.0692 |
| Comparative Preparation Example 1 | 6-FDA/TFDB | 10:10 | 0.73 | 5.0 | DMAc 15 | 90.63 | 0.31 | 0.21 | 320 | 0.0429 |
| Comparative Preparation Example 2 | THQA/6-FDA/TFDB | 8:2:10 | 1.07 | 5.6 | DMAc 9 | 87.55 | 1.71 | 0.44 | 244 | 0.1304 |

As shown in Table 1, a polyester-imide film prepared from reactants including a dianhydride including an ester group according to an embodiment has high transmittance at 450 nm, a low yellow index, and low haze, as well as shows a high out-of-plane birefringence ranging from at least about 0.04 to at most about 0.09, and thus, has excellent optical characteristics. In addition, the film has a glass transition temperature within a predetermined or higher range, and thus, high thermal stability. In other words, since a film formed from aromatic dianhydride including an ester group according to an embodiment and aromatic diamine shows equivalent or more excellent optical properties, as well as equivalent or satisfactory thermal stability, compared with a polyimide film prepared by using conventional aromatic dianhydride and aromatic diamine and having high thermal stability and excellent optical properties according to Comparative Preparation Example 1 or 2, a film having excellent optical properties and thermal stability may be formed by reacting novel dianhydride including an ester group according to an embodiment alone or together with conventional aromatic dianhydride having excellent optical characteristics and a conventional aromatic diamine. This ester group-containing dianhydride according to an embodiment has a low preparation cost compared with the conventional aromatic dianhydride having excellent optical properties and thermal stability, and thus, may remarkably reduce a manufacturing cost, while having excellent optical properties and thermal stability during manufacture of an optical film.

While this disclosure has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A monomer represented by Chemical Formula 1:

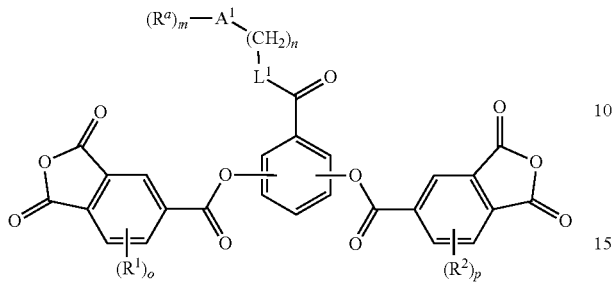

Chemical Formula 1 wherein, in Chemical Formula 1, $R^1$ and $R^2$ are independently a substituted or unsubstituted C1 to C30 alkyl group, a substituted or unsubstituted C1 to C30 cycloalkyl group, a substituted or unsubstituted C3 to C30 alkoxy group, a substituted or unsubstituted C3 to C30 cycloalkoxy group, a substituted or unsubstituted C6 to C30 aryl group, a substituted or unsubstituted C2 to C30 acyl group, a hydroxy group, a halogen, a nitro group, —NR'R" (wherein R' and R" are independently hydrogen, a C1 to C30 alkyl group, or a C6 to C30 aryl group), —SiR'R"R''' (wherein R', R", and R''' are independently hydrogen, a C1 to C30 alkyl group, or a C6 to C30 aryl group), or a combination thereof, o and p are independently an integer ranging from 0 to 3, $L^1$ is O or $NR^b$ (wherein $R^b$ is hydrogen or a C1 to C20 alkyl group), $A^1$ is a C6 to C30 aromatic organic group, and $R^a$ is hydrogen, a substituted or unsubstituted C1 to C30 alkyl group, a substituted or unsubstituted C1 to C30 alkoxy group, a substituted or unsubstituted C3 to C30 cycloalkyl group, a substituted or unsubstituted C3 to C30 cycloalkoxy group, a substituted or unsubstituted C6 to C30 aryl group, a substituted or unsubstituted C7 to C30 arylalkyl group, a hydroxy group, a halogen, a nitro group, —NR'R" (wherein R' and R" are independently hydrogen, a C1 to C30 alkyl group, a C6 to C30 aryl group, or a C7 to C30 arylalkyl group), —CO—NR'R" (wherein R' and R" are independently hydrogen, a C1 to C30 alkyl group, a C6 to C30 aryl group, or a C7 to C30 arylalkyl group), —SiR'R"R''' (wherein R', R", and R''' are independently hydrogen, a C1 to C30 alkyl group, a C6 to C30 aryl group, or a C7 to C30 arylalkyl group), or a group represented by Chemical Formula 2:

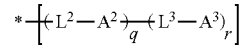

Chemical Formula 2 wherein, in Chemical Formula 2, $L^2$ and $L^3$ are independently O, CO, COO, C≡C, or $CONR^b$ (wherein $R^b$ is hydrogen or a C1 to C30 alkyl group), $A^2$ and $A^3$ are independently a substituted or unsubstituted C6 to C30 aromatic ring, a substituted or unsubstituted fluorene ring, or a substituted or unsubstituted C7 to C20 arylalkyl group, q and r are independently an integer ranging from 0 to 3, m is an integer ranging from 0 to 3, and n is an integer ranging from 0 to 20.

2. The monomer of claim 1, wherein o and p of Chemical Formula 1 are independently 0 or 1, $L^1$ is O or $NR^b$ (wherein $R^b$ is hydrogen or a C1 to C20 alkyl group), $A^1$ is a C6 to C20 aromatic organic group, $R^a$ is hydrogen, a substituted or unsubstituted C1 to C20 alkyl group, a substituted or unsubstituted C1 to C20 alkoxy group, a substituted or unsubstituted C7 to C20 arylalkyl group, a halogen, —NR'R" (wherein R' and R" are independently hydrogen, a C1 to C30 alkyl group, a C6 to C30 aryl group, or a C7 to C30 arylalkyl group), —CO—NR'R" (wherein R' and R" are independently hydrogen, a C1 to C30 alkyl group, a C6 to C30 aryl group, or a C7 to C30 arylalkyl group), —SiR'R"R''' (wherein R', R", and R''' are independently hydrogen or a C1 to C20 alkyl group), or a group represented by Chemical Formula 2:

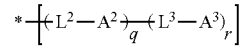

Chemical Formula 2 wherein, in Chemical Formula 2, $L^2$ and $L^3$ are independently COO, C≡C, or $CONR^b$ (wherein $R^b$ is hydrogen or a C1 to C20 alkyl group), $A^2$ and $A^3$ are independently a substituted or unsubstituted C6 to C20 aromatic ring, a substituted or unsubstituted fluorene ring, or a substituted or unsubstituted C7 to C20 arylalkyl group, q and r are independently an integer ranging from 0 to 2, provided that 1≤q+r≤2, m is an integer ranging from 0 to 2, and n is an integer ranging from 0 to 10.

3. The monomer of claim 1, wherein o and p of Chemical Formula 1 are independently 0 or 1, $L^1$ is O or NH, $A^1$ is a benzene ring, and $R^a$ is hydrogen, a substituted or unsubstituted C1 to C20 alkyl group, a substituted or unsubstituted C1 to C20 alkoxy group, a halogen, —CO—NR'R" (wherein R' and R" are independently hydrogen, a C1 to C30 alkyl group, a C6 to C30 aryl group, or a C7 to C30 arylalkyl group), or a group represented by Chemical Formula 2:

Chemical Formula 2 wherein, in Chemical Formula 2, $L^2$ and $L^3$ are independently COO, C≡C, or $CONR^b$ (wherein $R^b$ is hydrogen or a C1 to C20 alkyl group), $A^2$ and $A^3$ are independently a substituted or unsubstituted benzene ring, a substituted or unsubstituted fluorene ring, or a substituted or unsubstituted C7 to C20 arylalkyl group, q and r are independently an integer ranging from 0 to 2, provided that 1≤q+r≤2, m is 0 or 1, and n is an integer ranging from 0 to 5.

4. The monomer of claim 1, wherein the monomer represented by Chemical Formula 1 is a monomer represented by Chemical Formula 3 or a monomer represented by Chemical Formula 4:

Chemical Formula 3

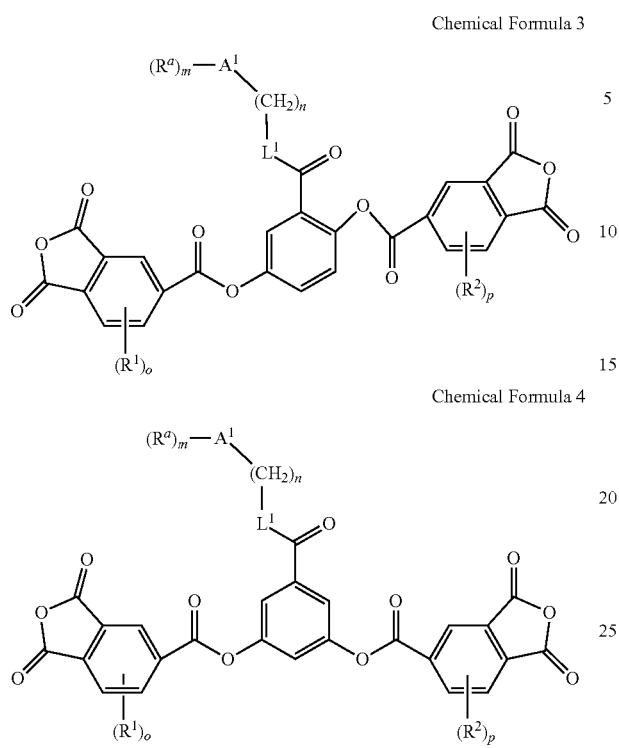

Chemical Formula 4 wherein, in Chemical Formula 3 and Chemical Formula 4, $R^1$ and $R^2$ are independently a substituted or unsubstituted C1 to C30 alkyl group, a substituted or unsubstituted C3 to C30 cycloalkyl group, a substituted or unsubstituted C1 to C30 alkoxy group, a substituted or unsubstituted C3 to C30 cycloalkoxy group, a substituted or unsubstituted C6 to C30 aryl group, a substituted or unsubstituted C1 to C30 acyl group, a hydroxy group, a halogen, a nitro group, —NR'R" (wherein R' and R" are independently hydrogen, a C1 to C30 alkyl group, or a C6 to C30 aryl group), —SiR'R"R'" (wherein R', R", and R'" are independently hydrogen or a C1 to C20 alkyl group), or a combination thereof, o and p are independently an integer ranging from 0 to 3, $L^1$ is O or $NR^b$ (wherein $R^b$ is hydrogen or a C1 to C20 alkyl group), $A^1$ is a C6 to C30 aromatic organic group, and $R^a$ includes a substituted or unsubstituted C1 to C30 alkyl group, a substituted or unsubstituted C1 to C30 alkoxy group, a substituted or unsubstituted C3 to C30 cycloalkyl group, a substituted or unsubstituted C3 to C30 cycloalkoxy group, a substituted or unsubstituted C6 to C30 aryl group, a substituted or unsubstituted C7 to C30 arylalkyl group, a hydroxy group, a halogen, a nitro group, —NR'R" (wherein R' and R" are independently hydrogen, a C1 to C30 alkyl group, a C6 to C30 aryl group, or a C7 to C30 arylalkyl group), —CO—NR'R" (wherein R' and R" are independently hydrogen, a C1 to C30 alkyl group, a C6 to C30 aryl group, or a C7 to C30 arylalkyl group), —SiR'R"R'" (wherein R', R", and R'" are independently hydrogen, C1 to C30 alkyl group, or C7 to C30 arylalkyl group), or a group represented by Chemical Formula 2:

Chemical Formula 2

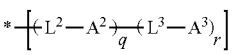

wherein, in Chemical Formula 2, $L^2$ and $L^3$ are independently O, CO, COO, C≡C, or $CONR^b$ (wherein $R^b$ is hydrogen or a C1 to C20 alkyl group), $A^2$ and $A^3$ are independently a substituted or unsubstituted C6 to C30 aromatic ring, a substituted or unsubstituted fluorene ring, or a substituted or unsubstituted C7 to C30 arylalkyl group, q and r are independently an integer ranging from 0 to 3, m is an integer ranging from 0 to 3, and n is an integer ranging from 0 to 20.

5. The monomer of claim 4, wherein o and p of Chemical Formula 3 and Chemical Formula 4 are independently 0 or 1, $L^1$ is O or $NR^b$ (wherein $R^b$ is hydrogen or a C1 to C20 alkyl group), $A^1$ is a C6 to C20 aromatic organic group, and $R^a$ is hydrogen, a substituted or unsubstituted C1 to C20 alkyl group, a substituted or unsubstituted C1 to C20 alkoxy group, a substituted or unsubstituted C7 to C20 arylalkyl group, a halogen, —NR'R" (wherein R' and R" are independently hydrogen, a C1 to C30 alkyl group, a C6 to C30 aryl group, or a C7 to C30 arylalkyl group), —CO—NR'R" (wherein R' and R" are independently hydrogen, a C1 to C30 alkyl group, a C6 to C30 aryl group, or a C7 to C30 arylalkyl group), —SiR'R"R'" (wherein R', R", and R'" are independently hydrogen, C1 to C20 alkyl group, a C6 to C30 aryl group, or a C7 to C30 arylalkyl group), or a group represented by Chemical Formula 2:

Chemical Formula 2

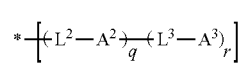

wherein, in Chemical Formula 2, $L^2$ and $L^3$ are independently COO, C≡C, or $CONR^b$ (wherein $R^b$ is hydrogen or a C1 to C20 alkyl group), $A^2$ and $A^3$ are independently a substituted or unsubstituted C6 to C20 aromatic ring, a substituted or unsubstituted fluorene ring, or a substituted or unsubstituted C7 to C20 arylalkyl group, q and r are independently an integer ranging from 0 to 2, provided that 1≤q+r≤2, m is 0 or 1, and n is an integer of 0 to 10.

6. The monomer of claim 4, wherein o and p of Chemical Formula 3 and Chemical Formula 4 are all 0, $L^1$ is O or NH, $A^1$ is a benzene ring, and $R^a$ is hydrogen, a substituted or unsubstituted C1 to C10 alkyl group, a substituted or unsubstituted C1 to C10 alkoxy group, a halogen, —CO—NR'R" (wherein R' and R" are independently hydrogen, a C1 to C30 alkyl group, a C6 to C30 aryl group, or a C7 to C30 arylalkyl group), or a group represented by Chemical Formula 2:

Chemical Formula 2

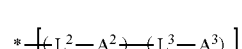

wherein, in Chemical Formula 2, $L^2$ and $L^3$ are independently COO, C≡C, or $CONR^b$ (wherein $R^b$ is hydrogen or a C1 to C20 alkyl group), $A^2$ and $A^3$ are independently a substituted or unsubstituted benzene ring, a substituted or unsubstituted fluorene ring, or a substituted or unsubstituted C7 to C20 arylalkyl group, q and r are independently an integer ranging from 0 to 2, provided that $1 \leq q+r \leq 2$, m is 0 or 1, and n is an integer ranging from 0 to 5.

* * * * *